(12) United States Patent
Takarada et al.

(10) Patent No.: US 11,069,441 B2
(45) Date of Patent: Jul. 20, 2021

(54) BIOLOGICAL INFORMATION MEASUREMENT DEVICE AND BIOLOGICAL INFORMATION MEASUREMENT METHOD

(71) Applicant: PHC HOLDINGS CORPORATION, Tokyo (JP)

(72) Inventors: Shinichi Takarada, Ehime (JP); Noriyoshi Terashima, Tokyo (JP)

(73) Assignee: PHC HOLDINGS CORPORATION, Tokyo (JP)

( * ) Notice: Subject to any disclaimer, the term of this patent is extended or adjusted under 35 U.S.C. 154(b) by 497 days.

(21) Appl. No.: 15/760,867

(22) PCT Filed: Oct. 14, 2016

(86) PCT No.: PCT/JP2016/080549
§ 371 (c)(1),
(2) Date: Mar. 16, 2018

(87) PCT Pub. No.: WO2017/073371
PCT Pub. Date: May 4, 2017

(65) Prior Publication Data
US 2019/0088351 A1    Mar. 21, 2019

(30) Foreign Application Priority Data
Oct. 28, 2015 (JP) .............................. JP2015-211415

(51) Int. Cl.
*G16H 40/63* (2018.01)
*A61B 5/00* (2006.01)
(Continued)

(52) U.S. Cl.
CPC ............... *G16H 40/63* (2018.01); *A61B 5/00* (2013.01); *A61B 5/14532* (2013.01);
(Continued)

(58) Field of Classification Search
CPC ........ G16H 10/60; G16H 10/65; G16H 15/00; A61B 5/00; A61B 5/14532;
(Continued)

(56) References Cited

U.S. PATENT DOCUMENTS 5,371,687 A    12/1994  Holmes, II et al.
8,380,542 B2    2/2013  Wons et al.
(Continued)

FOREIGN PATENT DOCUMENTS

CN    101730856    6/2010
CN    103997952    8/2014
(Continued)

OTHER PUBLICATIONS

International Search Report dated Dec. 27, 2016 in International (PCT) Application No. PCT/JP2016/080549.
(Continued)

*Primary Examiner* — Linh Giang Le
(74) *Attorney, Agent, or Firm* — Wenderoth, Lind & Ponack, L.L.P.

(57) ABSTRACT

A blood glucose measurement device comprises a sensor connector, a blood glucose value calculator, a barcode reader, a liquid crystal display, a data storage component, a report storage area, a central controller, and a touch sensor. The central controller causes the liquid crystal display to activate an input screen for inputting a comment for each measurement by the blood glucose value calculator. When a comment is inputted to the touch sensor, the central controller associates the comment with identification information in correspondence with each measurement by the blood glucose value calculator and stores the result in the report storage area. When a patient ID is read by the barcode reader, the central controller checks whether there is a comment on the basis of the information stored in the report
(Continued)

storage area, and if there is a comment, the comment is displayed on the liquid crystal display.

1 Claim, 63 Drawing Sheets

(51) Int. Cl.
*A61B 5/145* (2006.01)
*G16H 10/65* (2018.01)
*G16H 15/00* (2018.01)
*G16H 10/60* (2018.01)
*G01N 15/06* (2006.01)
*G01N 33/49* (2006.01)
*A61B 5/15* (2006.01)
*A61B 90/96* (2016.01)
*G01N 15/00* (2006.01)

(52) U.S. Cl.
CPC ..... *G01N 15/0606* (2013.01); *G01N 15/0656* (2013.01); *G01N 33/49* (2013.01); *G16H 10/60* (2018.01); *G16H 10/65* (2018.01); *G16H 15/00* (2018.01); *A61B 5/0022* (2013.01); *A61B 5/150022* (2013.01); *A61B 5/150358* (2013.01); *A61B 5/7275* (2013.01); *A61B 90/96* (2016.02); *A61B 2562/0295* (2013.01); *G01N 2015/0065* (2013.01)

(58) Field of Classification Search
CPC ...... A61B 5/150358; A61B 2562/0295; A61B 5/150022; A61B 5/0022; A61B 5/7275; A61B 90/96; G01N 15/0606; G01N 15/0656; G01N 33/49; G01N 2015/0065
See application file for complete search history.

(56) References Cited

U.S. PATENT DOCUMENTS

| | | | |
|---|---|---|---|
| 9,684,763 B2* | 6/2017 | Terashima | G01N 33/50 |
| 2004/0210466 A1 | 10/2004 | Hasebe et al. | |
| 2005/0033736 A1* | 2/2005 | Carlin | G06Q 10/10 |
| 2007/0005397 A1 | 1/2007 | Lee | |
| 2007/0156456 A1 | 7/2007 | McGillin et al. | |
| 2010/0072271 A1 | 3/2010 | Thorstensson | |
| 2012/0029303 A1 | 2/2012 | Shaya | |
| 2012/0136221 A1 | 5/2012 | Killen et al. | |
| 2012/0250961 A1 | 10/2012 | Iwasaki | |
| 2013/0041591 A1* | 2/2013 | Lamego | A61B 5/14551 702/19 |
| 2013/0104890 A1 | 5/2013 | Steinhauer et al. | |
| 2014/0067425 A1 | 3/2014 | Dudar et al. | |
| 2014/0200921 A1 | 7/2014 | Hamill et al. | |
| 2014/0367256 A1 | 12/2014 | Terashima et al. | |
| 2015/0130830 A1 | 5/2015 | Nagasaki et al. | |
| 2015/0153301 A1 | 6/2015 | Yoshioka | |
| 2015/0216454 A1 | 8/2015 | Kasahara et al. | |
| 2017/0023517 A1 | 1/2017 | Yoshioka | |
| 2017/0245938 A1 | 8/2017 | Terashima et al. | |
| 2017/0324930 A1 | 11/2017 | Shaya | |
| 2017/0332972 A1 | 11/2017 | Nagasaki et al. | |
| 2018/0158540 A1 | 6/2018 | Terashima et al. | |
| 2019/0122755 A1 | 4/2019 | Dudar et al. | |

FOREIGN PATENT DOCUMENTS

| | | |
|---|---|---|
| CN | 104380097 | 2/2015 |
| CN | 104545804 | 4/2015 |
| CN | 104814746 | 8/2015 |
| CN | 104823193 | 8/2015 |
| JP | 2002-157333 | 5/2002 |
| JP | 2002-269226 | 9/2002 |
| JP | 2004-325509 | 11/2004 |
| JP | 2006-134177 | 5/2006 |
| JP | 2006-260437 | 9/2006 |
| JP | 2010-61270 | 3/2010 |
| JP | 2015-175 | 1/2015 |
| WO | 2008/130298 | 10/2008 |
| WO | 2012/015543 | 2/2012 |
| WO | 2013/099236 | 7/2013 |
| WO | 2014/039835 | 3/2014 |

OTHER PUBLICATIONS

"ACCU-CHEK Inform II Operator's Manual (Version 3.0)", 2013, Roche Diagnostics, Indianapolis, IN, USA.
Office Action dated Apr. 19, 2021 in Chinese Patent Application No. 201680051895.9, with English-language translation.

* cited by examiner

| Number | Type | Content of Data | Purpose |
|---|---|---|---|
| medical data 1 | conventional | measurement attribute | Primarily to ascertain patient's health and ensure reliability thereof |
| medical data 2 | conventional | user ID | |
| medical data 3 | conventional | sensor ID | |
| medical data 4 | conventional | patient ID (QC solution ID) | |
| medical data 5 | conventional | blood glucose value | |
| medical data 6 | conventional | date and time of measurement | |
| medical data 7 | conventional | comment | |
| metric data 1 | novel | time required for user ID scan | To ascertain work efficiency, device status, etc. |
| metric data 2 | novel | time required for sensor ID scan | |
| metric data 3 | novel | time required for patient ID scan | |
| metric data 4 | novel | time required for patient confirmation | To ascertain rule compliance situation |
| metric data 5 | novel | time required for entire measurement | To ascertain work efficiency |
| metric data 6 | novel | Number of screen touches required for entire measurement | To ascertain level of proficiency |

FIG. 21

| | Metric | Processing | Meaning (possibility) | Measures |
|---|---|---|---|---|
| 4301 | blood deposition time | compare for each user | longer time means inexperienced | train user |
| 4302 | length of time until sensor is removed | compare for each patient | patient with longer time means blood collection difficult | advise user |
| 4303 | "help" usage count | compare for each user | longer means risk of infection | safety training for user |
| 4304 | "back" usage count | compare for each user | more times means inexperienced | train user |
| 4305 | number of warnings | compare for each user | more times means inexperienced | train user |
| 4306 | comment input time | compare for each user | more times means inexperienced | train user |
| 4307 | remaining battery charge | compare number of charges for each user | fewer times means rule violation | educate user |
| | | compare capacity after charging for each measurement device | lower means battery dead | replace battery |
| 4308 | wireless link time | compare for each location | slower means wireless problem | improve system |
| 4309 | cleaning time | compare for each user | longer means risk of infection | safety training for user |
| 4310 | Number of discarded measurements | compare for each user | user with more times means inexperienced | train user |
| | | compare for each measurement device | device with more times means malfunction | repair measurement device |
| | | compare for each patient | patient with more times means there is a problem | advise user |

FIG. 43

| Metric | Processing | Meaning (possibility) | Measures |
|---|---|---|---|
| QC results | compare accuracy for each user | more errors means inexperienced | train user |
| STAT measurement | compare usage frequency for each user | higher means rule violation | educate user |
| measurement device ID | compare usage frequency for each measurement component | variance in measurement device operation rate | optimize measurement device layout |
| sensor ID | compare number of sensors discarded due to being expired for each user | higher number means lack of awareness | educate user |
| comments | compare number of custom comments for each comment | comment list is inadequate | add comments |

1. Select pain experienced during this measurement
   not painful → excruciatingly painful
   0 1 2 3 4 5 6 7 8 9 10

2. Select degree of satisfaction with this measurement
   very unsatisfied   unsatisfied   neutral   satisfied   very satisfied 3. Select any that apply
   ☐ It hurt
   ☑ It took a long time
   ☐ It was stressful
   ☑ Unsatisfied with diet

OK

BIOLOGICAL INFORMATION MEASUREMENT DEVICE AND BIOLOGICAL INFORMATION MEASUREMENT METHOD

TECHNICAL FIELD

The present invention relates to a biological information measurement device and a biological information measurement method with which a nurse or the like goes to a hospital room or a laboratory and conduct patient examinations in hospitals or clinics.

BACKGROUND ART

In ordinary Japanese hospitals and clinics, nursing is carried out by shifts of nurses. Therefore, the nurse in charge is generally replaced according to the care period. In such a case, there are cases where it is desirable for a nurse to report what he or she has noticed during measurement for use during the next measurement with a blood glucose level or other such biological information measurement device that the nurse brings into the patient's room to measure the patient's biological information.

For example, if the blood glucose level is high, whether this is due to a medical condition or to snacking by the patient is an important detail for diagnosis. Accordingly, after checking with the patient, the nurse writes this information down in the medical record along with the numerical value. At the time of the next measurement, the nurse who does the measurement may not be the same one as the previous time. In that case, the nurse can refer to the medical record to check the previous situation, and if the patient had eaten a snack the previous time, the nurse can again check for snacking, etc., and this can be linked to instructions, etc.

In this way, anything involved in diagnosis can be referred to by noting it the medical record. However, depending on the situation, there are also times when you may want to report items that are not the kind to be written in the medical record.

For example, if a nurse tries unsuccessfully several times to take blood from a patient and causes the patient to feel pain, a report can be made telling the nurse during the next exam to touch on this and to apologize to the patient and be extra careful, which will give the patient a sense of safety and trust. In such a case, it has been customary in the past for such information to be conveyed during the next exam through a memo or the like.

Also, in the United States, in most states other than California, in order to reduce costs, a high school graduate-level full-time blood taker (phlebotomist) is the one who measures blood glucose levels, and a nurse makes clinical decisions about the measured values and enters the clinical treatment details and measured values in the electronic medical record.

What has been regarded as a problem in many hospitals is the reporting of measured values. More specifically, a full-time phlebotomist will jot down measurement values on a sticky note or other such memo pad, or will write down the measurement values on a small white board that is left at the side of the patient's bed. Because of this, market research has shown that a wide variety of accidents happen in actual practice, such as the paper on which the wrong measurement value was written or the measurement values were written being lost, or the nurse performing clinical treatment based on measurement values when it is unknown when the measurement was done.

Patent Literature 1, for example, proposes a method for reporting this information more reliably, in which an area in which a comment is always displayed is added to the screen of a biological information measurement device, so that the details to be reported are always displayed, and a nurse can operate the device as needed to refer to a detailed account.

Also, Patent Literature 2, for example, proposes a method for when you want to report about unfinished work, rather than the details that are written in a medical record. With this method, a means for registering the details of the unfinished work as report information is prepared for the nurse who will be taking over, and that information is reflected in the scheduling of the nurse who takes over the task.

Furthermore, according to Patent Literature 3, after measurement with a blood glucose measurement device designed for hospital use, comments from the person who took the measurement are electronically recorded at the time of displaying the measurement result. With this blood glucose measurement device, the measurer chooses the best of the comments from the comment table and uses the barcode reader to read the barcode tied to the comment. Consequently, the blood glucose measurement value and the comments can be stored in the patient record data.

Also, in Non-Patent Literature 1 related to a commercially available blood glucose measurement device intended for hospital use, comments are sent to a laboratory terminal along with measurement results, the measurement date and time, the names of the measurer and the patient, and other such information, and the required information is taken from these by the examination manager and recorded to an electronic medical record, etc.

Here, a conventional biological information measurement device including a blood glucose measurement device is a device whose purpose is to measure biological information. Thus, the information to be recorded/transferred is of course just the measurement result and information for confirming its reliability.

For instance, Patent Literature 4 proposes a system in which test questions for skill evaluation are prepared, the test subject is asked to answer these questions, and the answers are scored to evaluate the skill of the respondent. With this method, however, it is necessary to have the subjects take the test individually.

Therefore, Patent Literature 5 proposes a way to judge skill without a test, in which skill is evaluated by measuring how long it takes to answer specific questions that are asked in the course of carrying out ordinary work, so that no special test is required.

Furthermore, Patent Literature 2 proposes a means for improving the accuracy of scheduling by measuring how long actual treatment takes in normal work in order to calculate an accurate nursing work time, and thereby finding the required time for each patient and nurse. Here again, there is no need to separately carry out a test or other such method.

Patent Literature 6 discloses a system and method with which a healthcare provider can access an electronic medical record on a server not only from inside a hospital but also from outside the hospital via a gateway at a computer in the course of at-home medical care. In addition, this system allows measurement device results (such as from a blood pressure monitor) to be uploaded to the server, and these can be accessed by a healthcare provider in the same way as a patient record on some other kind of electronic medical record.

Patent Literature 7 discloses a system in which vital signs such as the pulse rate, body temperature, blood pressure, respiratory rate, blood saturated oxygen concentration, and inhaled oxygen amount of a hospitalized patient are collected, a scoring engine finds a status based on vital sign information, and the information thus found is sent as a message to a healthcare provider. With this system, an existing bedside monitor is combined with a receiver and an electronic device that collects and analyzes information from the bedside monitor and sends out messages, so that in the event of an emergency, a healthcare provider can check on the patient's vital signs even from far away.

Patent Literature 8 discloses a method for analyzing medical device data. More specifically, data acquired from a ventilator or from a camera, a microphone, or the like that is connected to a ventilator is analyzed, and the trend is measured. The result is then used to improve of training of healthcare provider, etc.

Patent Literature 9 discloses a method for accessing or maintaining a digitized medical record in an electronic medical record system, an order system, or the like with a handheld computer. This makes it possible for various healthcare workers to securely check the location of a patient and the patient's record and update these to the most current information, confirm the order and the results of a clinical trial, confirm allergy information or side effects of a drug and send a prescription to a pharmacist, and so forth.

Patent Literature 10 discloses a function with which an electronic medical recording system having a medical ordering function prevents erroneous input when inputting a new order. More specifically, it is possible to prevent medical accidents by finding identical or similar orders and displaying the differences with highlighting or colored fonts of the text.

Also, Patent Literature 11 discloses a system for monitoring work related to treatment in a medical facility. This system can provide resource status information about patients, medical equipment, healthcare providers, and so forth within a medical facility, and allows for adjustment to optimize patient care with existing medical equipment and medical staff.

On the other hand, from the viewpoint of the administrative department of a hospital, there are many other types of information that should be grasped, such as the skill of the nurses and work efficiency, in addition to information aimed at patient diagnostic. Many methods have been proposed as a way to evaluate skill, regardless of the nurse in question.

For example, Patent Literature 4 proposes a way to evaluate the skill of a respondent by preparing test questions for skill evaluation, having the subject answer the questions, and scoring the answers. With this method, however, it is necessary to have the subjects take tests individually.

Therefore, Patent Literature 5 proposes a way to judge skill without a test, in which skill is evaluated by measuring how long it takes to answer specific questions that are asked in the course of carrying out ordinary work, so that no special test is required.

Furthermore, Patent Literature 2 proposes a means for improving the accuracy of scheduling by measuring how long actual treatment takes in normal work in order to calculate an accurate nursing work time, and thereby finding the required time for each patient and nurse. Here again, there is no need to separately carry out a test or other such method.

Also, Patent Literature 5 discloses a system and method with which a healthcare provider can access an electronic medical record on a server not only from inside a hospital but also from outside the hospital via a gateway at a computer in the course of at-home medical care. With this system, for example, a measurement result such as a blood pressure reading can be uploaded to the server and accessed by a healthcare provider in the same way as a patient record on some other kind of electronic medical record.

Patent Literature 6 discloses a system in which vital signs such as the pulse rate, body temperature, blood pressure, respiratory rate, blood saturated oxygen concentration, and inhaled oxygen amount of a hospitalized patient are collected, a scoring engine finds a status based on vital sign information, and the information thus found is sent as a message to a healthcare provider.

With this system, however, an existing bedside monitor is combined with a receiver and an electronic device that collects and analyzes information from the bedside monitor and sends out messages, so that in the event of an emergency, a healthcare provider can check on the patient's vital signs even from far away.

CITATION LIST

Patent Literature

Patent Literature 1: JP-A 2015-175
Patent Literature 2: JP-A 2006-260437
Patent Literature 3: U.S. Pat. No. 5,371,687
Patent Literature 4: JP-A 2004-325509
Patent Literature 5: JP-A 2006-134177
Patent Literature 6: U.S. Pat. No. 8,380,542
Patent Literature 7: US 2012/0136221
Patent Literature 8: US 2013/0104890
Patent Literature 9: US 2007/0005397
Patent Literature 10: US 2014/0200921
Patent Literature 11: US 2007/0156456

Non-Patent Literature

Non-Patent Literature 1: Accu-Chek InForm II operator's manual (version 3.0)

SUMMARY

Technical Problem

However, with the conventional configurations discussed above, as shown in the previous example, if a nurse tried unsuccessfully several times to take blood from a patient and caused the patient pain, it was difficult to convey this to the next measurer. For instance, since details not related to diagnosis are not inputted to a medical record, it was difficult to convey the necessary information to the measurer with a method involving a medical record.

Also, with a method involving a memo, which is what is most frequently used, information may not be transmitted in a timely manner at the next measurement due to lost or overlooked memos.

Furthermore, with the method according to Patent Literature 1, a reported comment itself, or a mark indicating that a comment exists, is always displayed. Therefore, the next measurer must notice the mark during this measurement and then take it upon himself or herself to go to see the details of what is being reported. Thus, here again, there is a possibility that the report may end up being buried in the large amount of information on the screen, so that it goes unnoticed and the report is overlooked.

Also, constantly displaying comments means that a great deal of information is displayed on the screen at the same time. Therefore, necessary information ends up being buried and it is harder to ascertain the information that is necessary right now, and at the same time, there are problems such as difficulty in reading text because the font becomes smaller, especially on small portable screens.

With the method according to Patent Literature 2, although unfinished work is reported, the details are not transmitted to the next nurse, and instead are just automatically used for scheduling. Therefore, there is no mention of an effective and clear way to convey the details to the next nurse.

Also, blood glucose measurement devices intended for hospital use have a function of sending comments to a laboratory terminal. However, these comments are intended to be recorded in an electronic medical record for reference in diagnosis, or for reference about the condition for evaluating the reliability of measured data. Thus, no means is provided for notifying the next person who takes measurements.

Also, with the methods according to Patent Literature 3 and Non-Patent Literature 1, even if an attempt is made to check the past values measured with an in-hospital blood glucose measurement device, it is impractical for a busy nurse to have to find out which blood glucose measurement device was used. Also, access to a DMS (data management system) in which in-hospital blood glucose measurement devices transmit measurement results through a cradle is limited to the POCC (point of care coordinator) of a clinical laboratory, and cannot be accessed by a nurse. That is, just looking at the actual places where blood glucose levels are measured in hospitals, all over the world, makes it clear that there is a problem in detailed communication between busy nurses and other healthcare providers who work in healthcare settings.

Meanwhile, as to the matter of evaluating the skill of a nurse, with the method according to Patent Literature 4, a test for measuring skill has to be taken in addition to normal work. This creates a problem in that not only does it impose more of a burden on nurses and the like, but the accuracy of evaluation can also be affected depending on the test problems.

With the method according to Patent Literature 5, the method for time measurement is not discussed, but automatic measurement is difficult. Also, since a one-time result is used to evaluate skill, incidental data can greatly affect the result.

With the method according to Patent Literature 2, the measurement of time is discussed. Nevertheless, this is nothing more than measuring how much time is required for scheduling work, and this is not linked to the skill of the workers. Also, in the time measurement method, the period between arrival and departure is measured. Therefore, a problem is that how long each individual job takes is unknown, and measurement accuracy is also extremely vague.

Also, with the system and method according to Patent Literature 6, even though an in-hospital system is constructed using the same technology as that already being used in the hospital's system, detailed reporting and the like to other healthcare providers still cannot be performed with an existing electronic medical record even with this system.

Also, with the system according to Patent Literature 7, even though it is possible to communicate to the healthcare provider that the scoring engine indicates that there is a patient who may be problematic, just as in Patent Literature 6, detailed reporting and the like to other healthcare providers cannot be performed.

Further, with the method according to Patent Literature 8, data from a device and from a device connected to a medical device can be analyzed. However, how a healthcare provider or the like actually handles the medical device or the device connected to the medical device, and whether or not it the device is being used according to hospital policies and rules and as explained in the manufacturer's instruction manual cannot be confirmed. In other words, with only the data from a medical device, it is impossible to go through an actual PDCA cycle, continue to provide feedback about even everyday work, and improve the system.

Also, with the method according to Patent Literature 9, the only work that can be done is the same as with an electronic medical record that can be used with existing desktop PCs and the like. Therefore, even with a handheld computer with improved portability, a detailed report or the like cannot be given to other medical personnel without markedly increasing the workload of the medical staff.

The function according to Patent Literature 10 does prevent mistakes in ordering. However, when measuring the blood glucose level of a patient a number of times a day, the necessary detailed report about the status of the measurement device and the patient's condition, which can change from one time to the next, cannot be given to other medical personnel without markedly increasing the workload of the medical staff.

With the system according to Patent Literature 11, it is disclosed that the resource status of medical instruments, medical workers, and the like can be adjusted optimally for patient care. However, a problem is that this does not accommodate improvement of skills and higher work efficiency due to training and education of healthcare providers. Furthermore, just as with Patent Literature 8, it is impossible to confirm whether the medical device is being used as described by the manufacturer in accordance with the instruction manual and according to the policies and rules of the hospital.

In other words, with only the data from a medical device, it is impossible to go through an actual PDCA cycle, continue to provide feedback about even everyday work, and improve the system. Therefore, there is not only a problem in that this goes no further than optimizing patient care on the basis of information at the time of data input from a healthcare provider or a medical device, but also withstanding audits by hospital staff or third parties is impossible.

On the other hand, from the viewpoint of the administrative department of a hospital, in addition to general information such as the number of measurements that are provided or displayed by the medical device for normal users and administrators, it is often also necessary to ascertain the skill of the nurses, work efficiency, etc., as well as financial information that is essential for hospital management and is tied to this information. However, the patent literature and non-patent literature introduced so far do not disclose any solutions such as displaying or providing hospital management indices.

The present invention solve the above-mentioned conventional problems, and it is an object thereof to provide biological information measurement device with which the report item about the current measurement can be reliably transmitted at the time of the next measurement to the next measurer.

Solution to Problem

In order to solve the above problem, the biological information measurement device according to the present invention comprises a sensor mounting portion, a measurement component, an identification information reader, a display component, a storage component, a controller, and a report item input component. The controller activates an input screen for inputting the report items on the display component for each measurement at the measurement component, and when the report items are inputted at the report item input component, the controller stores the report items and the identification information associated each other in correspondence with each measurement at the measuring component in the storage component, and when the identification information about the subject is read by the identification information reader, the controller confirms whether or not there are report items on the basis of the information stored in the storage component, and if there are report items, displays them on the display component.

Advantageous Effects

With the biological information measurement device according to the present invention, report items can be reliably transmitted at the time of the next measurement to the next measurer, on the basis of the current measurement.

BRIEF DESCRIPTION OF DRAWINGS

FIG. 21 shows an acquired data list in Embodiment 2 of the present invention;

FIG. 43 shows examples of other useful metric data in Embodiment 2 of the present invention;

FIG. 44 shows examples of using medical data as metric data in Embodiment 2 of the present invention;

FIG. 58 shows a patient satisfaction level input screen in Embodiment 3 of the present invention;

DESCRIPTION OF EMBODIMENTS

Reference Example

Before describing an embodiment of the present invention, an example of a blood glucose measurement device that has been commonly used in the past will be described through reference to FIGS. 16, 17, and 2.

Figure 2:
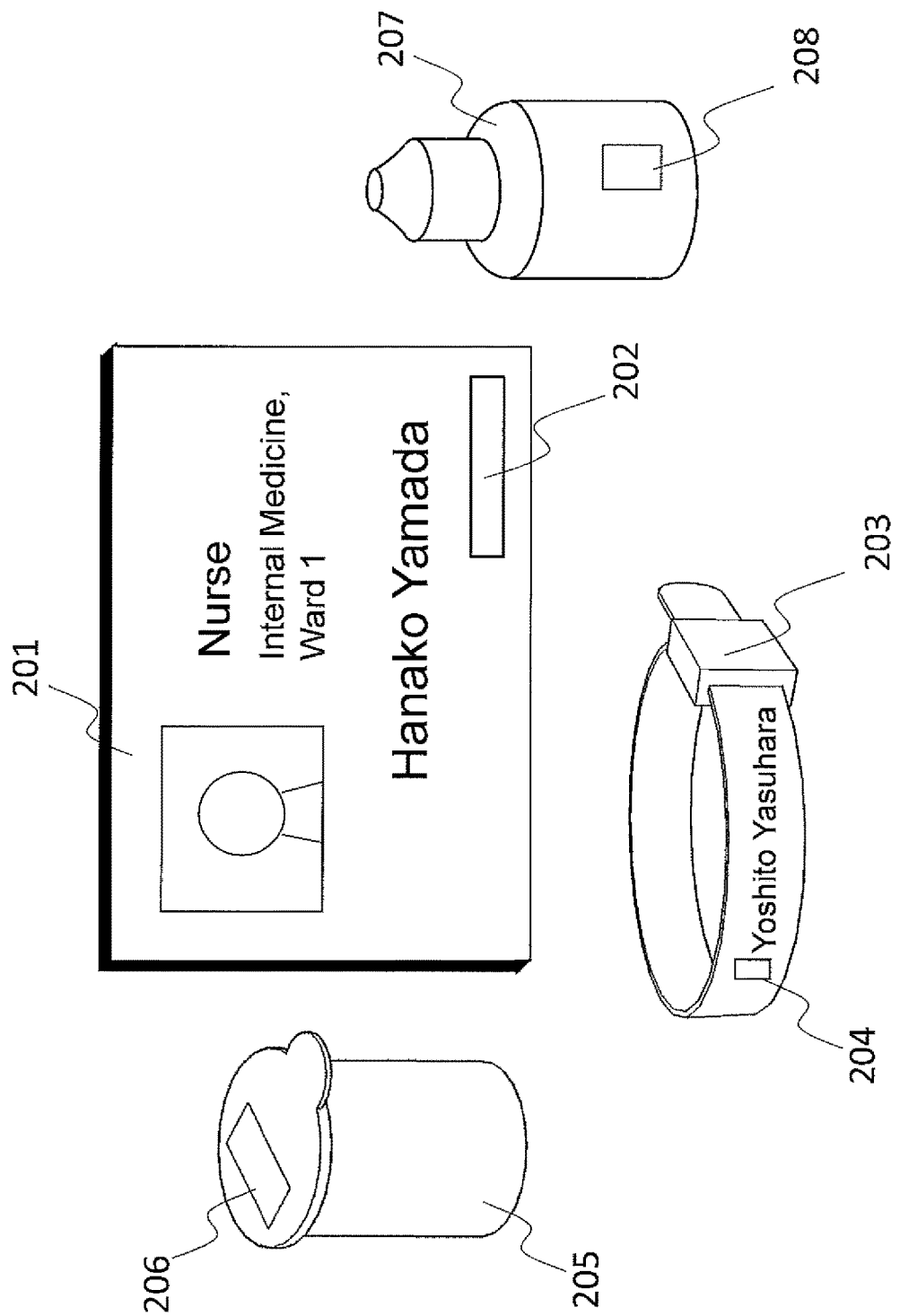
FIG. 2 shows types of barcodes used in hospitals.
Figure 16:
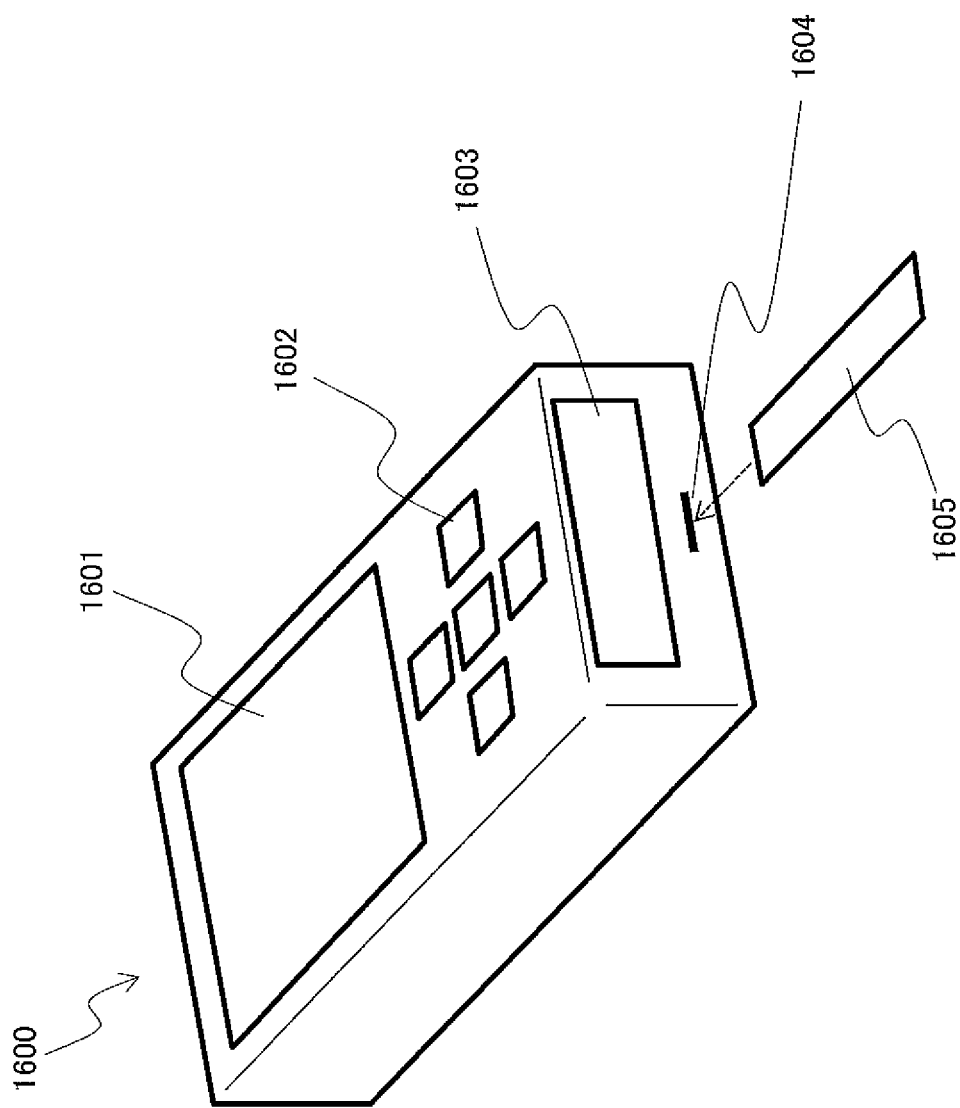
FIG. 16 shows the appearance of a conventional blood glucose measurement device.
Figure 17:
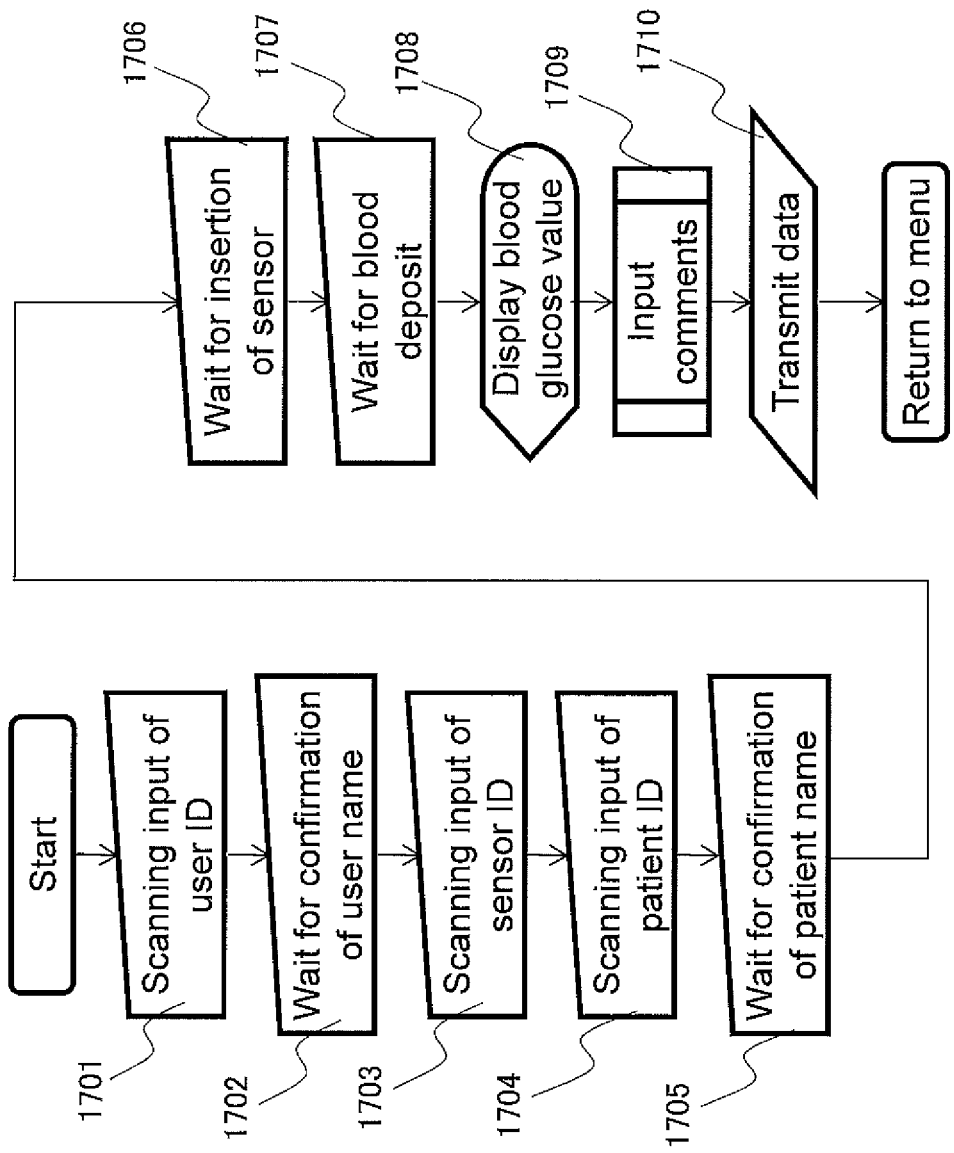
FIG. 17 shows the flow of operation of a conventional blood glucose measurement device.

FIGS. 16 and 17 are diagrams illustrating a conventional blood glucose measurement device, and FIG. 2 is a diagram of various barcodes that are also used with the blood glucose measurement device in this embodiment. That is, FIG. 2 is not a diagram illustrating a conventional configuration.

FIG. 16 is an external view of a conventional blood glucose measurement device. Since this is a blood glucose measurement device intended for use in a hospital, the user is a healthcare provider such as a doctor or a nurse, and the blood glucose level of the patient is measured by the user operation.

In FIG. 16, 1600 denotes the overall blood glucose measurement device.

The blood glucose measurement device 1600 comprises a display screen 1601, an operation button group 1602, a barcode reader 1603, and a sensor strip insertion opening 1604.

When the blood glucose measurement device 1600 is used, the operation button group 1602 is operated in accordance with the menu and instructions displayed on the display screen 1601. In addition, the blood glucose measurement device 1600 uses the barcode reader 1603 as necessary to read the barcode of a patient ID (identification information) attached to the wrist of the patient. Furthermore, the blood glucose measurement device 1600 measures the blood glucose level using blood deposited on a sensor strip 1605 inserted in the sensor strip insertion opening 1604.

In a hospital, patients, nurses, and sensor strips are managed by barcodes as shown in FIG. 2.

In FIG. 2, 201 is a name tag of the user (such as a doctor or nurse), and the portion is a barcode 202 indicating the user ID. 203 is a patient wrist tag, and the portion is a barcode 204 indicating the patient ID. 205 is a bottle of sensor strips 1605, and the 206 portion is a barcode indicating the sensor ID. 207 is a bottle of QC solution, and the 208 portion is a barcode indicating the ID of the QC solution.

The term QC solution refers to a plurality of types of liquid of known concentrations that are periodically measured in place of the patient's blood in order to check whether or not the measurement device and the sensor strips are functioning normally as a system. The QC liquid will be described in detail later on.

The flow of operation of a conventional blood glucose measurement device commonly used in a hospital will now be described through reference to FIG. 17.

In the blood glucose measurement device 1600, when blood glucose is to be measured, the operation button group 1602 is operated on the menu displayed on the display screen 1601, and blood glucose measurement execution is selected.

An instruction to scan the barcode 202 on the name tag of the nurse is displayed on the display screen 1601. Therefore, the nurse (user) points the name card 201 toward the barcode reader 1603 to read the barcode 202. As a result, the blood glucose measurement device 1600 recognizes the user ID (step 1701).

When a user ID has been recognized, the blood glucose measurement device 1600 displays the name of the user corresponding to the user ID on the display screen 1601. The nurse (user) then confirms that the displayed name is his or her name, and uses the operation button group 1602 to input this confirmation (step 1702).

Next, the blood glucose measurement device 1600 displays on the display screen 1601 an instruction to scan the barcode 206 indicating the sensor ID. Upon seeing this, the nurse (user) points the barcode 206 toward the barcode reader 1603 to read the barcode 206. As a result, the blood glucose measurement device 1600 recognizes the sensor ID (step 1703).

Similarly, the blood glucose measurement device 1600 displays on the display screen 1601 an instruction to scan the barcode 204 indicating the patient ID. Upon seeing this, the nurse (user) points the tag 203 toward the barcode reader 1603 to read the barcode 204. As a result, the blood glucose measurement device 1600 recognizes the patient ID (step 1704).

When a patient ID has been recognized, the blood glucose measurement device 1600 displays on the display screen 1601 the name and birth date of the patient corresponding to the patient ID.

The nurse (user) instructs the patient to declare his or her name and birth date. Then, the nurse (user) confirms that what the patient has declared matches what is on the display screen 1601, and uses the operation button group 1602 to input this confirmation (step 1705). This confirmation is an important process in terms of preventing patient misidentification.

Next, in step 1706, an instruction to insert a sensor strip 1605 into the sensor strip insertion opening 1604 is displayed on the display screen 1601.

Next, when the nurse (user) inserts the sensor strip 1605 into the sensor strip insertion opening 1604, an instruction to deposit blood on the sensor strip 1605 is displayed on the display screen 1601 in step 1707.

Next, the nurse (user) pricks the fingertip of the patient with a needle, and when a drop of blood has appeared on the fingertip, it is deposited on the sensor strip 1605.

When blood is deposited on the sensor strip 1605, the blood glucose measurement device 1600 measures the blood glucose level in the blood, and in step 1708 the measurement result is displayed on the display screen 1601 and the nurse (user) is instructed to select a comment.

In step 1709, the nurse (user) uses the operation button group 1602 to select a comment to be left, from among the comment options listed on the display screen 1601.

Here, a plurality of options are readied as the comments that are listed, such as "had to squeeze out blood because of low volume," or "patient had a snack just before blood sampling."

After the comment selection has been completed in step 1709, the blood glucose measurement device 1600 uses a built-in communication function to transfer the data to a terminal in a clinical laboratory.

In addition to the blood glucose measurement result, data that is transferred may also include the measurement date and time, the user ID, the sensor ID, the patient ID, comments, and so forth, all of which are sent together.

The data can be reviewed by the person in charge of the testing department on the laboratory terminal. The person in charge of the testing department checks the individual data and records data that is judged to be reliable in the patient's electronic medical record.

Also, if, for example, the blood glucose level of the patient is lower than usual and there is a comment that "had to squeeze out blood because of low volume," the blood glucose measurement device 1600 mixes interstitial fluid into the blood sample that was squeezed out, and concludes that there is a possibility that the blood glucose level was evaluated to be low. The blood glucose measurement device 1600 may then discard this measurement result and instruct the user to take another measurement, for example.

Comments are also sent to the electronic medical record. Therefore, even when the blood glucose level is high, for example, if there is a comment indicating that the patient snacked immediately before the blood collection, the doctor can make a diagnosis that takes this into account.

As described above, the comment selected by the nurse (user) is used as important report information in evaluation by a doctor or the person in charge of the testing department.

An example of a blood glucose measurement device that has been commonly used in the past was described above, but now embodiments of the present invention for solving conventional problems will be described.

Embodiment 1

The configuration of the blood glucose measurement device (biological information measurement device) pertaining to an embodiment of the present invention will now be described through reference to FIGS. 1 to 15 and FIG. 63.

Figure 1:
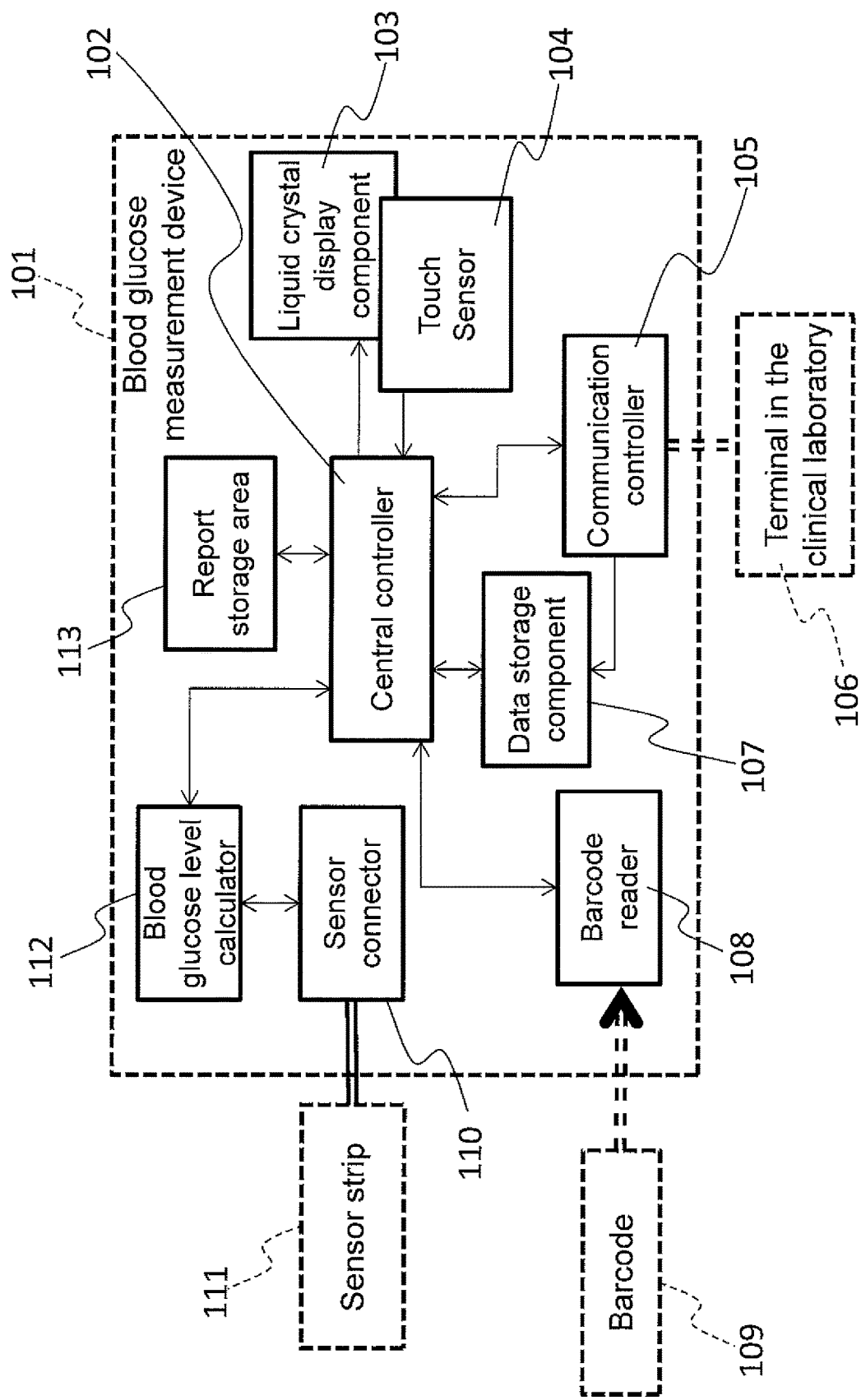
FIG. 1 is a system configuration diagram of a blood glucose measurement device according in Embodiment 1 of the present invention.

FIG. 1 is a diagram of the system configuration of the blood glucose measurement device (biological information measurement device) pertaining to this embodiment.

A blood glucose measurement device will be described below as an example of the biological information measurement device in this embodiment. However, the present invention is not limited to a blood glucose measurement device. For example, it can be applied to any of various kinds of blood testing equipment, urine testing equipment, or other such measurement devices that are used by a doctor, a nurse, or the like to perform a tests on a patient.

In FIG. 1, 101 denotes the blood glucose measurement device of this embodiment. In the blood glucose measurement device 101, 102 is a central controller (controller) that performs all of the processing.

The central controller 102 is connected to a liquid crystal display component 103 for displaying information to the user, and a touch sensor (report item input component) 104 for inputting instructions from the user.

The liquid crystal display component (display component) 103 and the touch sensor 104 are disposed overlapping, operate as a touch panel, and serve as a man-machine interface from the user in the blood glucose measurement device 101.

In this embodiment, a configuration in which a touch panel is used as a man-machine interface is described, but the same effect can be obtained when an input button is used instead of a touch panel.

Also, the blood glucose measurement device 101 has a communication controller 105, which allows for communication with a terminal 106 in a clinical laboratory of a hospital. The latest data for the patient and the user in the terminal 106 of the clinical laboratory is stored in a data storage component (storage component) 107 in the measurement device via the communication controller 105.

Patient data includes, for example, a list of patient IDs, as well as the names, sexes, and birth dates associated with those IDs. The user data is, for example, a list of user IDs and the names and passwords associated with those IDs.

The blood glucose measurement device 101 has a barcode reader (identification information reader) 108. The barcode reader 108 reads a barcode 109 attached to a patient's wrist, a user's name tag, etc., and sends the ID to the central controller 102.

Upon receiving the ID, the central controller 102 refers to the data tied to the ID and stored in the data storage component 107. For example, when the barcode of a patient ID is read by the barcode reader 108, the central controller 102 retrieves from the data storage component 107 the patient name, sex, and birth date associated with the ID that was read. This makes it possible to learn the patient's name, sex, and date of birth from the barcode on the patient's wrist.

The blood glucose measurement device 101 comprises a sensor connector (sensor mounting portion) 110. A sensor strip (sensor) 111 is inserted into the sensor connector 110.

Blood is then deposited on the sensor strip 111 inserted into the sensor connector 110. This produces a voltage signal corresponding to the blood glucose level. This voltage signal is then read by a blood glucose level calculator (measurement component) 112 via the sensor connector 110, and the blood glucose value found by the blood glucose level calculator 112 is sent to the central controller 102.

The function of the blood glucose level calculator 112 can also be performed inside the central controller 102. In this case, the central controller 102 performs the actual calculation of the blood glucose level from the voltage.

113 is a report storage area, which is one of the main features of this embodiment. The report storage area (storage component) 113 is an area for storing report items to be transmitted to the user who performs the next measurement, and will be described in detail below.

Although the report storage area 113 is depicted independently in this embodiment, the report storage area report storage area 113 may be provided inside the data storage component 107.

The barcode shown in FIG. 2 is the same as what was described in the reference example above, and what is currently in use in hospitals can be used without modification.

Figure 3:
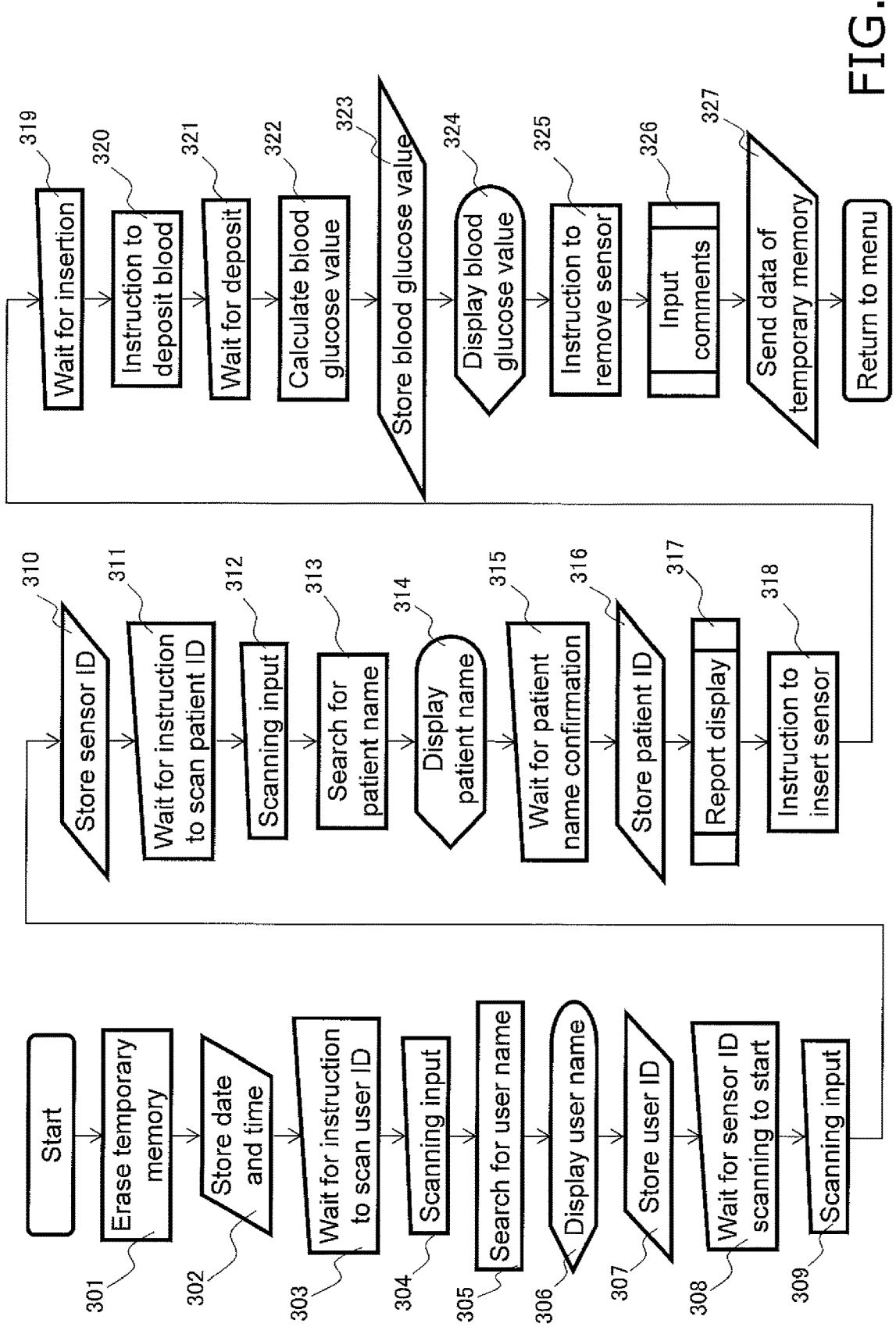
FIG. 3 shows the processing flow of the blood glucose measurement device in Embodiment 1 of the present invention.

FIG. 3 is a flowchart showing the flow of processing when the blood glucose measurement device 101 measures the blood glucose level of a patient. In the above-mentioned reference example, FIG. 17, which illustrates prior art, does not show the processing inside the measurement device for the sake of simplifying the description, but in FIG. 3, the processing details, including internal processing, is shown in detail.

Also, in FIG. 3, the main features of this embodiment are step 317 and step 326. Therefore, these will be discussed in detail in the following explanation.

When the user instructs the blood glucose measurement device 101 to start measurement, in step 301, the temporary memory in the data storage component 107 is erased. The temporary memory is an area for temporarily holding the result for one measurement and any information that is attached to it. The data in the temporary memory is sequentially stored in the course of a single measurement process, and is finally transmitted through the communication controller 105 to the terminal 106 in the clinical laboratory.

Next, in step 302, the current date and time representing the measurement time are stored in the temporary memory. The current date and time are acquired from a clock (not shown) built into the blood glucose measurement device 101. The current date and time may be acquired from the terminal 106 in the clinical laboratory via the communication controller 105.

In the step 303, an instruction to scan the barcode 202 of the user ID is displayed on the liquid crystal display component 103, and the barcode reader 108 is activated.

In step 304, if holds up the barcode 202 to the blood glucose measurement device 101, the barcode reader 108 reads the user ID and sends it to the central controller 102.

In step 305, the central controller 102 refers to the data storage component 107 and searches for the name of the user corresponding to the user ID.

In step 306, the user name that was found is displayed on the screen, and the user confirms this.

In actual processing, if the barcode reader cannot read the barcode, if there is no user ID in the data storage component 107 corresponding to the user ID that was read, etc., processing corresponding to the error will be necessary. However, for the sake of simplicity, the description of the error processing, will be omitted here and below.

In step 307, when the user confirms that his or her name is correctly displayed, that user ID is stored in the temporary memory.

In step 308, an instruction to scan the barcode 206 of the sensor ID is displayed on the liquid crystal display component 103, and the barcode reader 108 is activated.

In step 309, when the user holds up the barcode 206 to the blood glucose measurement device 101, the barcode reader 108 reads the sensor ID.

In step 310, the sensor ID is stored in the temporary memory.

In step 311, an instruction to scan the barcode 204 of the patient ID is displayed on the liquid crystal display component 103, and the barcode reader 108 is activated.

In step 312, when the user holds up the barcode 204 to the blood glucose measurement device 101, the barcode reader 108 reads the patient ID and sends it to the central controller 102.

In step 313, the central controller 102 refers to the data storage component 107 and searches for the name, sex, and birth date for the patient corresponding to the patient ID.

In step 314, this information is displayed on the screen, and the user confirms the information.

In step 315, the user gives an instruction to the patient to verbally state his or her name, sex, and birth date, and confirms that the details thereof match the information displayed on the screen. This step involves processing for preventing misidentification of a patient.

If confirmation is made in step 315, in step 316 the patient ID is stored in the temporary memory.

In step 317, a report is displayed, which is one of the main features of this embodiment. The system by which the report items are displayed will be described below.

The display of the report here is done as follows. First, a search is made to see whether or not report items from the previous user for a given patient is in the report storage area 113, and if report items are found, then the content of the report is displayed on the liquid crystal display component 103.

The report items that are stored in the report storage area 113 are, for example, comments and other such information stored as transmission details that are important for a patient A, a patient B, and a patient C. The report items include information inputted in step 326 (discussed below), information inputted and edited at the terminal 106 of the clinical laboratory, and so forth.

Specifically, in this embodiment the term "report items" refers, for example, to information that is to be transmitted by the nurse or other user who measured the blood glucose level for patient A the last time, or by the POCC (point of care coordinator) of the clinical laboratory, to the nurse, etc., who will perform measurement for the same patient A the next time.

If, for example, no comments that correspond to the patient ID have been stored in the report storage area 113, such as during measurement on the first visit of a patient, step 317 may be skipped, and the flow may move on to step 318 in which the user is prompted to insert the sensor strip 111.

After the user has confirmed the content of the report, in step 318, an instruction to insert a sensor strip 111 into the sensor connector 110 is displayed on the liquid crystal display component 103.

In step 319, the system goes into standby mode until the sensor strip 111 is inserted into the sensor connector 110.

In step 320, when a sensor strip 111 is inserted, an instruction prompting the user to deposit the patient's blood on the sensor strip 111 is displayed on the liquid crystal display component 103.

In step 321, the system goes into standby mode until blood is deposited on the sensor strip 111.

In step 322, when blood is deposited on the sensor strip 111, the blood glucose level is calculated by the blood glucose level calculator 112. Here, the calculated blood glucose level is stored in the temporary memory in step 323, and is displayed on the liquid crystal display component 103 in step 324.

In step 325, an instruction prompting the user to remove the sensor strip 111 for which the measurement of blood glucose level has been completed from the sensor connector 110 is displayed on the liquid crystal display component 103.

In step 326, the user inputs comments related to this measurement. Here, designating a report, which is one of the main features of this embodiment, is performed in addition to comment input.

The inputted comment is stored in the temporary memory, and the comment designated for report is stored in the report storage area 113 along with the patient ID.

Also, comment input is selected from a previously prepared list of comments, which will be described in detail below. This comment list is produced at the terminal 106 in the clinical laboratory, and is stored in the data storage component 107 via the communication controller 105.

In step 327, all the data stored in the temporary memory by the above processing is sent through the communication controller 105 to the terminal 106 in the clinical laboratory.

Figure 15:
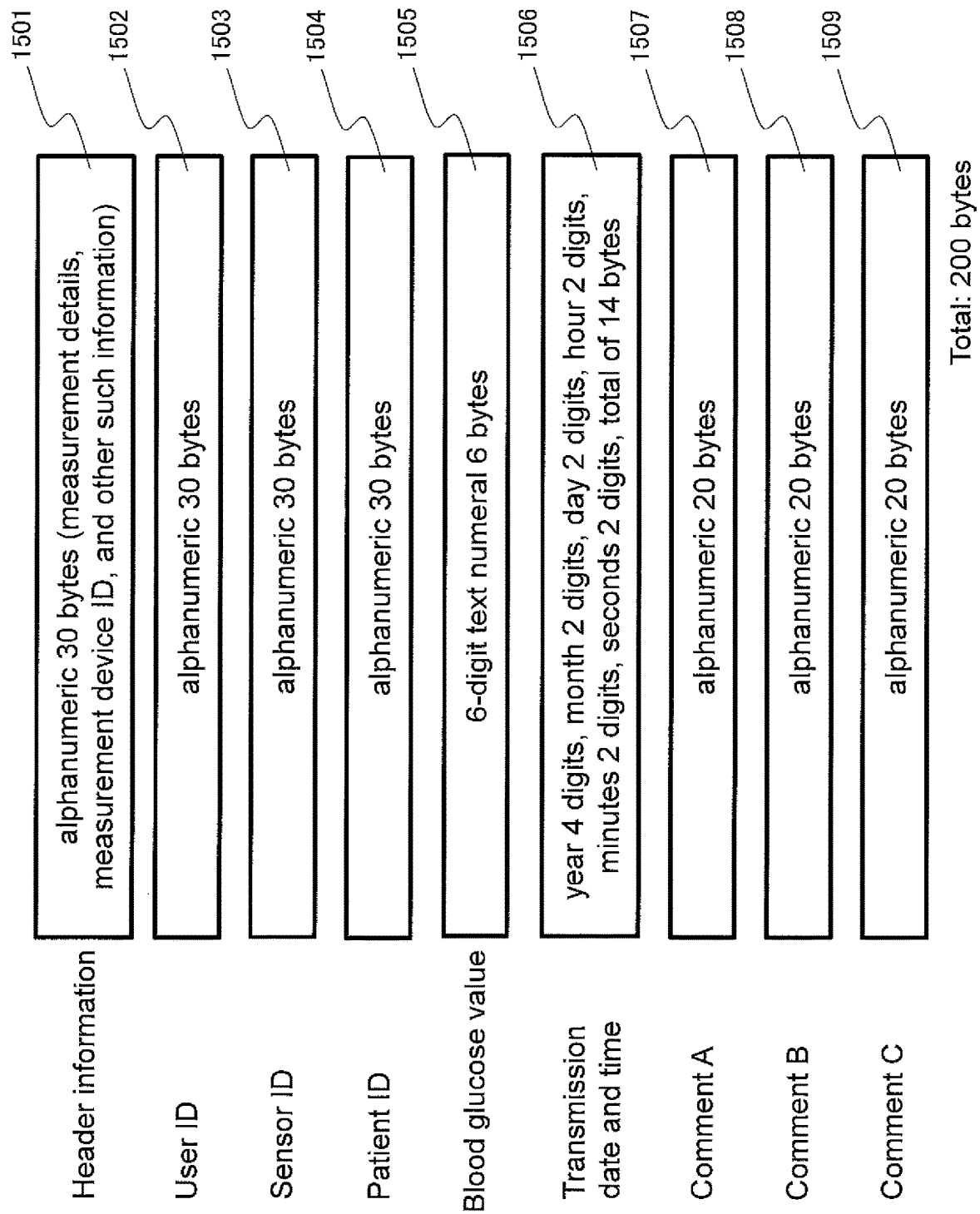
FIG. 15 shows the data format of a temporary memory in Embodiment 1 of the present invention.

FIG. 15 shows an example of the data format of the temporary memory to be sent to the terminal 106 in the clinical laboratory in step 327 in FIG. 3.

In FIG. 15, header information 1501 includes basic information such as that it is blood glucose that is being measured, or the ID of the measurement device. A user ID 1502 indicates the ID of the measurement user stored in step 307. A sensor ID 1503 indicates the ID of the sensor used in the measurement stored in step 301. A patient ID 1504 is the ID of the measured patient stored in step 316. A blood glucose value 1505 is a measurement result, and is what is stored in step 323. A transmission date and time 1506 are the date and time of the measurement, and are what is stored in step 302.

Comments A 1507 to comments C 1509 represent the comments selected in step 325 and stored respectively. The method for selecting the comments will be described below.

This format itself is the same as in prior art, so the communication software currently being used in the hospital may be used without modification.

Figure 4:
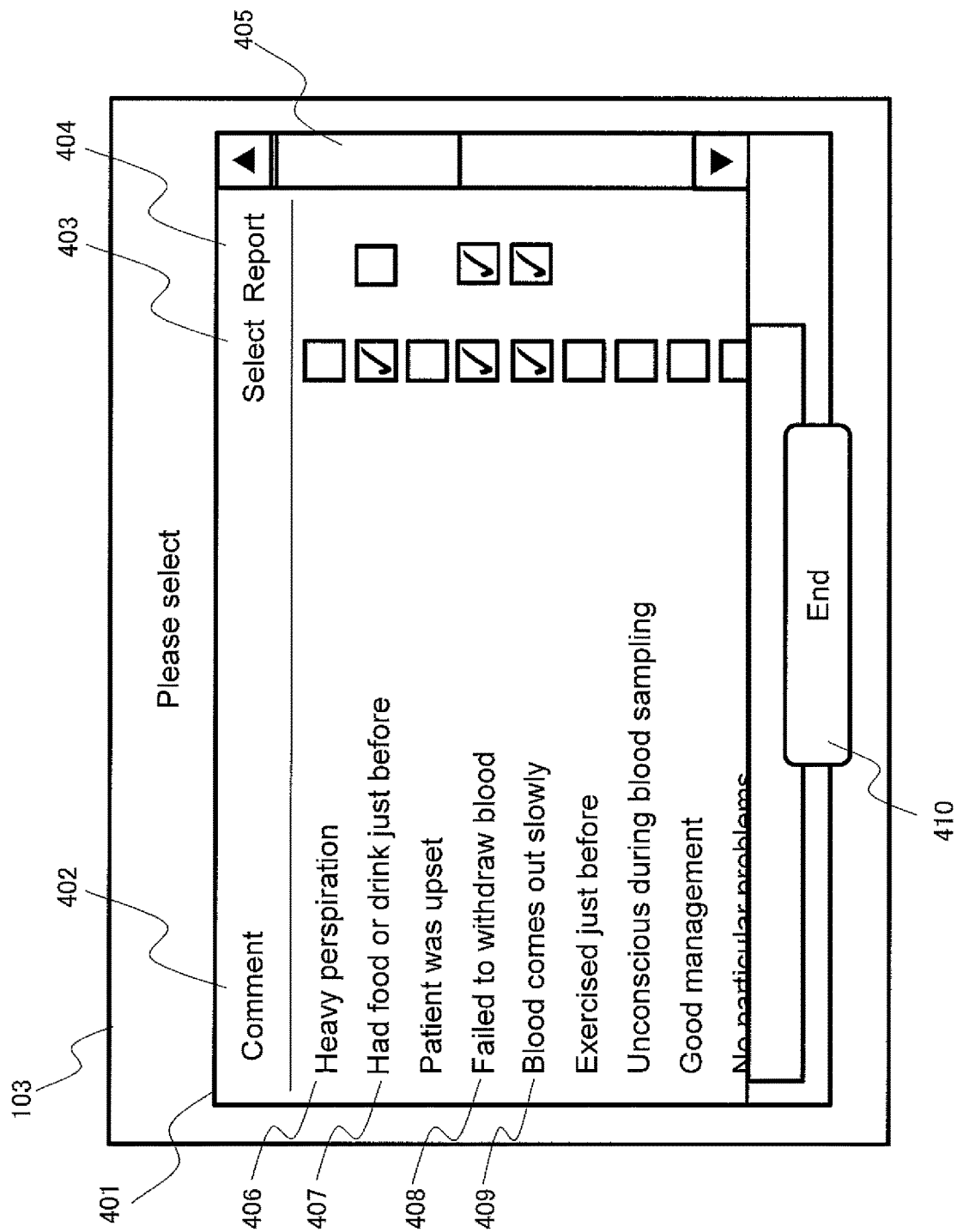
FIG. 4 shows a comment selection screen in Embodiment 1 of the present invention.

Next, this embodiment when a comment is inputted in step 325 of FIG. 3 will be described through reference to FIG. 4. FIG. 4 shows the screen displayed on the liquid crystal display component 103 in the comment input step 325.

At this point, a comment selection list 401 is displayed on the screen (input screen) of the liquid crystal display component 103. The user first selects a comment to be sent to the terminal of the clinical laboratory (POCC) along with the measurement result, from the list shown here.

In addition to a comment content column 402 and a comment selection column 403, a report designation column 404, which is one of the main features of this embodiment, is disposed in the comment selection list 401. There are many comment options, and if they do not all fit on the screen, a scroll bar 405 can moved up and down to see the parts that are not displayed.

A plurality of previously prepared comments contents are displayed in the comment content column 402. Selection check boxes corresponding to these comments are provided to the right of the comment content column 402. The boxes can be checked or unchecked by tapping the screen at the portions with the selection check boxes.

In the initial state, all of the boxes are unchecked, and the user checks off those boxes to be selected as comments.

A space for displaying check boxes for report designation, which is one of main features of this embodiment, is provided to the right of the selection check boxes. In this space are displayed check boxes for reporting only those comments for which the selection check boxes have been checked.

For example, in this embodiment, the comment 406 is not selected. Accordingly, no check box for report designation is displayed in the report designation column 404.

On the other hand, for the comments 407, 408, and 409 for which the selection check boxes have been checked, check boxes for report designation are displayed in the report designation column 404.

Just as with the selection check boxes, the check boxes for report designation can be checked or unchecked by tapping portion of the screen with the check boxes for report designation. Accordingly, the user selects a comment to be reported and checks that box.

For a comment already selected as a report comment at the time of the last measurement, a check box may be displayed in the space of the report designation column 404 from the outset, regardless of whether or not the selection check box was checked at the time of the current measurement.

As described above, in this embodiment, the comments 407, 408, and 409 are sent to a terminal in a clinical laboratory (POCC), and of these, the comments 408 and 409 are used as report items.

An upper limit may be provided for the number of selections in the comment selection list 401. In this case, for example, the settings may be such that up to three selection check boxes can be checked, and up to two report designation check boxes can be checked. At this time, if the user attempts to check more than the above numbers, the tap operation for those checks will be ignored.

When the user finishes making his or her selections in the comment selection list 401, the end button 410 is tapped, and the flow proceeds to the next step.

In this example, only the selected report check boxes are displayed. However, as another display method, it is also possible to display all of the report check boxes in advance, and automatically check a selection check box when a report check box has been checked.

Furthermore, the approach so far has been premised on the fact that report comments are always included in selection comments. However, if these are independent, the configuration may be such that both check boxes can be checked completely independently. Also, the display of the report designation column 404 may be omitted, and all of the comments selected in the comment selection column 403 may be used as report comments.

Figure 5:
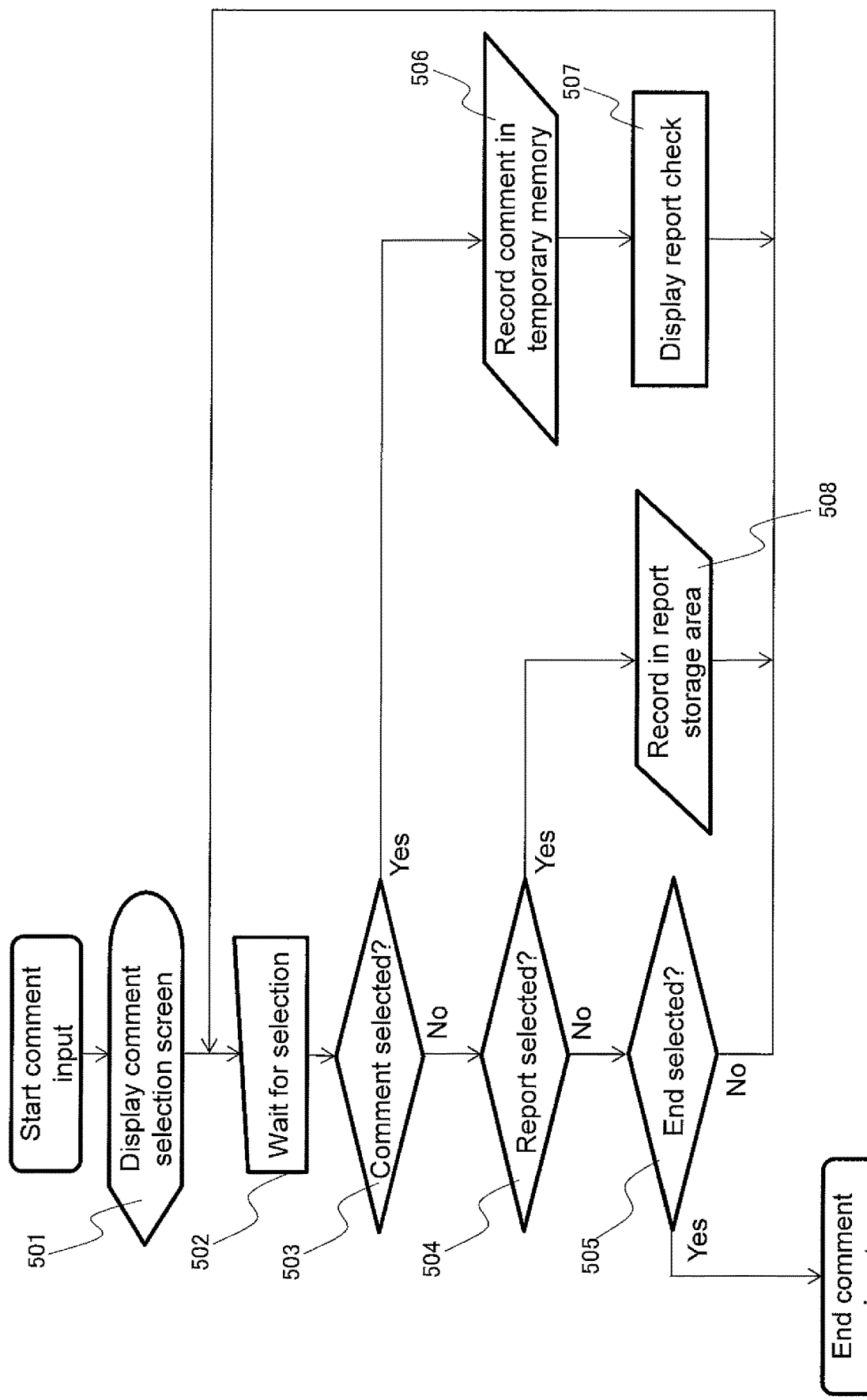
FIG. 5 shows the flow of comment input in Embodiment 1 of the present invention.

Next, processing inside the blood glucose measurement device 101 when the comment selection list 401 is displayed will be described through reference to FIG. 5. FIG. 5 is a flowchart showing details of the comment input step 325. What happens in steps 507 and 508 is one of the main features of this embodiment.

In FIG. 5, for the sake of simplicity, only the processing when a check box is checked will be described, and the processing when a box is unchecked will be omitted.

In the comment input step, first, in step 501, the comment selection list 401 in FIG. 4 is displayed in a state in which all of the boxes are unchecked.

While waiting for input in step 502, the system is on standby until some point on the screen is touched by the user. Here, when the screen is touched, first, in step 503, the system checks whether or not a comment selection check box has been tapped.

If a comment selection check box has not been tapped, then in step 504 the system checks whether or not a report check box has been tapped.

If a report check box has not been tapped, the system then checks whether or not the end button 410 has been tapped. Here, if the end button 410 has been tapped, the processing is ended, and otherwise the flow goes back to the selection waiting step 502 to wait for input.

In step 503, if a comment selection check box has been tapped, the comment selected in step 506 is recorded in the temporary memory. After this, in step 507, a report check box corresponding to that comment is displayed, and the flow goes back to the selection waiting of step 502.

In step 504, if a report check box has been tapped, the comment selected in step 508 is recorded in the report storage area 113.

Figure 6:
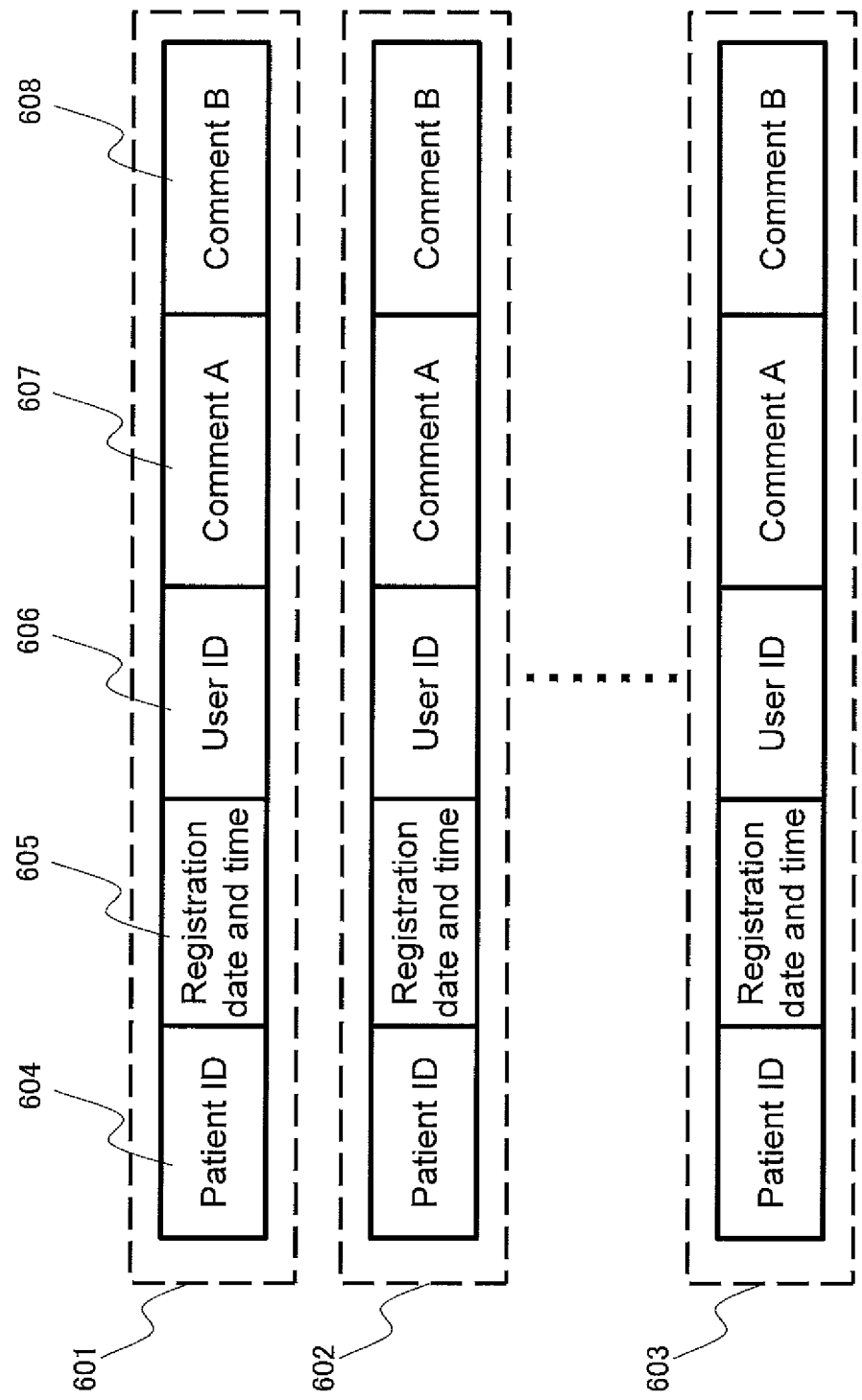
FIG. 6 shows the data structure of a report storage area in Embodiment 1 of the present invention.

FIG. 6 shows the data format of the report storage area 113. Having this data is itself one of the main features of this embodiment.

The report storage area 113 stores a plurality of sets of report data created at the time of each measurement, and areas 601, 602, and 603 are created for the respective single measurements.

The area 601 holds the report data produced during measurement of a first patient. The area 601 is made up of an area 604 that holds the ID of the patient to be measured, an area 605 that holds the measurement date and time, an area 606 that holds the user ID of the person selecting the report comment, an area 607 that holds one report comment A, and an area 608 that holds two report comments B.

When the comment input step 325 is commenced, the ID of the patient currently being measured, the measurement start time, and the user ID being used are written in the areas 604, 605, and 606, respectively.

After this, as shown in FIG. 5, the comment selected in step 506 is written in the area 607. If a comment has already been written in the area 607, then the new comment is written in the area 608 corresponding to the comment B.

At the point when the comment input step 325 ends, if no comment has been written in the area 607, that is, if no report comment has been selected, the areas 607 and 608 may be left blank. However, in order to save memory, the entire area 601 for report data area may be erased.

Likewise, the area 602 for report data is created when measuring a second patient, and report data continues to be produced in the area 603 during measurement of the nth patient.

Next, the display format of the report information in step 317 of FIG. 3 will be described through reference to FIG. 7.

Figure 7:
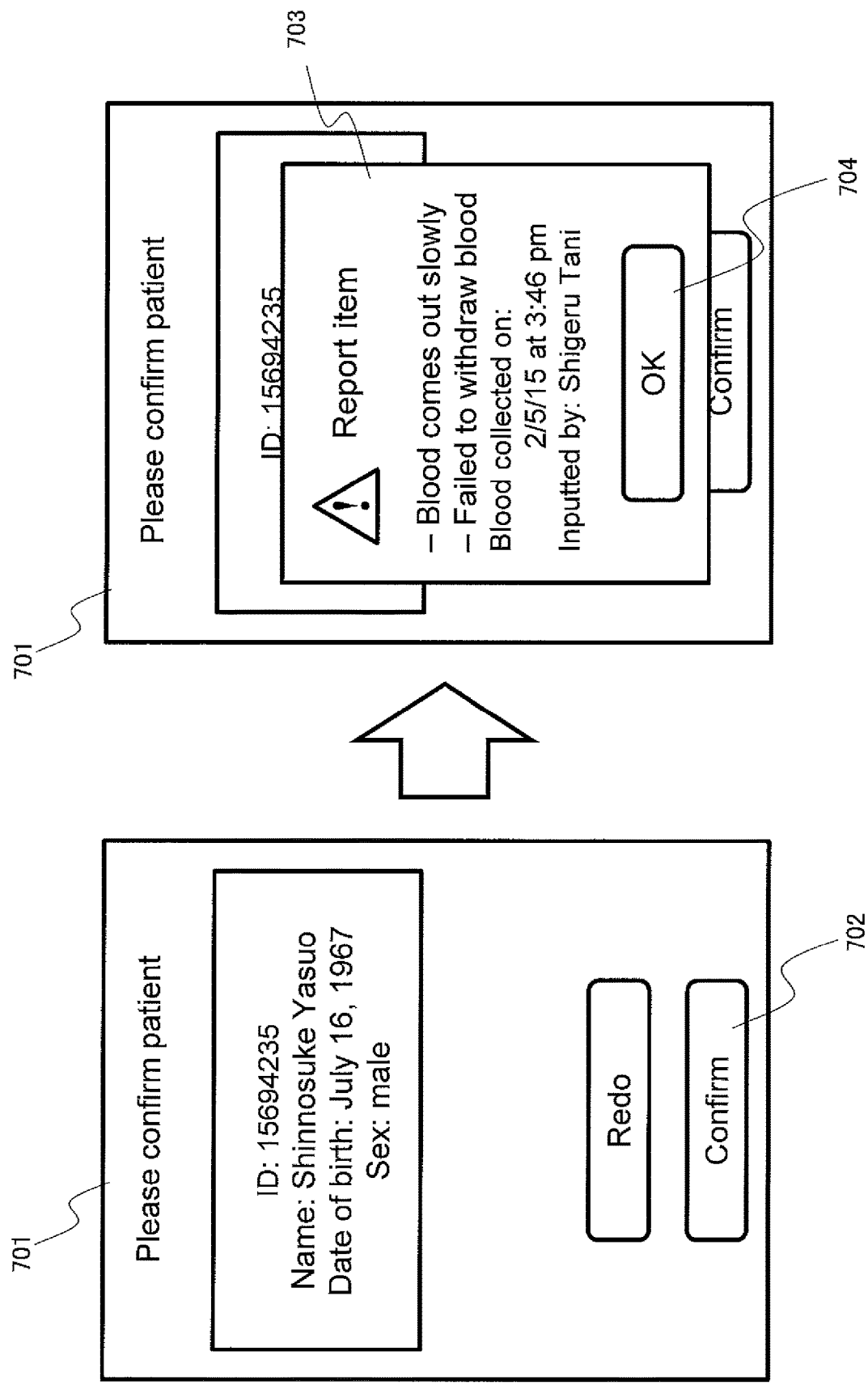
FIG. 7 shows a report comment confirmation screen in Embodiment 1 of the present invention.

FIG. 7 is a diagram illustrating how report comments are displayed.

701 on the left side of the drawing is the patient confirmation screen displayed in step 314.

When the patient is confirmed in step 315 and the confirmation button 702 is tapped, the patient ID is stored in step 316. After this, in step 317 of making a report, the display screen of the liquid crystal display component 103 changes to the screen on the right in the drawing.

This screen is displayed over a patient confirmation screen 701 on the left in the drawing, and a report comment confirmation screen 703 is displayed as a pop-up screen.

On this report comment confirmation screen 703 are displayed the report contents defined by step 325 in the previous measurement for this patient, and the date and time of the previous measurement.

The report contents are confirmed by the user, which makes it possible to employ the appropriate measures for reliably taking a blood sample, such as selecting a puncture instrument with a thick needle, on the basis of a report telling that "blood comes out slowly." As a result, the burden on the patient can be reduced.

Also, upon reading a report of "failed to withdraw blood," the nurse can tell the patient "It looks like we weren't successful last time. Sorry about that." This contributes to a smoother relationship with patients.

Here, report comments, the name of the previous blood sampler, and the date and time when blood was sampled last time were given as information on the report comment confirmation screen 703, but the previous measurement result may be displayed here. In that case, the measurement result may be stored as well in the report storage area 113.

Also, being important matters to be conveyed, the comments designated for report (report items) are preferably displayed in a different format from that of other information (measured values). For example, they may be highlighted with a fluorescent color or the like, or the text of comments designated for report may be displayed in a conspicuous manner, such as using a color that is different from that of the text indicating other information, boldface, or the like.

This allows comments (report items) that are important matters to be conveyed to be reliably transmitted to the user who performs the next measurement.

When the user confirms the report comment confirmation screen 703 and taps the OK button 704, step 317 for displaying the report comes to an end.

Figure 8:
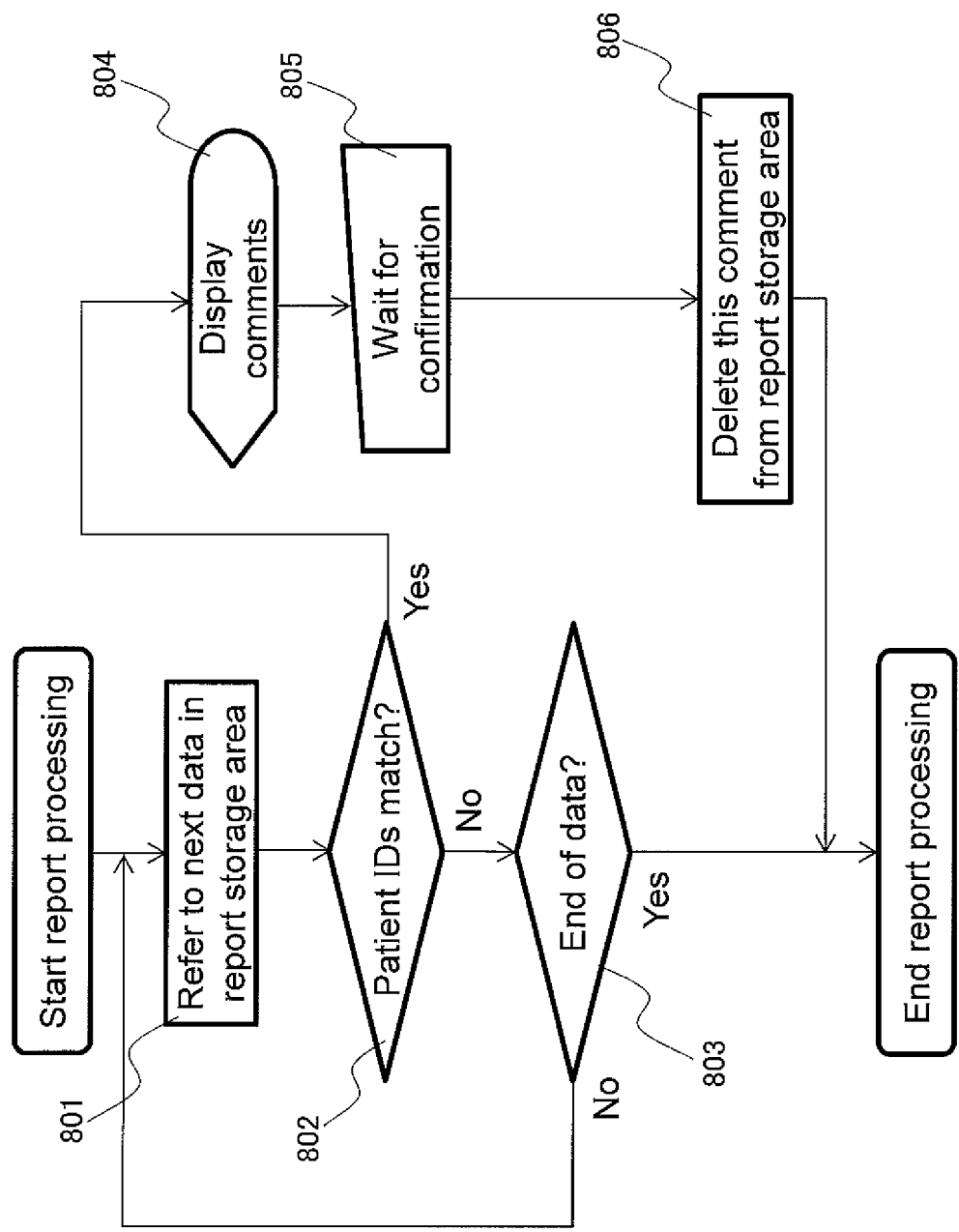
FIG. 8 shows the flow of report processing in Embodiment 1 of the present invention.

FIG. 8 is a flowchart of the details of the processing in step 317 for displaying a report.

In FIG. 8, in step 801, the focus is on the report data for the first person stored in the area 601 in the report storage area 113.

In step 802, the patient ID 604 of the report data for the first person in the area 601 is compared to see if it matches the patient ID currently being measured. If they do not match, in step 803 the system checks whether or not all the report data has been confirmed.

If there is still data remaining, the flow goes back to step 802, and the processing is repeated by focusing on the data for the second person stored in the area 602.

As a result of this repetition, if there is no match between the patient IDs in step 802 by the time the last data has been deemed to be reached in step 803, there is no report for the patient currently being measured. Therefore, in this case, the report comment confirmation screen 703 is not displayed and step 317 is concluded.

On the other hand, in step 802, if the patient ID 604 of the report data for the first person in the area 601 matches the ID of the patient currently being measured, the report comment confirmation screen 703 is displayed in step 804.

The report comments displayed on the report comment confirmation screen 703 come from the areas 607 and 608 where the report comments A and B are held, the comment input date and time come from the area 605, and the comment inputter retrieves the necessary information from the area 606, which can be displayed on a pop-up screen (the report comment confirmation screen 703) shown in FIG. 7.

After the comment display in step 804, the system goes into standby mode and waits for confirmation in step 805.

Here, when the user taps the OK button 704, the flow goes to step 806, and the report data for the first person used in the display from within the report storage area 113 is erased from the area 601.

Next, in the description so far through reference to FIG. 4, an example was given in which the user designates a report comment for each measurement. Now, through reference to FIG. 9, an example will be given of a case in which an administrator designates in advance what parts of the comment list are to be used as report comments, and there is no need for the user to designate report comments.

Figure 9:
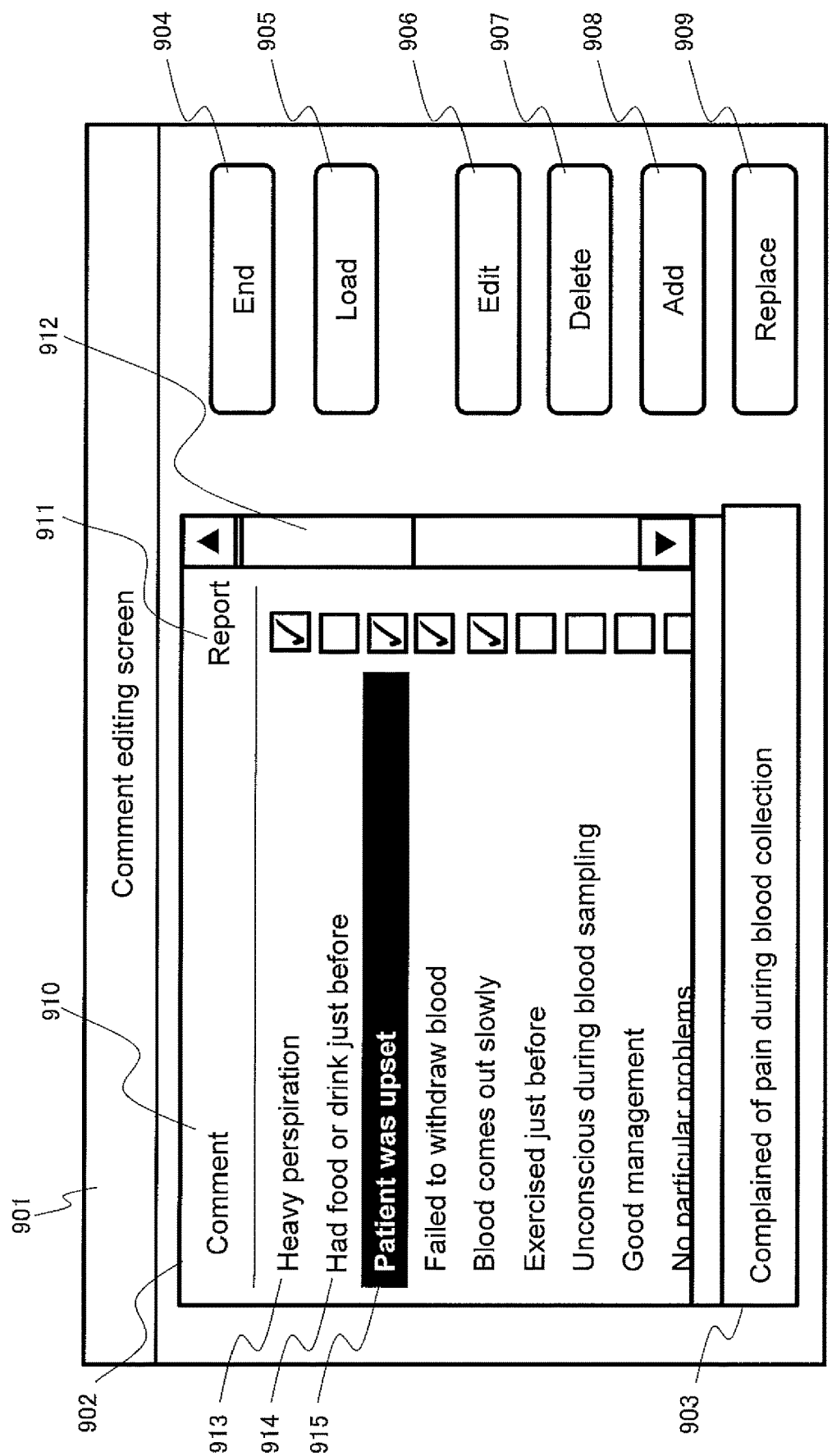
FIG. 9 shows a comment editing screen used on a laboratory terminal in Embodiment 1 of the present invention.

FIG. 9 shows a comment editing screen when editing a comment list on the terminal 106 of the clinical laboratory.

A comment list display component 902, a comment editing component 903, and button groups 904 to 909 are displayed on the comment editing screen 901.

The operation on this screen is performed by the administrator who manages the measurement devices in the hospital.

A comment content column 910 in which a list of comments is displayed and a report designation column 911 are disposed in the comment list display component 902. If there are so many comments that they will not fit on the screen, the parts that are not displayed can be seen by moving the scroll bar 912 up and down.

When the administrator creates this comment list, after entering one comment in the comment editing component 903, each time a comment addition button 908 is clicked on, one edited comment is added to the comment list display component 902.

One of the comments is selected by clicking on a comment in the comment list display component 902.

The selected comment undergoes black and white inversion to indicate that it has been selected. In FIG. 9, the comment 915 has been selected, and this comment is displayed with black and white inverted.

In this state, when the administrator clicks on a comment delete button 907, the selected comment 915 is deleted.

Also, when the comment editing button 906 is clicked on with the comment 915 selected, the selected comment (in this case, "patient was upset") is displayed in the comment editing component 903, and now this comment can be edited.

If a comment replacement button 909 is clicked on after editing, the currently selected comment 915 is replaced with the edited comment. Also, if the comment addition button 908 is clicked on after editing, the currently selected comment 915 remains as it is, and the edited comment is newly added to the list.

There is a report designation column 911 in the comment list display component 902, and a check box is displayed at a position corresponding to each comment.

For example, with the comment 913, it is necessary be careful so that if a patent perspires heavily, the perspiration will not be mixed in with the blood during collection and affect the measurement value, and because this is something that should be reported, the administrator checks the box.

With the comment 914, the fact that the patient had food or drink immediately before measurement, which can lead to a high blood glucose level, is left as a comment. This is information that is necessary for data analysis and diagnosis, and is not information to be conveyed to the user during the examination, so the administrator does not check this box.

Furthermore, with comment 915, if the patient has become upset, care must be taken during the next examination and an apology given or other such action taken, so the administrator checks the box.

The same applies to all of the comments, with comments that need and do not need to be reported to the user who will perform the next measurement for the same patient being classified by either checking or not checking the box.

Upon completion of all comment list creation and report selection, the end button 904 is clicked on, so that the results are saved as a comment list file, which is transmitted from the terminal 106 of the clinical laboratory to the blood glucose measurement device 101, and stored in the data storage component 107 by the communication controller 105.

It is also possible to designate and load a previously stored comment list by clicking on a comment list loading component 905.

With this method, information about whether or not to use a comments for a report is provided to the comment list stored in the data storage component 107 of the blood glucose measurement device 101. Therefore, the user does not need to select a report comment. The comment input screen in this case is in a state in which there is no report designation column 404 in FIG. 4. The user taps the check-list of the comment selection column 403 to perform an operation of merely selecting a comment.

Figure 63:
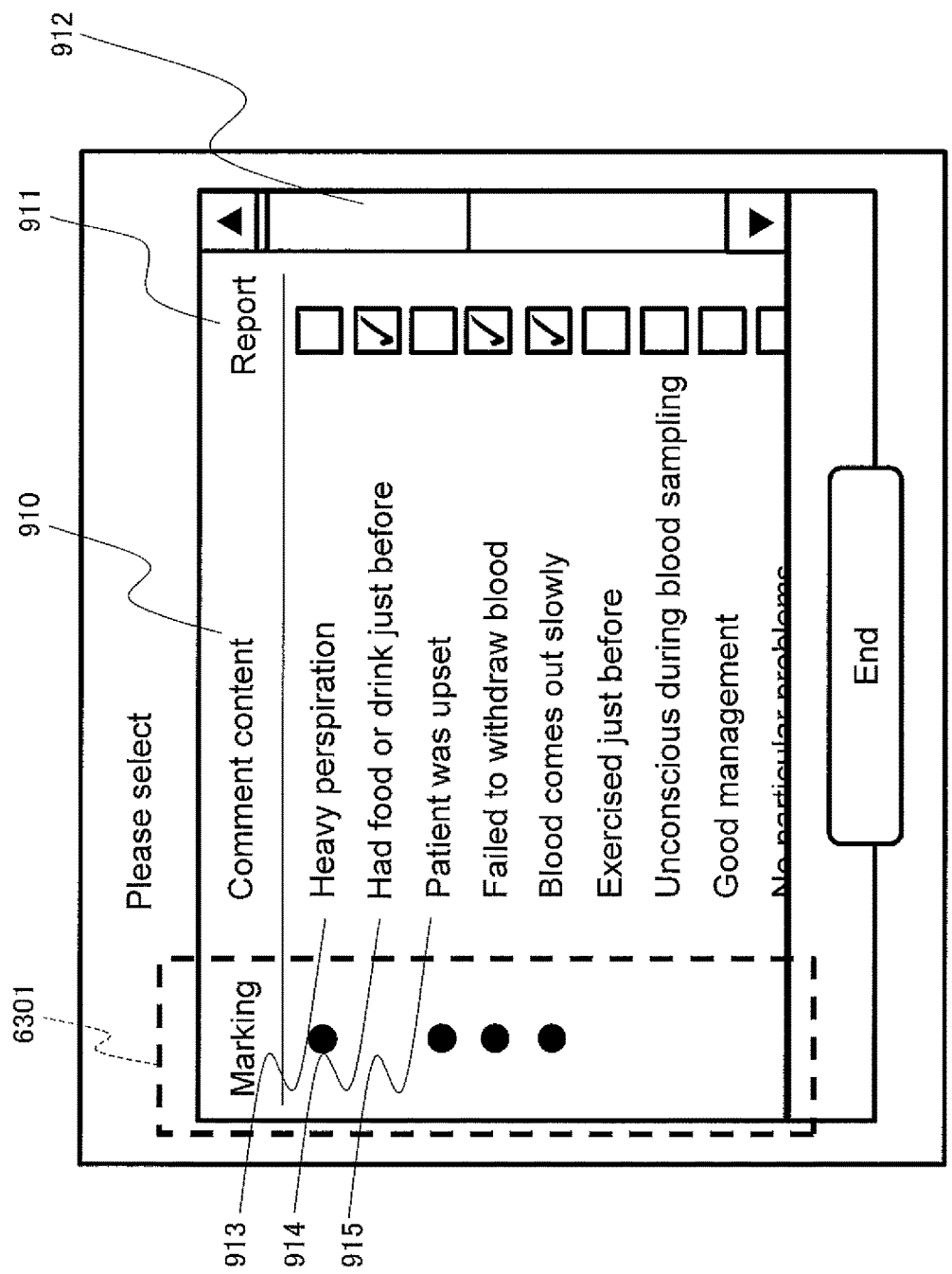
FIG. 63 shows a comment editing screen displayed on a terminal in a clinical laboratory according to yet another embodiment of the present invention.

As shown in FIG. 63, a marking column 6301 for marking and displaying comments designated by the terminal 106 of the clinical laboratory (POCC) may be displayed to the left of the comment content column 910 shown in FIG. 9.

In this case, in order for a comment that has been designated at the terminal 106 of the clinical laboratory to be displayed distinctly from a comment inputted this time, the marking column 6301 is added at a position on the left side corresponding to the designated comment.

In the example shown in FIG. 63, three comments have been selected in the report designation column 911 inputted by the user: "had food or drink just before measurement," "failed to withdraw blood," and "blood comes out slowly."

On the other hand, at the terminal 106 of the clinical laboratory, four comments are selected: "heavy perspiration," "patient was upset," "failed to withdraw blood," and "blood comes out slowly."

Consequently, comments designated by the user are sent to the terminal 106 at the clinical laboratory, and comments designated on the terminal 106 of the clinical laboratory are displayed and transmitted as report items to the user who will perform the next measurement, along with the comments designated this time.

Figure 10:
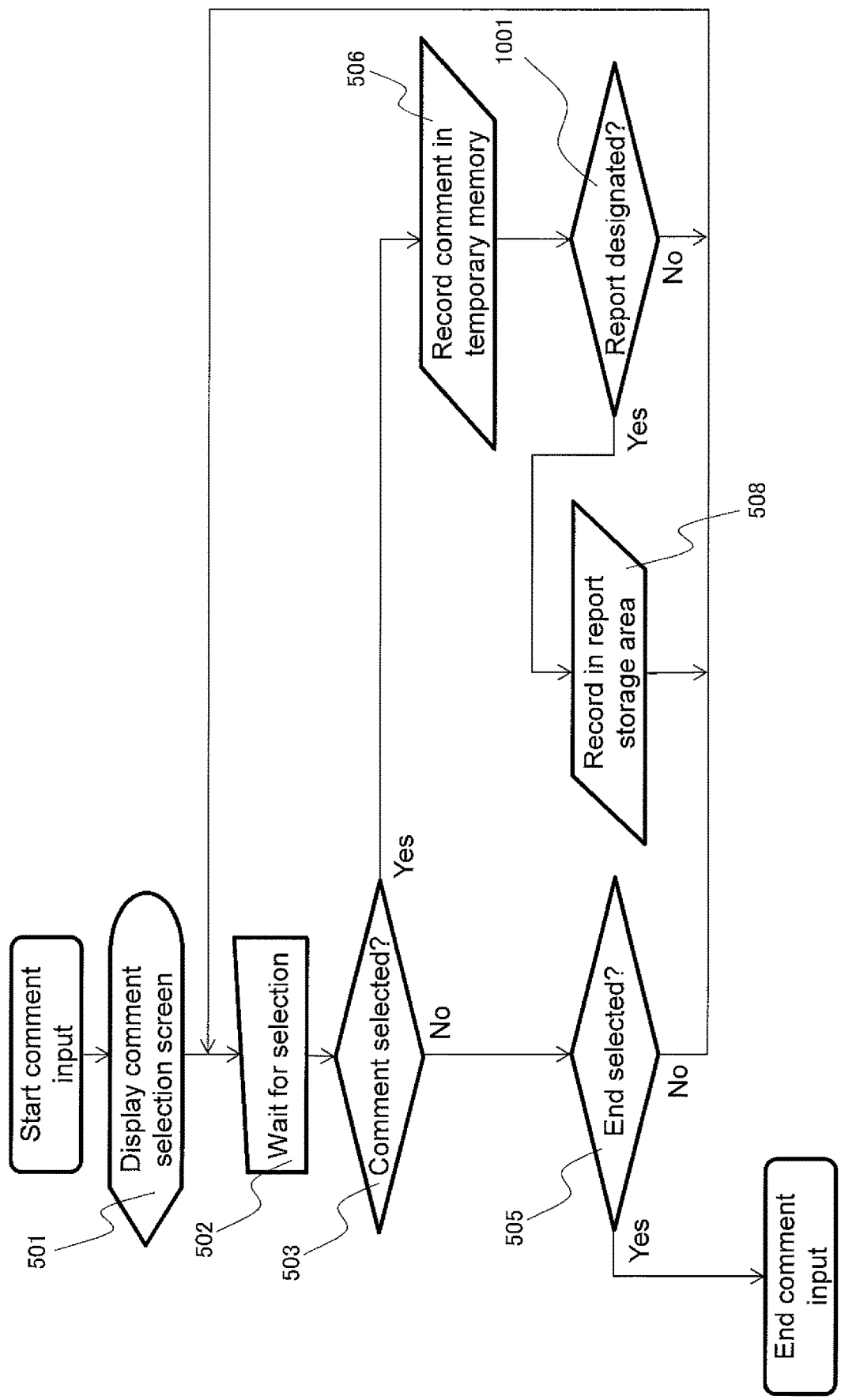
FIG. 10 shows the flow of comment input in Embodiment 1 of the present invention.

FIG. 10 is a flowchart showing details of step 325 of comment input when an administrator designates in advance which comments can be used as report comments.

Since there is no longer any report selection by the user, compared to FIG. 4, there is no step 504 of checking whether or not the report check boxes have been tapped.

Instead, if the comment selection check box has been tapped in step 503, in step 506 the selected comment is recorded in the temporary memory, and then in step 1001 the administrator verifies whether or not the selected comment has been designated for report use. Here, if it has not been specified as a report comment, nothing is done, but if it has been specified as a report comment, the comment selected is recorded in the report storage area 113 in step 508.

Thus, the administrator designates report comments in advance, so it is not necessary for the user to select one at the time of measurement.

In the description with reference to FIGS. 7 and 8, report comments were deleted automatically once they had been displayed, but the configuration may instead be such that the user can choose to delete a report comment.

A case in which the user can choose to erase a report comment will now be described through reference to FIGS. 11 and 12.

Figure 11:
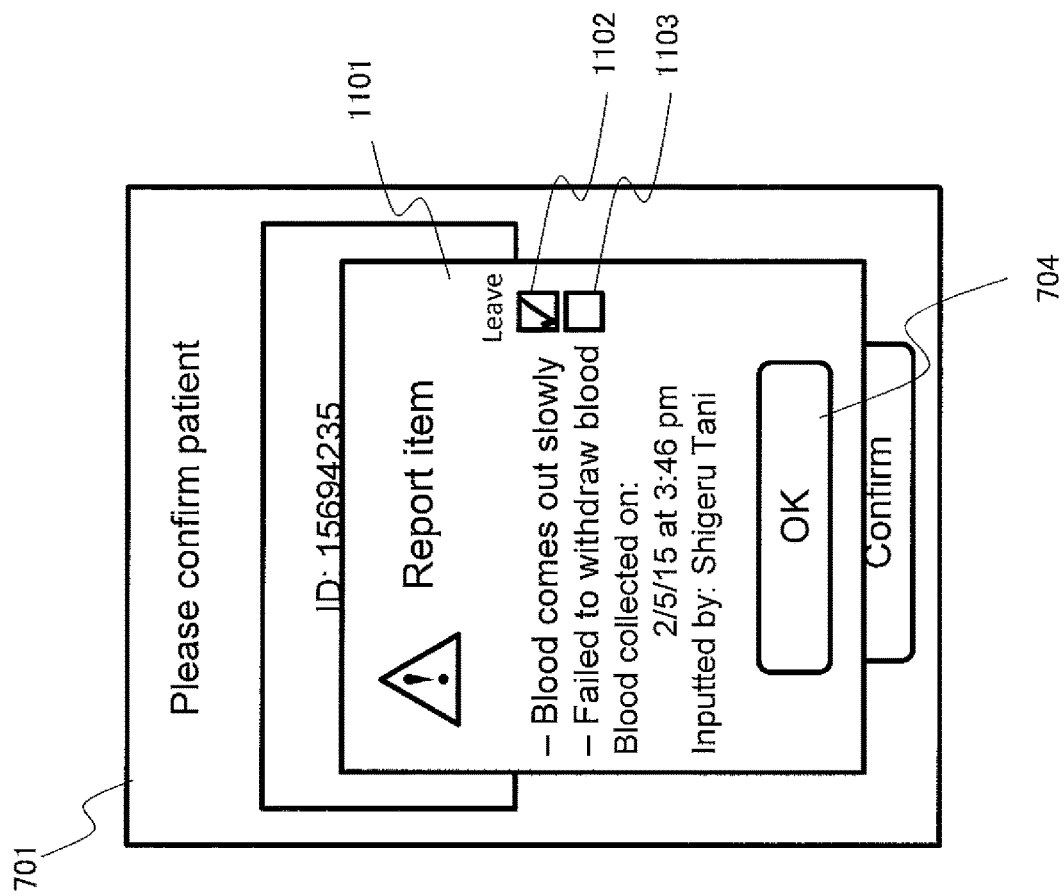
FIG. 11 shows a report comment confirmation screen in Embodiment 1 of the present invention.

FIG. 11 shows an example of the screen displayed on the blood glucose measurement device 101 in step 317 of displaying a report.

In step 314, the patient confirmation screen 701 is displayed, and a report comment confirmation screen 1101 is displayed superimposed over this as a pop-up window.

The report comment confirmation screen 1101 adds check boxes 1102 and 1103 to the report comment confirmation screen 703 illustrated in FIG. 7.

Upon checking a screen, the user determines whether individual report comments are to be erased or left, and decides whether or not to check the check boxes.

For example, a report of "blood comes out slowly" is a conveyed detail that does not change for a particular patient. Thus, the check box 1102 is left checked.

On the other hand, a report of it "failed to withdraw blood" is a one-time incident, so the check box 1103 is unchecked and the report deleted.

After input is finished, the user taps OK button 704 to end the step of displaying the report.

For comments that have been chosen by the user to be left in place, a check box that has been checked from the beginning may be displayed in the space of the report designation column 404 on the display screen of the liquid crystal display component 103 shown in FIG. 4. In this case, a checked check box is also displayed in the space of the comment selection column 403.

Figure 12:
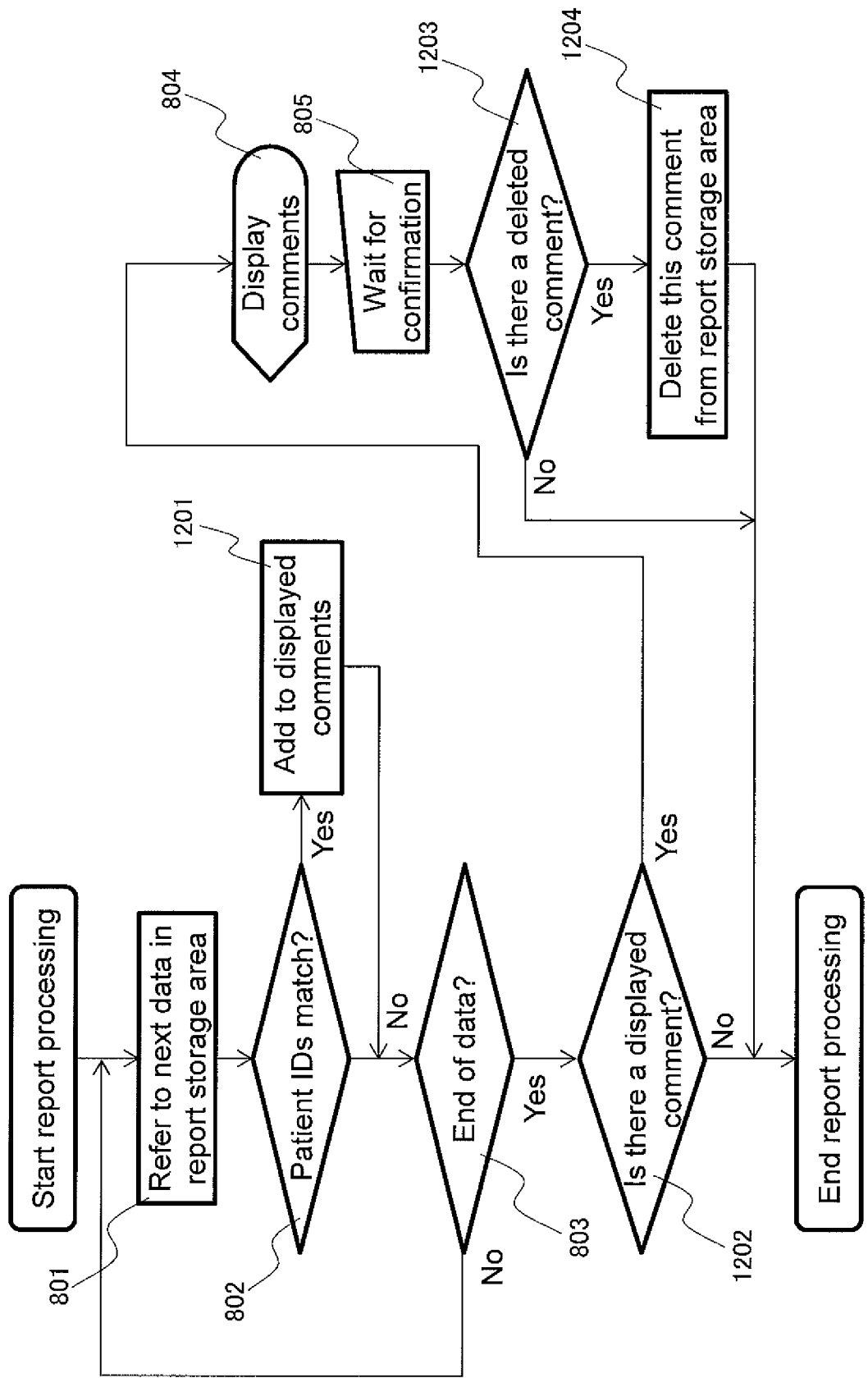
FIG. 12 shows the flow of report processing in Embodiment 1 of the present invention.

FIG. 12 is a flowchart showing details of processing in step 317 of displaying a report in this case. In FIG. 12, in step 801 the focus is on report data for the first person stored in an area 601 within the report storage area 113.

In step 802, the patient ID 604 of the report data for the first person is compared with the patient ID currently being measured to see if they match.

Here, if there is no match, in step 803 the system checks whether or not all of the report data has been confirmed. If there is still data remaining, the flow goes back to step 802, and the step is repeated, focusing on data for the second person. This repetition is continued until it is determined that the final data has been reached in step 803.

In FIG. 8, there was a maximum of one set of data for a specific patient included in the report storage area 113. Therefore, in step 802, if the patient ID 604 matches the patient ID that is currently being measured, the loop of steps 801 to 803 is exited right away.

However, in FIG. 12, there is a possibility that a plurality of sets of data for a particular patient will be included in the report storage area 113. Therefore, the processing of steps 801 to 803 is performed on all of the data included in the report storage area 113, and the system searches for report data for the patient being currently measured.

Therefore, in step 802, if the patient ID 604 matches the ID of the patient currently being measured, a report comment for that data is added as a display-use comment, and the flow goes back to the loop.

If it is determined that processing of all the data in step 803 is finished, the system checks whether or not there is a display-use comment in step 1202. Here, if there is no display-use comment, then there is no report for the patient currently being measured, so step 317 is ended without displaying the report comment confirmation screen 703.

On the other hand, if it is determined that there is a display-use comment in step 1202, the report comment confirmation screen 703 is displayed in step 804.

After the screen display in step 804, the system goes into standby in step 805 and waits for confirmation.

When the user taps the OK button 704, the check boxes 1102 and 1103 are examined in step 1203, and if both have been checked, the processing is ended without doing anything.

Consequently, the data in the report storage area 113 is left as it is, and report comments are displayed at the time of the next measurement as well.

In step 120, if neither of the check boxes 1102 and 1103 has been checked in step 1203, then any comments without a check in 1204 are deleted from the report storage area 113.

Reports can also be displayed using a method in which the number of times a report is made is designated.

Figure 13:
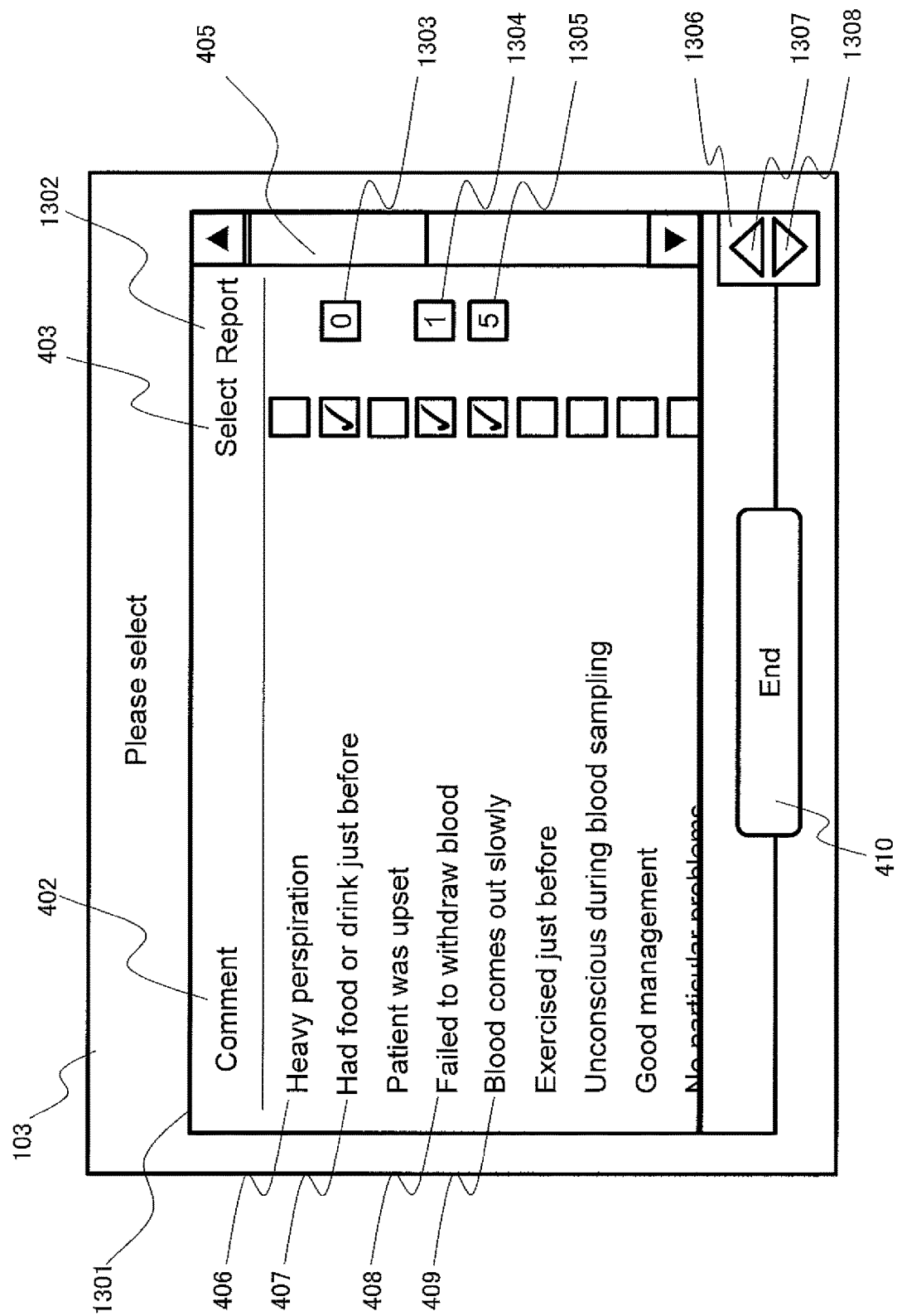
FIG. 13 shows the comment selection screen in Embodiment 1 of the present invention.

FIG. 13 shows the screen displayed in the comment input step 325 in this case.

The comment list 1301 in FIG. 13 differs from the comment selection list 401 in FIG. 4 in that the check box in the report designation column 404 is changed to a report column 1302 displaying the count input boxes 1303 to 1305.

When a check is put in the selection check box, the report count input boxes 1303 to 1305 are displayed.

A zero is entered by default, so if the user wants something to be a report comment, the numerical value of the count input box is changed.

If the user wants to change the numerical value of the count input box, first the count input box to be changed is tapped to display a count change icon 1306.

If the user wants to increase the numerical value of the count input box, the increase button 1307 within the count change icon 1306 is tapped in this state. This allows the numerical value to be increased one tap at a time.

If the user wants to reduce the numerical value of the count input box, the decrease button 1308 within the count change icon 1306 is tapped in this state. This makes it possible to reduce the numerical value one tap at a time.

The numerical value in the count input box can be set six different ways, from 0 to 5, for example.

Report comments are displayed in step 317 the number of times (count) designated here. After they have been displayed the specified number of times, they are deleted from the report storage area 113, after which there is no subsequent display of reports.

The configuration may be such that if the increase button 1307 is tapped when the numerical value is 5, an infinity (∞) mark will appear and unlimited reports are displayed.

In this embodiment, as described above, the user can set the number of times that report comments are displayed, according to the content of the comments.

For instance, the comment 407 is "had food or drink just before measurement," and the fact that the patient had food or drink just before measurement can be a cause of a high blood glucose level. Such information is necessary in data analysis and diagnosis, and is not information to be conveyed to the user during the examination. Therefore, since it is unnecessary to leave this as a report comment, the count input box 1303 is kept at "0."

The comment 408 is "failed to withdraw blood," and if the patient has become upset, it will be necessary to make an apology, etc., and pay attention to this during the next examination. However, since this needs to be done only once (the next time), "1" is inputted in the count input box 1304.

The comment 409 is "blood comes out slowly," which is a characteristic that does not change for a patient. Therefore, since it is necessary to repeat this report comment at number of times, the maximum value "5" is inputted in the count input box 1304.

This allows the user to designate the number of times a report comment is displayed.

Here, the number of times a report is to be made is designated, but in this case, if a patient does not undergo the next measurement due to being discharged from the hospital, etc., this becomes a problem in that the report data for the patient stays in the report storage area forever.

Therefore, it is preferable to store the date and time when a comment was inputted, along with the patient ID, for report comments stored in the report storage area 113. Consequently, when a predetermined period of one week is provided, for example, any report comments older than one week since comment input will be deleted from the report storage area 113. This solves the above problem.

As another method, instead of designating the number of times a report is displayed, the period for which a report is to be displayed may be designated, so that the report comment will be displayed only for the designated period.

Here again, the date and time of comment input may be stored along with the patient ID and the report comment in the report storage area 113. Consequently, any report comments older than the designated period are deleted from the report storage area 113.

For a comment selected to remain due to the count setting, a check box that has been checked from the outset may be displayed in the space of the report designation column 404 on the display screen of the liquid crystal display component 103 shown in FIG. 4. Also, in this case, a checked check box is displayed in the space of the comment selection column 403.

In the above description, an example of when there is only one blood glucose measurement device 101 was given, but in a large hospital it is often the case that there are a plurality of blood glucose measurement devices. Therefore, an example of when there are a plurality of blood glucose measurement devices will be described through reference to FIG. 14.

Figure 14:
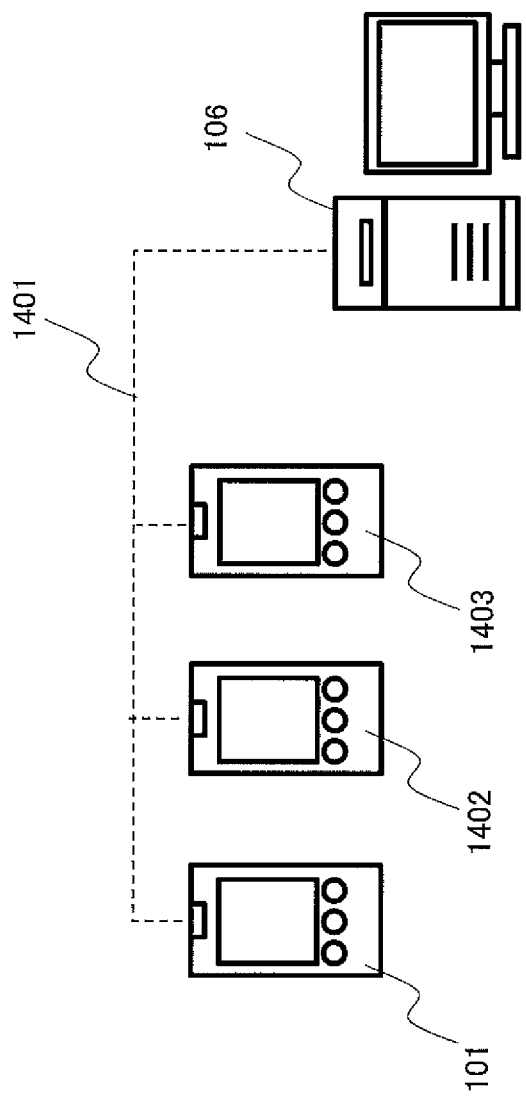
FIG. 14 shows the entire system in Embodiment 1 of the present invention.

FIG. 14 shows the system configuration when there are a plurality of measurement devices.

In the above description, an example was given in which the blood glucose measurement device 101 communicated with the terminal 106 in the clinical laboratory one-to-one.

Here, let us assume that the terminal 106 of the clinical laboratory can communicate with a plurality of blood glucose measurement devices (biological information measurement devices) 101, 1402, and 1403 via a communication means (communication component) 1401.

The communication means 1401 may be a wireless LAN, or a LAN that is wired via a charger.

In this case, the blood glucose level of a patient is measured using one of three blood glucose measurement devices.

Therefore, when the user has used the blood glucose measurement device 101 to measure a patient and has inputted a report comment, for example, even if the blood glucose measurement device 1402 is used for the next measurement of the same patient, the report comment inputted to the blood glucose measurement device 101 must be displayed on the blood glucose measurement device 1402.

Therefore, in the storage format to the temporary memory shown in FIG. 15, a flag indicating whether or not a there is a report comment is added to the comment storage components 1507 to 1509.

Here, as an example, let us assume that if the numeral "1" comes after the last letter of the comment, it indicates that it is a report comment.

For instance, when the blood glucose level of a patient is measured using the blood glucose measurement device 101, let us assume that basically the measurement is performed according to the flow indicated up to this point.

However, let us assume that instead of recording the comment selected only in step 508 in the report storage area 113, "1" is added to the end of the corresponding comment in the comment storage component of the temporary memory.

After this, when the blood glucose measurement device 101 transmits this data to the terminal 106 of the clinical laboratory in step 327, the terminal 106 of the clinical laboratory checks the comment storage components 1507 to 1509 of the sent data.

Here, if a report comment is included, the report comment is sent through the communication means 1401 to all the blood glucose measurement devices 101, 1402, and 1403. The blood glucose measurement devices 101, 1402, and 1403 that have received the report comment store it in their respective report storage areas 113.

Consequently, the report storage areas 113 of all the measurement devices have the same contents, so the report comments can be shared.

As described above, in this embodiment, the report storage area 113 is provided inside the blood glucose measurement device 101. Those comments that have been designated for report are stored in the report storage area 113 after being associated with a patient ID, and when a patient ID is inputted at the time of measurement, the report comment corresponding to that patient is displayed.

Consequently, just before measurement, it is possible to convey report comments from the previous time without any of them being overlooked, and the user can more reliably care for a patient corresponding to a report.

A stored comment associated with a patient ID may also be stored in the report storage area 113 after being associated with time information related to the date and time when the measurement was performed.

The blood glucose measurement device 101 in this embodiment comprises the sensor connector (sensor mounting portion) 110, the blood glucose level calculator (measurement component) 112, the barcode reader (identification information reader) 108, the liquid crystal display component (display component) 103, the data storage component (storage component) 107, the report storage area (storage component) 113, the central controller (controller) 102, and the touch sensor (report item input component) 104.

For each measurement at the blood glucose level calculator 112, the central controller 102 activates an input screen on the liquid crystal display component 103 for inputting a comment (report item). When a comment is inputted on the touch sensor 104, the central controller 102 associates the comment with identification information, corresponding to each measurement at the blood glucose level calculator 112, and stores the result in the report storage area 113. Furthermore, when the patient ID (identification information about the subject) is read by the barcode reader 108 at the next measurement, the central controller 102 determines whether or not there is a comment on the basis of the information stored in the report storage area 113, and if there is a comment, it is displayed on the liquid crystal display component 103.

Here, as shown in FIG. 4, for example, comments stored as report items include "heavy perspiration (by the patient)," "(patient) had food or drink just before measurement," "patient was upset," "failed to withdraw blood," "blood comes out slowly," "exercised just before measurement," "unconscious during blood sampling," "good management," "No particular problem," and the like.

Specifically, in this embodiment, the above-mentioned comments include information such as the condition of the patient noticed by the previous measurer (the first measurer), information related to blood collection, the relationship with the patient, etc.

Consequently, each time the measurer (the second measurer) begins measurement, when the patient ID is read by the barcode reader 108, if there is a comment that was inputted by the time of the previous measurement and that is associated with the patient ID and stored in the report storage area 113, this comment can be displayed on the liquid crystal display component 103.

As a result, the comments inputted during the current measurement can be reliably conveyed to the next measurer (the second measurer). Therefore, the measurer can check the information transmitted from the measurer up to the previous time (the first measurer), and can take appropriate measures for collecting blood from the patient.

The comments displayed on the liquid crystal display component 103 may include not only comments corresponding to the most recent measurement, but also comments corresponding to previous measurements.

However, if comments corresponding to the most recent measurement are displayed on the liquid crystal display component 103 as report comments for the next measurement, the measurer checks the state of the patient at the most recent measurement, information about the measurement, and so on, allowing a more appropriate response to be taken.

Similarly, the most recently stored comments may be displayed on the liquid crystal display component 103 at the next measurement.

Furthermore, with the blood glucose measurement device 101 in this embodiment, comments inputted at the time of measurement may be stored in the report storage area 113 in a state of being associated with identification information such as a patient ID, and time information indicating the measurement date and time.

Consequently, when the next measurer checks the comments displayed as report items, the date and time of the measurement for which the comment was inputted are also confirmed, allowing the proper measures to be taken according to whether the measurement was made a few hours ago or two days ago, for example.

Also, with the blood glucose measurement device 101 in this embodiment, when comments corresponding to the patient ID read by the barcode reader 108 at the start of measurement are not stored in the report storage area 113, the central controller 102 executes measurement of the blood glucose value using blood deposited on the sensor strip 111, without displaying any comments.

Consequently, if no comments have been stored as report items corresponding to the patient to be measured, the display of comments can be omitted and measurement can be carried out faster. As a result, with a first-time patient, for example, measurement can be performed more efficiently by omitting the step of displaying comments.

Furthermore, with the blood glucose measurement device 101 in this embodiment, the central controller 102 causes the liquid crystal display component 103 to give a display prompting removal of the sensor strip 111 from the sensor connector 110 before comments are inputted via the touch sensor 104 at the time of measurement.

This makes it possible to input a comment after the sensor strip 111 on which the blood of the patient has been deposited is removed from the blood glucose measurement device 101. This reduces the risk that the measurer will come into contact with the patient's blood and become infected, etc.

Embodiment 2

Another embodiment of the present invention related to metric data acquisition will now be described through reference to FIGS. 18 to 56.

Figure 18:
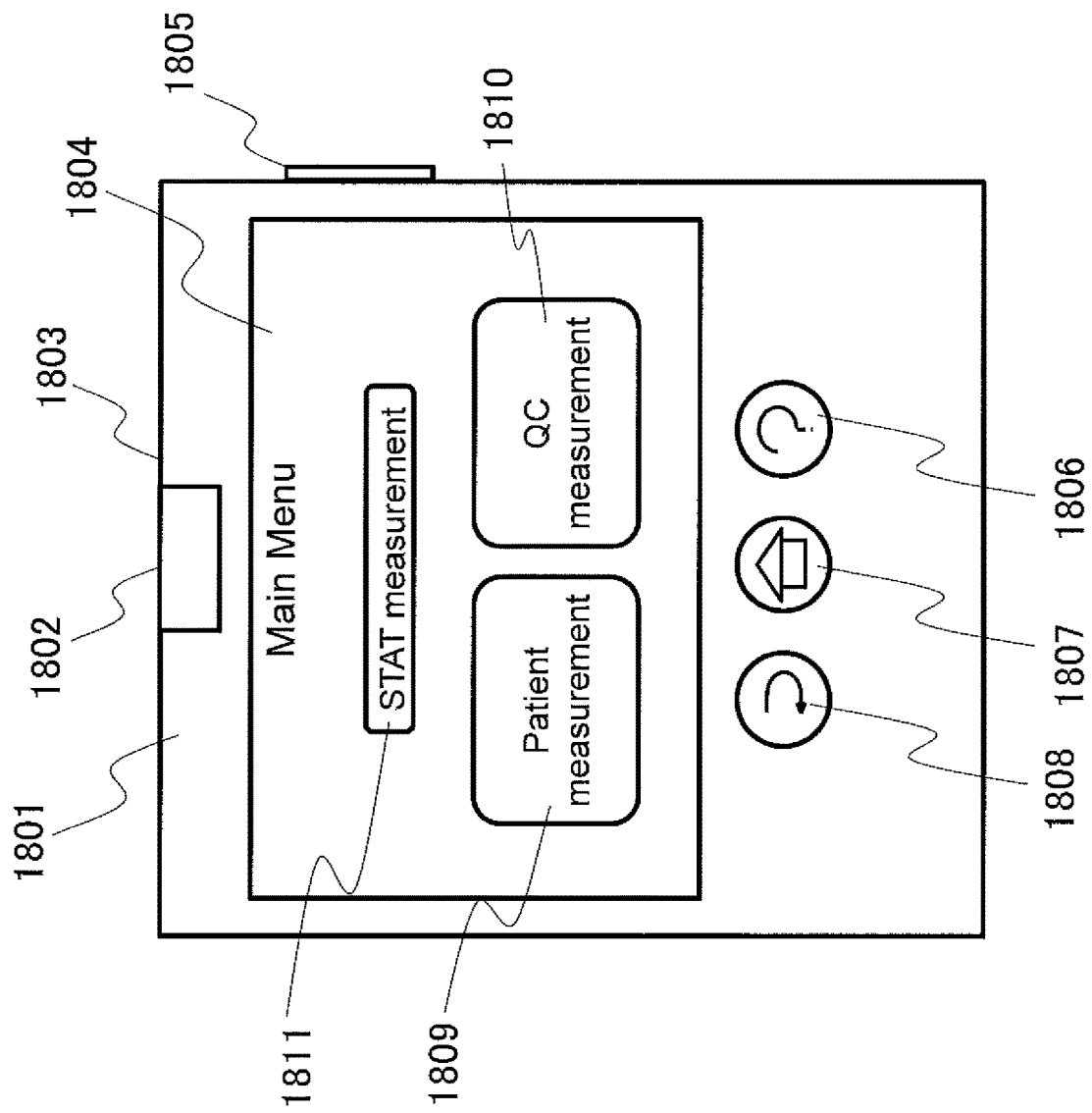
FIG. 18 shows the appearance of a blood glucose measurement device in Embodiment 2 of the present invention.

FIG. 18 shows an external view of the biological information measurement device of this embodiment.

Here, a blood glucose measurement device will be described as an example of a biological information measurement device, but the present invention is not limited to a blood a glucose measurement device.

Many operations are performed via a touch screen of the blood glucose measurement device in this embodiment.

In FIG. 18, 1801 denotes a blood glucose measurement device as an example of a biological information measurement device.

The blood glucose measurement device 1801 in this embodiment is a measurement device intended for use in a hospital. For this reason, measurement of the blood glucose level of a patient is performed by a healthcare provider (user) such as a doctor or a nurse.

The blood glucose measurement device 1801 comprises a sensor strip connector (sensor mounting portion) 1802, a barcode reader (identification information reader) 1803, a touch panel (report item input component) 1804, a power switch 1805, a help button 1806, a home button 1807, and a back button 1808.

A disposable sensor strip (sensor) is inserted into the sensor strip connector 1802. Blood is then deposited on the sensor strip inserted in the sensor strip connector 1802, and the blood glucose level is measured.

The barcode reader 1803 reads a barcode for identifying a user ID, a sensor strip ID, a patient ID, or the like. The same function can be realized by an RF tag reader or the like.

The touch panel 1804 consists of a liquid crystal display component and a superposed touch sensor, and functions as a man-machine interface that both gives a display to the user and receives instructions inputted from the user. Menus, instructions for operation, and the like are all performed via the touch panel 1804.

1805 is the power switch of the blood glucose measurement device 1801.

1806 is the help button. Regardless of the timing of the operation, pressing the help button 1806 allows an explanation of an operation related to the currently displayed state, tips, and so forth to be displayed on the touch panel 1804.

Specifically, for example, when the help button 1806 is pressed in a state of waiting for a user ID to be scanned, a detailed instruction of "point the scanner of the measurement device at the barcode of your name tag" is displayed on the touch panel. At the same time, when the confirmation button displayed on the touch panel is tapped, the display returns to the original screen.

1807 is the home button. When the home button 1807 is pressed, the current operation can be interrupted to return to the main menu.

1808 is the back button. When the back button 1808 is pressed, the display returns to the previous operation, and the user can start over. However, if there is interaction with the outside world, such as depositing blood or transferring data, you can not return to the previous operation. Therefore, in such a case, operation of the back button is invalid.

In FIG. 18, a main menu is displayed on the touch panel 1804.

Buttons for performing patient measurement 1809, QC measurement 1810, and STAT measurement 1811 are displayed in the main menu.

The patient measurement button 1809 is pressed to start a sequence for measuring the blood glucose level of the patient. Normally, blood glucose measurement of a patient is performed by pressing this button.

The QC measurement button 1810 is pressed to start a sequence of QC measurement. Here, "QC measurement" means measuring a QC solution used for calibration, and is performed periodically to guarantee the function of the blood glucose measurement device.

How often QC measurement is performed will be determined for each hospital. For example, if it has been 12 or more hours since the QC measurement was performed, measurement is not performed even if the patient measurement button 1809 is pressed.

However, it is sometimes urgently necessary to measure the blood glucose level of a patient in a hospital. For this reason, the STAT measurement button 1811 is provided as a menu for emergency measurement in the event that the patient measurement button 1809 has been disabled due to expiration of the QC measurement in such an emergency.

The STAT measurement button 1811 is pressed to enable measurement of a patient's blood glucose level even when the QC measurement has expired.

Regardless of whether the patient measurement button 1809, the QC measurement button 1810, or the STAT measurement button 1811 is pressed, measurement will be performed in substantially the same measurement sequence. However, when the results are recorded, they are classified by the mode in which the measurement was performed. The measurement result of QC measurement 1810 is used for performance management. The measurement result of the STAT measurement 1811 is handled in substantially the same manner as the patient measurement button 1809, but this means that the accuracy can not be guaranteed.

Figure 19:
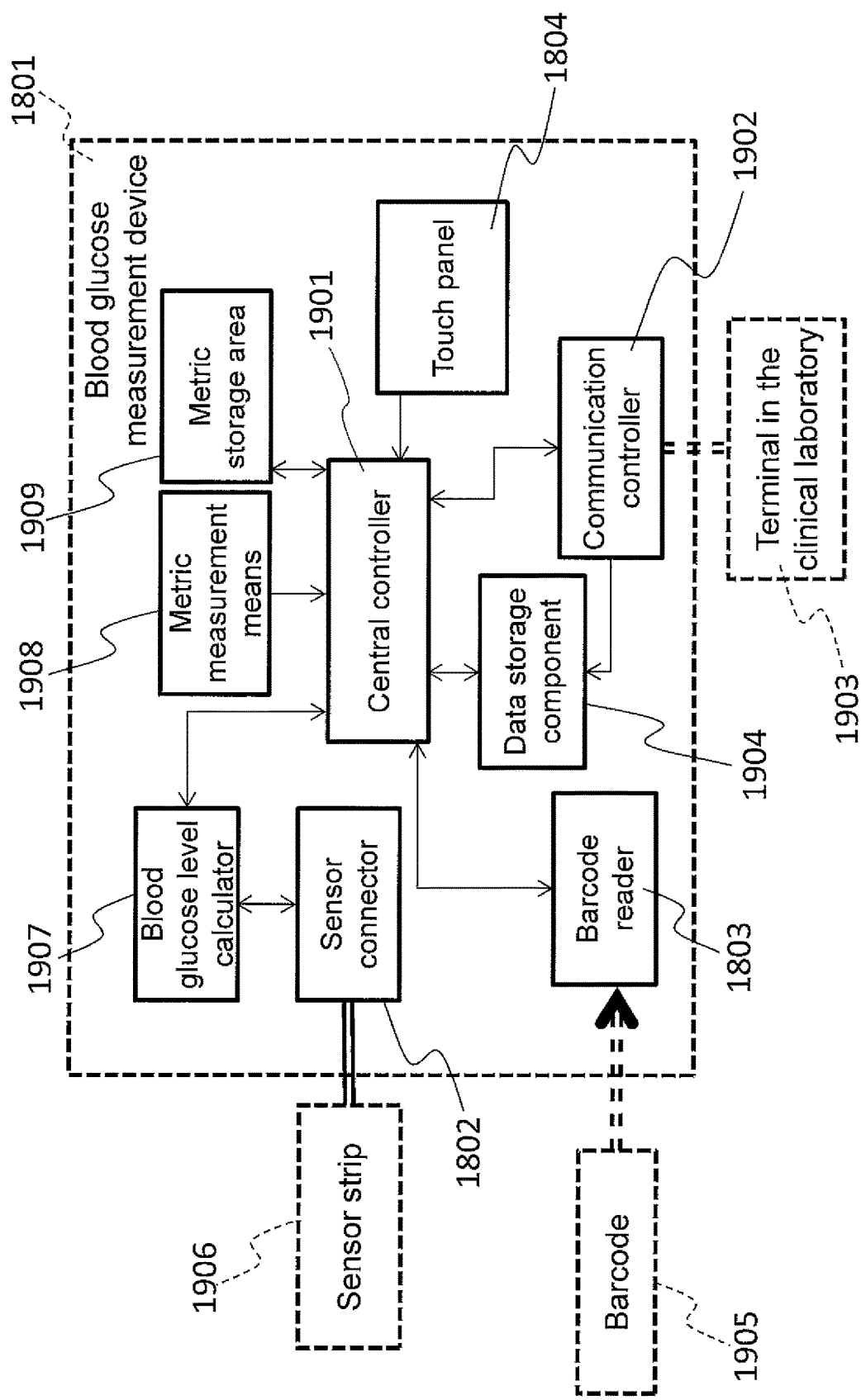
FIG. 19 is a system configuration diagram of a blood glucose measurement device in Embodiment 2 of the present invention.

FIG. 19 is a system configuration diagram of the blood glucose measurement device 1801 pertaining to this embodiment.

In the blood glucose measurement device 1801, 1901 denotes a central controller (controller) that performs all the processing.

A touch panel 1804 is connected to the central controller 1901.

The blood glucose measurement device 1801 also comprises a communication controller 1902. Consequently, the blood glucose measurement device 1801 can communicate with a terminal 1903 of a clinical laboratory in a hospital via the communication controller 1902. The clinical laboratory terminal 1903 is used as a data processing apparatus that processes the measurement results.

In this embodiment, evaluation data (discussed below) is also produced at the terminal 1903 of the clinical laboratory.

The latest data about patients and users in the server of the terminal 1903 in the clinical laboratory is stored in the data storage component in the blood glucose measurement device 1801 via the communication controller 1902.

Patient data is, for example, a list of patient IDs and the name, sex, and date of birth of each patient associated with those patient IDs. User data is, for example, a list of user IDs and the name and password of each user associated with those user IDs.

The blood glucose measurement device 1801 comprises a barcode reader 1803.

The barcode reader 1803 reads a barcode 1905 attached to a patient wrist, a user's name tag, or the like, and sends the ID to the central controller 1901.

Upon receiving the ID, the central controller 1901 refers to the data tied to the ID from the data storage component (storage component) 1904. For example, when the barcode reader 1803 reads the barcode of a patient ID, the central controller 1901 retrieves from the data storage component 1904 the patient's name, sex, and date of birth associated with the read ID. This makes it possible to learn the name, sex, and date of birth of the patient from the barcode on the patient's wrist.

The type of the barcode 1905 is the same as that shown in FIG. 2, and what is currently being used at the hospital can be used without modification.

The blood glucose measurement device 1801 comprises a sensor strip connector 1802.

A sensor strip (sensor) 1906 for measuring blood glucose level is inserted into the sensor strip connector 1802. A voltage signal corresponding to the blood glucose level is generated when blood is deposited on the sensor strip 1906 in a state of being inserted into the sensor strip connector 1802. The blood glucose level calculator (measurement component) 1907 reads this voltage signal via the sensor strip connector 1802, and transmits the result of calculating the blood glucose level to the central controller 1901.

It is also possible for the central controller 1901 to have the function of the blood glucose level calculator 1907. In that case, the actual calculation from voltage to blood glucose level is performed by the central controller 1901.

1908 is a metric measurement means, which is one of the main features of this embodiment.

Since there are a plurality of types of metric, the metric measurement means 1908 measures a plurality of types of metric. The metrics will be described in detail below.

Here, the metric measurement means 1908 sometimes acquires new information that was not acquired by a conventional blood glucose measurement device as metric data, and sometimes uses information acquired by a conventional blood glucose measurement device as the metric data.

The acquired metrics are stored in the metric storage area 1909. Although the metric storage area 1909 is shown separately here, the metric storage area 1909 may be provided as part of the data storage component 1904.

Figure 20:
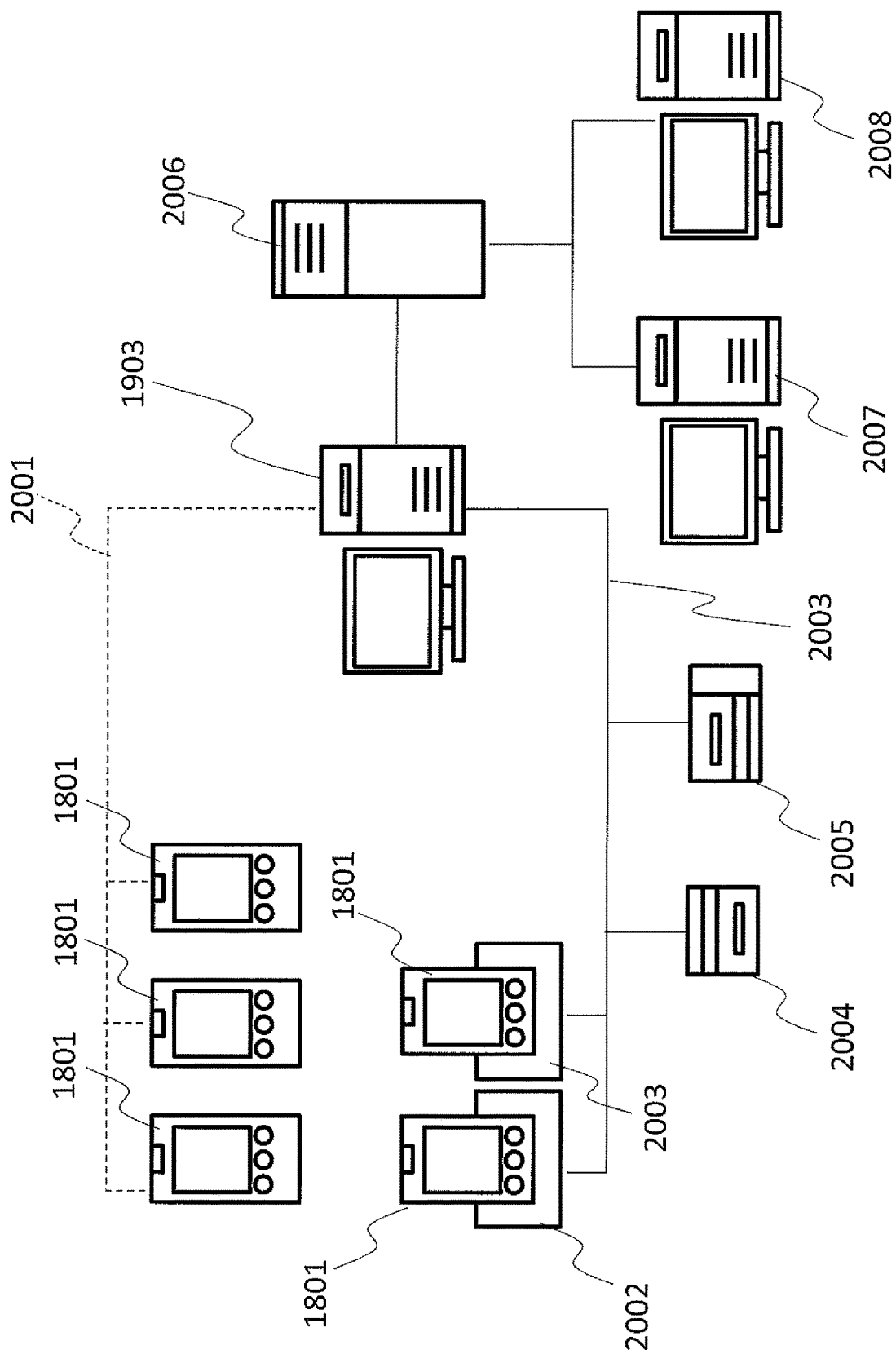
FIG. 20 shows a biological information measurement system in Embodiment 2 of the present invention.

FIG. 20 is a block diagram of the biological information measurement system in this embodiment.

A plurality of blood glucose measurement devices 1801 are installed in a hospital and can communicate with the terminal 1903 of the clinical laboratory via a wireless communication means 2001.

In addition, the blood glucose measurement device 1801 can communicate with the terminal 1903 of the clinical laboratory through a wired communication means 2003 via a docking station 2002.

The docking station 2002 can perform wired communication and can also charge the blood glucose measurement device 1801. Therefore, after use the blood glucose measurement device 1801 is returned to the docking station 2002 in the nurse station, etc.

A urine component measurement device 2004 and a blood component measurement device 2005 can also communicate with the terminal 1903 of the clinical laboratory via the wired communication means 2003.

In this embodiment, a blood glucose measurement device is given as an example of the biological information measurement device of the present invention, but the present invention can similarly be applied to the urine component measurement device 2004 and the blood component measurement device 2005.

All of the test results in the hospital are collected in the terminal 1903 of the clinical laboratory. The testing administrator confirms each piece of all the data stored in the terminal 1903 of the clinical laboratory, and refers to the patient's situation, the management state of the device, the user's comments, and so forth, and sends only the reliable data to the electronic medical record 2007 via the hospital server 2006.

The number of tests and other such information are transmitted to an accounting terminal 2008 and used for insurance claims and the like.

Here, in order to explain how to use the collected data, the hospital server 2006, the electronic medical record 2007, and the accounting terminal 2008 are also illustrated.

However, this embodiment basically involves the use of a biological information measurement device and a terminal in a clinical laboratory, and the hospital server 2006, the electronic medical record 2007, the accounting terminal 2008 are used the same way as usual. Therefore, detailed description of the hospital server, the electronic medical record, and the accounting terminal will be omitted in the following description.

FIG. 21 shows a list of data acquired by one blood glucose measurement device 1801 in a single measurement in the above system.

In FIGS. 21, 2101 to 2107 are medical data acquired by a blood glucose measurement device in the past. 2108 to 2113 are examples of metric data, which is one of main features of this embodiment. The medical data 2101 represents an attribute of measurement, and includes information such as that blood glucose is being measured, attributes thereof (whether patient measurement, QC measurement, or STAT measurement), and the ID of the measurement device. The medical data 2102 is the ID of the user who performed the measurement, the medical data 2103 is the sensor ID of the sensor strip that was used, and the medical data 2104 is the ID of the patient who was measured.

The medical data 2104, in the case of QC measurement, is the ID of the calibration QC sample solution. The medical data 2105 is the patient's blood glucose level found by measurement. The medical data 2106 is the measurement date and time, and the medical data 2107 is a comment by the user at the time of measurement.

The purpose of the above data is to ascertain the blood glucose level for diagnosis of the patient and to confirm the reliability of this data, and is the same as what was acquired in conventional blood glucose measurement.

On the other hand, the metric data 2108 is how long it took to scan the user ID. The metric data 2109 how long it took to scan the sensor ID. The metric data 2110 how long it took for the patient ID scan. The metric data 2111 how long it took for patient confirmation. The metric data 2112 is how long it took for the entire measurement. The metric data 2113 is the number of operations, that is, how many times the screen was touched in this case. All of this data is metric data.

The metric data has nothing to do with treatment, and is related to the skill of the user and the condition of the device. This will be described in detail below.

The metric data shown here is just an example of metric data. This embodiment will be described below using the above six types of data as an example.

Figure 22:
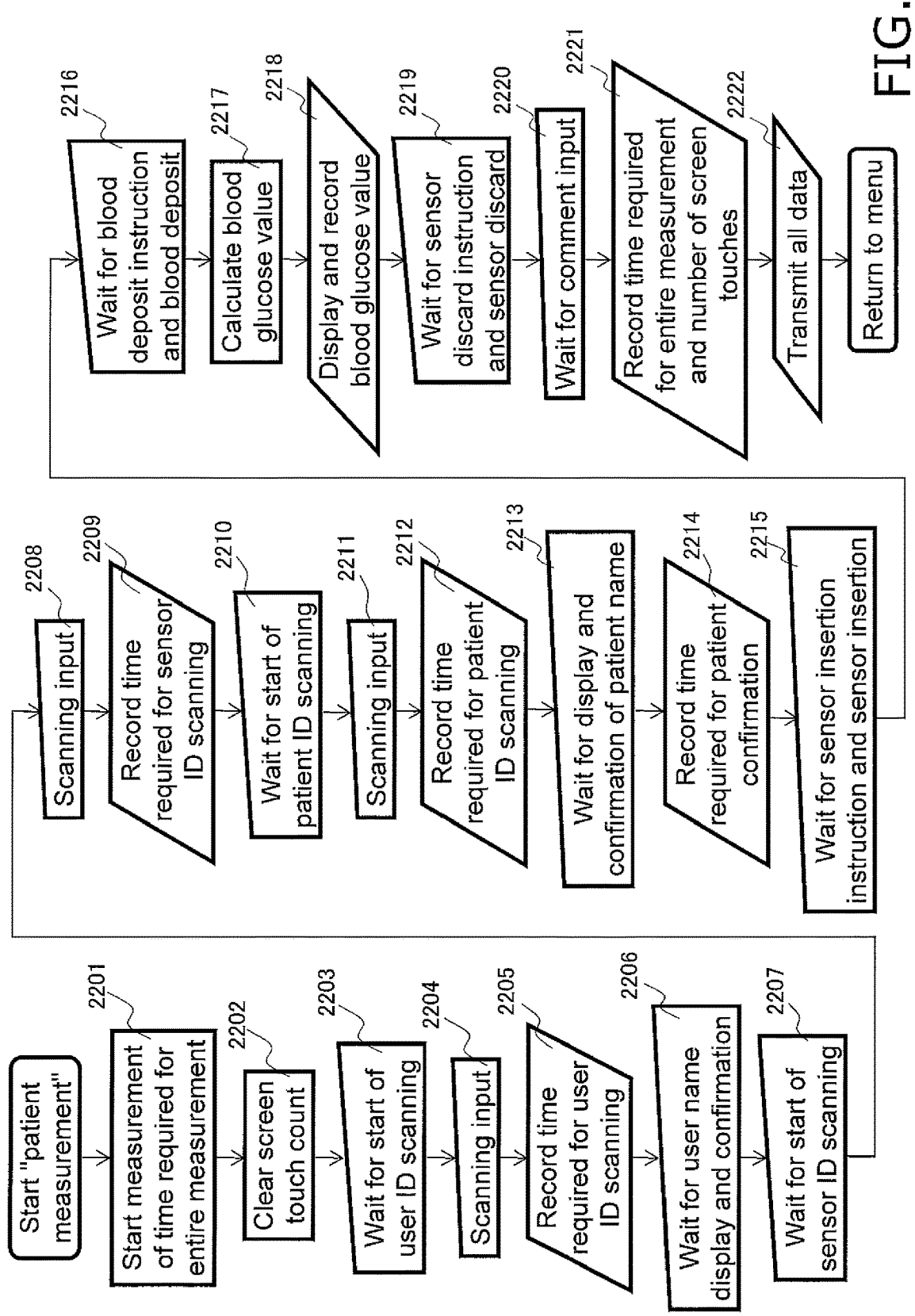
FIG. 22 shows the processing flow of the blood glucose measurement device in Embodiment 2 of the present invention.

FIG. 22 shows the flow of processing for acquiring all the data shown in FIG. 21.

In FIG. 22, first, in step 2201, measurement of the metric data (measurement of the time) 2112 required for the entire measurement is started. More specifically, the metric measurement means 1908 acquires the current time from an internal clock (not shown), stores this time in the metric storage area 1909 as the measurement start time, and then later uses it to find the metric data (measurement of the time) 2112 required for the entire measurement.

In step 2202, the screen touch count (metric data 2113) throughout the measurement is cleared. More specifically, a touch counter in the metric storage area 1909 is set to 0, after which the counter is incremented by one each time the user touches the touch panel 1804, which gives the screen touch count (metric data 2113).

In step 2203, an instruction to scan the user ID is issued to the touch panel 1804, and the measurement of how long it took to scan the user ID (metric data 2108) is started.

More specifically, the metric measurement means 1908 acquires the current time from the built-in clock and stores it in the metric storage area 1909 as the measurement start time.

When the user holds up the barcode 202 to the barcode reader 1803, in step 2204 the barcode reader 1803 reads the user ID (2102).

Immediately after this, in step 2205 how long it took to scan the user ID (metric data 2108) is recorded. More specifically, the metric measurement means 1908 acquires the current time from the built-in clock, and in step 2203 subtracts from this the scan start time stored in the metric storage area 1909.

Consequently, how long it took to scan the user ID (metric data 2108) is found, and this is recorded in the metric storage area 1909 as metric data 1.

In step 2206, the name of the user corresponding to the read user ID (2102) is retrieved from the data recorded in the data storage component 1904. This is then displayed on the touch panel 1804, and the system waits for confirmation by the user.

Then, when it is recognized by a screen touch that the user has confirmed, an instruction to scan the sensor ID is inputted to the touch panel 1804 in step 2207, and the metric data (measurement of the time) 2109 required for the sensor ID scan is started.

When the user holds up the barcode 206 to the barcode reader 1803, in step 2208 the barcode reader 1803 reads the sensor ID (2103).

Immediately after this, in step 2209, metric data (measurement of the time) 2109 required for the sensor ID scan is recorded in the metric storage area 1909.

In step 2209, the expiration date of the sensor is checked at the same time. Therefore, the read sensor ID is retrieved from a sensor database (not shown) in the blood glucose measurement device 1801. Then, the expiration date of the sensor strip recorded here is read out. If the current date has passed the expiration date, an expiration error is displayed, an instruction to use another sensor is issued, and the processing returns to step 2207.

Similarly, in step 2210, an instruction to scan the patient ID is issued to the touch panel 1804, and the measurement of how long it took to scan the patient ID (metric data 2108) is started.

When the user holds up the barcode 204 to the barcode reader 1803, in step 2211 the barcode reader 1803 reads the patient ID (2104).

Immediately after this, in step 2212 the metric data (measurement of the time) 2110 required for the patient ID scan is recorded in the metric storage area 1909.

In step 2213, the name, sex, date of birth, and the like of the patient corresponding to the read patient ID (2104) are retrieved from the data recorded in the data storage component 1904, and this is displayed on the touch panel 1804. Then, measurement of the metric data (measurement of the time) 2111 required for patient confirmation is started and the system waits for user confirmation.

When the confirmation by the user is recognized from a screen touch, in step 2114, the metric data (measurement of the time) 2111 required for patient confirmation is recorded in the metric storage area 1909.

After this, the report display described in the first embodiment may be performed as needed, but will not be described here.

Next, in step 2215, an instruction to insert the sensor strip 1906 into the sensor strip connector 1802 is displayed on the touch panel 1804.

When the sensor strip 1906 is inserted, in step 2216 an instruction to deposit the patient's blood on the sensor strip 1906 is displayed on the touch panel 1804.

Here, when a deposit of blood is detected, in step 2217 the blood glucose level is calculated. The blood glucose level thus found (medical data 2105) is displayed on the touch panel 1804 in step 2218, and the measurement date and time (medical data 2106) are recorded at the same time.

In step 2219, an instruction is displayed on the touch panel 1804 to remove and discard the sensor strip 1906.

In step 2220, the user inputs comments regarding this measurement. Here, a list of comments that can be selected is displayed on the touch panel 1804, and the user selects up to two comments from this list.

Also, in rare cases the user may want to leave a comment not on the comment list. Therefore, in such a case, the user can manually enter a custom comment. The inputted custom comment is recorded by the same means as a selected comment.

In step 2221, the metric data (measurement of the time) 2112 required for the entire measurement is found. More specifically, the metric measurement means 1908 acquires the current time from the built-in clock. The metric data (measurement of the time) 2112 required for the entire measurement is found by subtracting the measurement start time stored in the metric storage area 1909 from this time in step 2201, and is recorded in the metric storage area 1909.

Attributes about measurement (medical data 2101) can be found from menu operation, the device number, or the like.

Since all the data of the medical data 2101 to 2113 shown in FIG. 21 are prepared by the above procedure, in step 2222 all the data is transmitted to the terminal 1903 of the clinical laboratory via the communication controller 1902.

When transmitting data from the blood glucose measurement device 1801 to the terminal 1903 of the laboratory, it must go through the wireless communication means 2001 or the wired communication means 2003 in the hospital.

In a hospital where a conventional blood glucose measurement device is utilized, the only data assumed to be sent from the blood glucose measurement device to the terminal line of the clinical laboratory is the medical data 2101 to 2107 in FIG. 21. However, remodeling a hospital communication system in order for the transmission to include the additional metric data 2108 to 2113 is a major job in terms of both cost and time.

Also, this communication system includes not only blood glucose measurement devices, and other devices in the hospital also make use of the same communication system, so remodeling may affect those other measurement devices as well.

Therefore, a conventional communication system is used here just as it is, and a method will now be described for adding the metric data 2108 to 2113 to the transmission.

Figure 23:
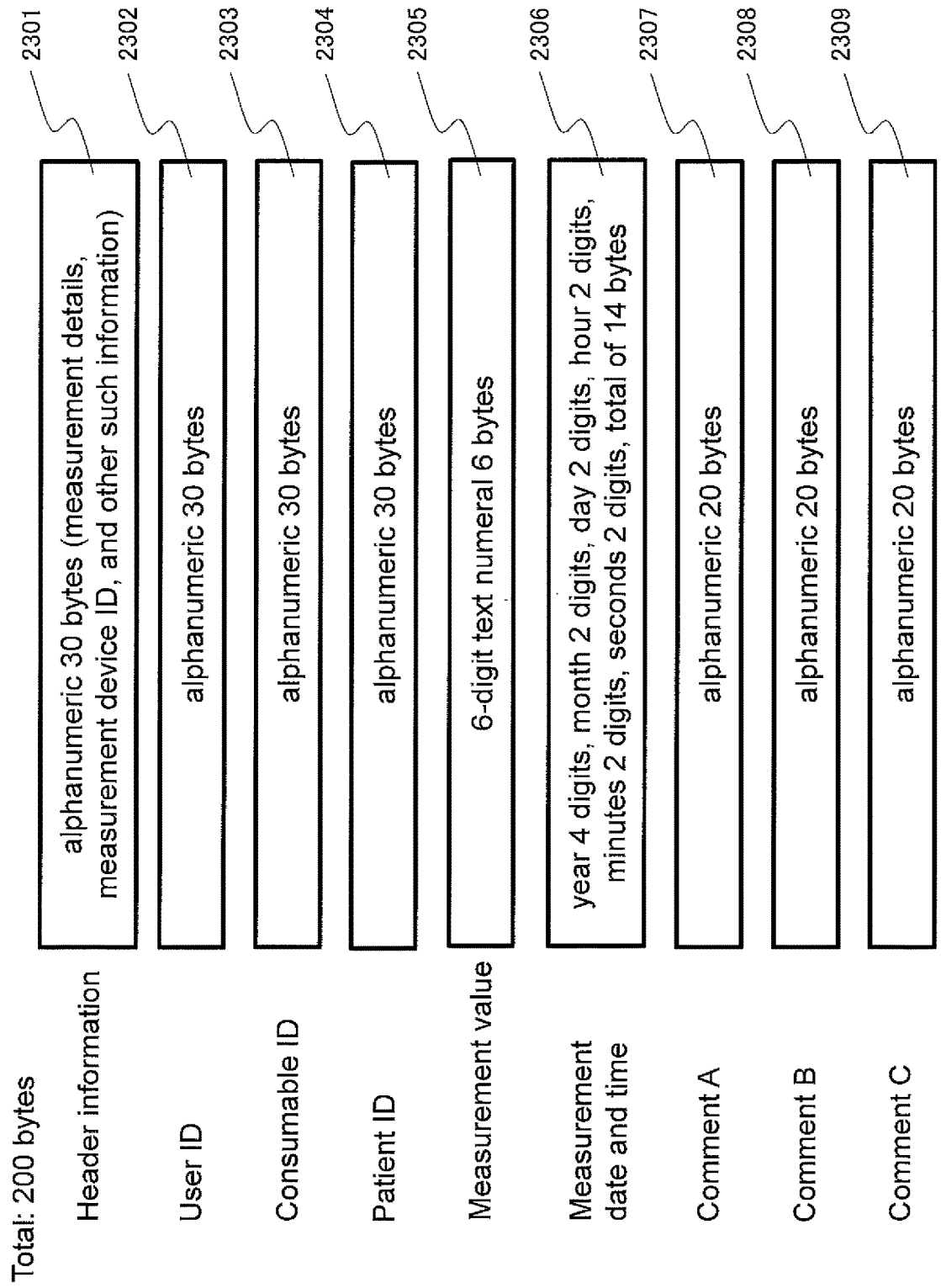
FIG. 23 shows examples of the format of transmission from a typical measurement device.

FIG. 23 shows an example of a typical format for transmission from a measurement device in a hospital to a terminal in a clinical laboratory. Although the transmission format is actually more complicated, including error correction and so forth, only the data content is shown here. Data is transmitted in the same format to all testing devices, and not just blood glucose measurement devices.

In FIG. 23, 2301 is header information. The header information 2301 is the medical data 2101 in a blood glucose measurement device. Here, this information includes whether the data is a blood glucose value, classification of patient measurement or QC measurement possible, etc., the ID of the device used for the measurement, and the like.

2302 is a user ID. The user ID 2302 is the same as the user ID (2102) in the blood glucose measurement device.

2303 is a consumable ID. The consumable ID 2303 corresponds to the sensor ID (2103) in the blood glucose measurement device.

2304 is a patient ID. The patient ID 2304 is the same as the patient ID (2104) in the blood glucose measurement device.

2305 is a measurement value. The measurement value 2305 is the blood glucose level (medical data 2105) in the blood glucose measurement device.

The measurement date and time 2306 corresponds directly to 2106.

Also, comments A to C (2307 to 2309) are likewise 2107.

Consequently, among the data pertaining to this embodiment, the medical data 2101 to 2107 is directly transmitted as 2301 to 2308. The metric data 2108 to 2113 is transmitted as comment C (2309). The method for transmitting the metric data 2108 to 2113 will be described through reference to FIG. 24.

Figure 24:
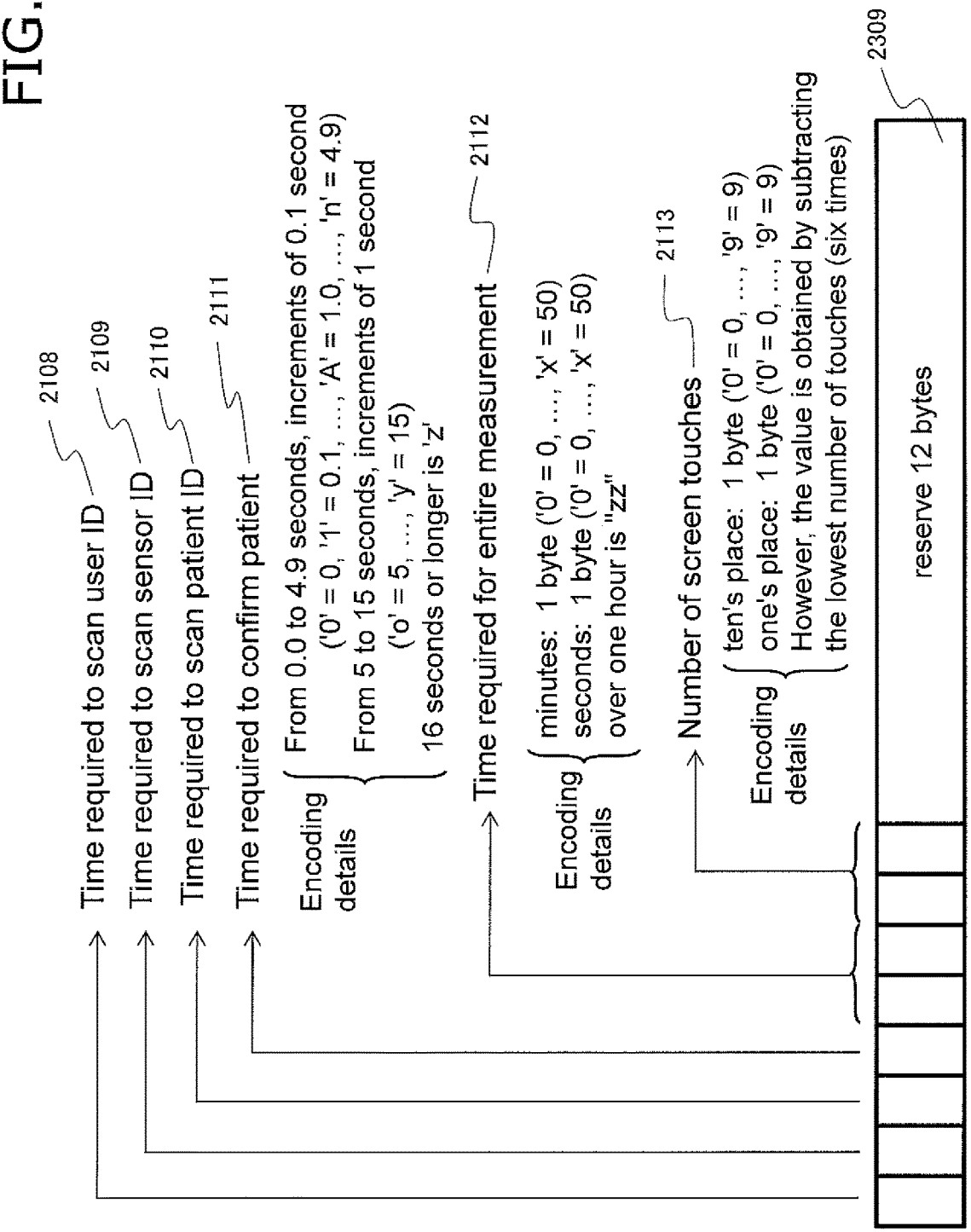
FIG. 24 shows the transmission format of metric data in Embodiment 2 of the present invention.

FIG. 24 is the transmission format of the metric data in this embodiment.

As described above, metric data is sent encoded in the comment C (2309). Here, since a comment area is utilized in the transmission, only alphanumeric characters can be used in each byte.

That is, 26 uppercase letters, 26 lowercase letters, and 10 numerals (62 characters) need to be encoded. More specifically, first, among the metric data, the time required for a user ID scan (metric data 2108), the metric data (measurement of the time) 2109 required for a sensor ID scan, the metric data (measurement of the time) 2110 required for a patient ID scan, and the metric data (measurement of the time) 2111 required for patient confirmation are each set at one byte, and these four bytes are stored starting at the front of the comment C (2309).

The value typically obtained for these four types of metric data is a few seconds. Thus, the four types of metric data is coded in one of the following three scenarios.

First, if the value is from 0.0 to 4.9 seconds, numerals and letters are sequentially assigned in increments of 0.1 second. In other words, the character 0 is assigned for 0.0 seconds, the character 1 for 0.1 second, and so on, with the character 9 for 0.9, the character A for 1.0, the character B for 1.1, and so on, and the character n for 4.9.

Next, first, if the value is from 5 to 15 seconds, lower case letters are sequentially assigned in increments of 1 second. That is, 5 the character o is assigned for 5 seconds, the character p for 6 seconds, and so on, with the character y for 15 seconds. If the value is 16 seconds or more, the character z is assigned.

This allows the metric data 2108 to 2111 to be encoded in 4 bytes of ASCII characters.

Next, the metric data (measurement of the time) 2112 required for the entire measurement is coded in the next 2 bytes. Because the time required for the entire measurement spans several minutes, the following coding is performed.

Minute and the seconds are each assigned to separate bytes, with them being encoded using upper bytes for minute and lower bytes as seconds. Since both minutes and seconds range from 0 to 59, encoding is carried out by the same method for both.

In both cases, 0 to 59 are assigned one by one to alphanumeric characters. More specifically, the character 0 is assigned to 0, the character 1 to 1, and so on, with the character 9 used for 9, the character A for 10, and so on, with the character Z for 35, the character a for 36, and so on, with character x used for 59.

When the metric data (measurement of the time) 2112 required for the entire measurement exceeds 1 hour, this is represented by 2-byte zz.

In addition, the total number of screen touches (metric data 2113) is also encoded as the following two bytes. The total number of screen touches (metric data 2113) is about 100 times at the maximum. Therefore, the number of times is represented by two digits, with each digit represented by one byte.

However, if the minimum touch count is set to times in order to increase the values that can be expressed even a little, encoding is done after first subtracting 6 from the total number of screen touches (metric data 2113). For example, if the total number of screen touches (metric data 2113) is 21 times, first we subtract 6 from 21 to obtain 15, the 1 in the ten's place is represented by the character 1, and the 5 in the one's place is represented by the character 5. If the number of times is 106 or higher, it is represented by 2-byte zz.

Thus, the metric data 2108 to 2113 can be encoded in ASCII characters of 8 bytes. Therefore, employing a comment format allows transmission from the blood glucose measurement device 1801 to the terminal 1903 of the clinical laboratory without changing the existing communication system of a hospital.

Data from each measurement device is received by the terminal 1903 in the clinical laboratory. In this embodiment, since the communication method is the same as in a conventional approach, there is no need for the reception mode of the terminal 1903 in the clinical laboratory to be any different from a conventional mode.

Figure 25:
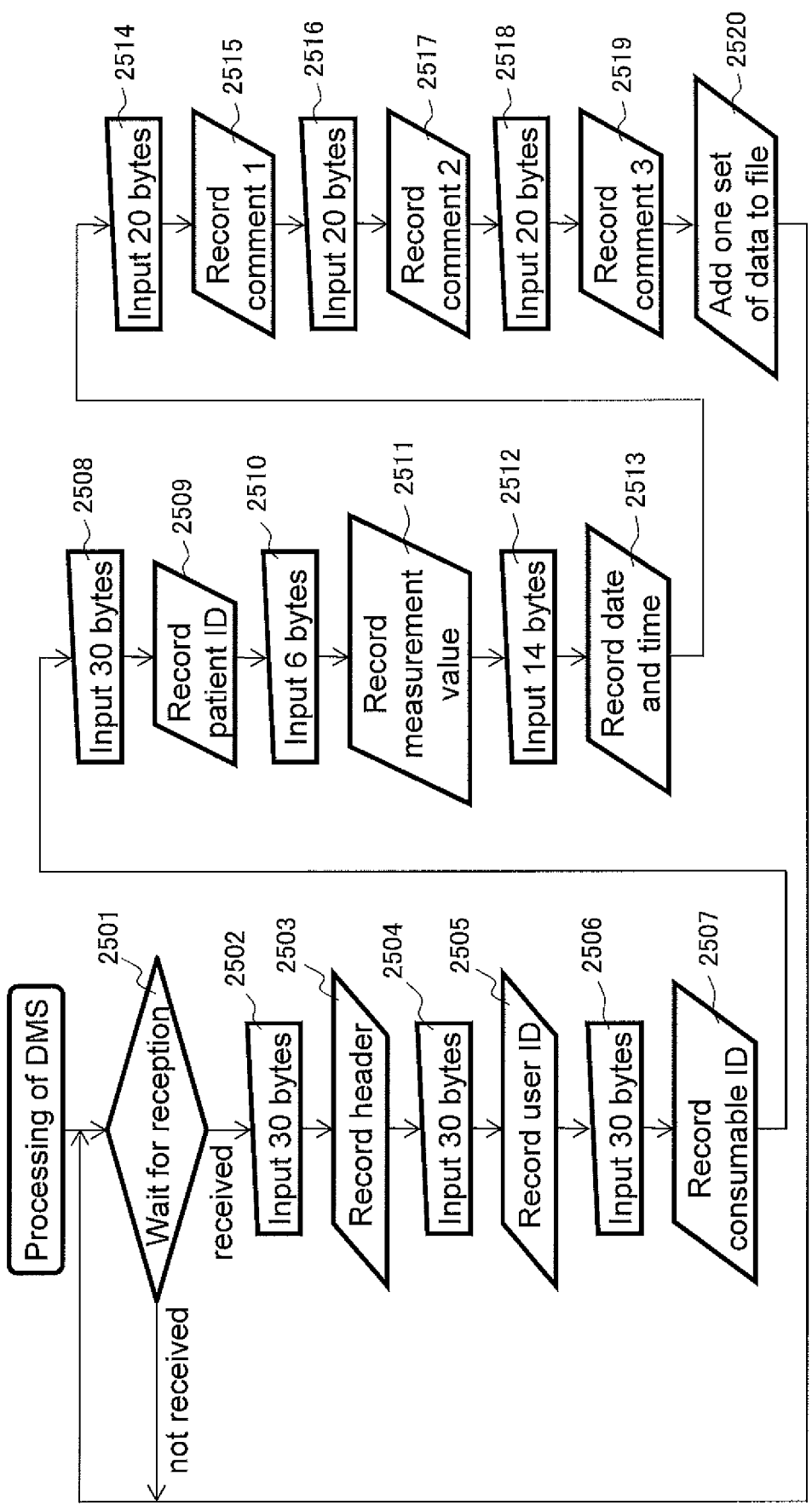
FIG. 25 shows the receiving flow at a typical laboratory terminal.

Accordingly, the reception flowchart of the terminal 1903 of the clinical laboratory shown in FIG. 25 is the same as in prior art. The flow of reception will now be described through reference to FIG. 25.

In FIG. 25, the terminal 1903 of the clinical laboratory continues to wait to receive from the measurement devices in step 2501.

When data has been received, the header information 2301 is received in step 2502, and it is recorded in step 2503.

Next, in step 2504, the user ID 2302 is received, and it is recorded in step 2505.

Similarly, in step 2506, the expendables ID 2303 is received, and it is recorded in step 2507. Then, in step 2508, the patient ID 2304 is received, and it is recorded in step 2509.

In step 2510, the measurement value 2305 is received, and it is recorded in step 2511.

In step 2512, the measurement date and time 2306 are received, and they are recorded in step 2513.

Similarly with the comments, in step 2514 a comment A (2307) is received, and it is recorded in step 2515.

In step 2516, a comment B (2308) is received, and it is recorded in step 2517.

In step 2518, a comment C (2309) is received, and it is recorded in step 2519.

The above process takes care of all the data in one measurement, and in step 2520 this is added to the laboratory terminal output file containing the overall measurement results.

Figure 26:
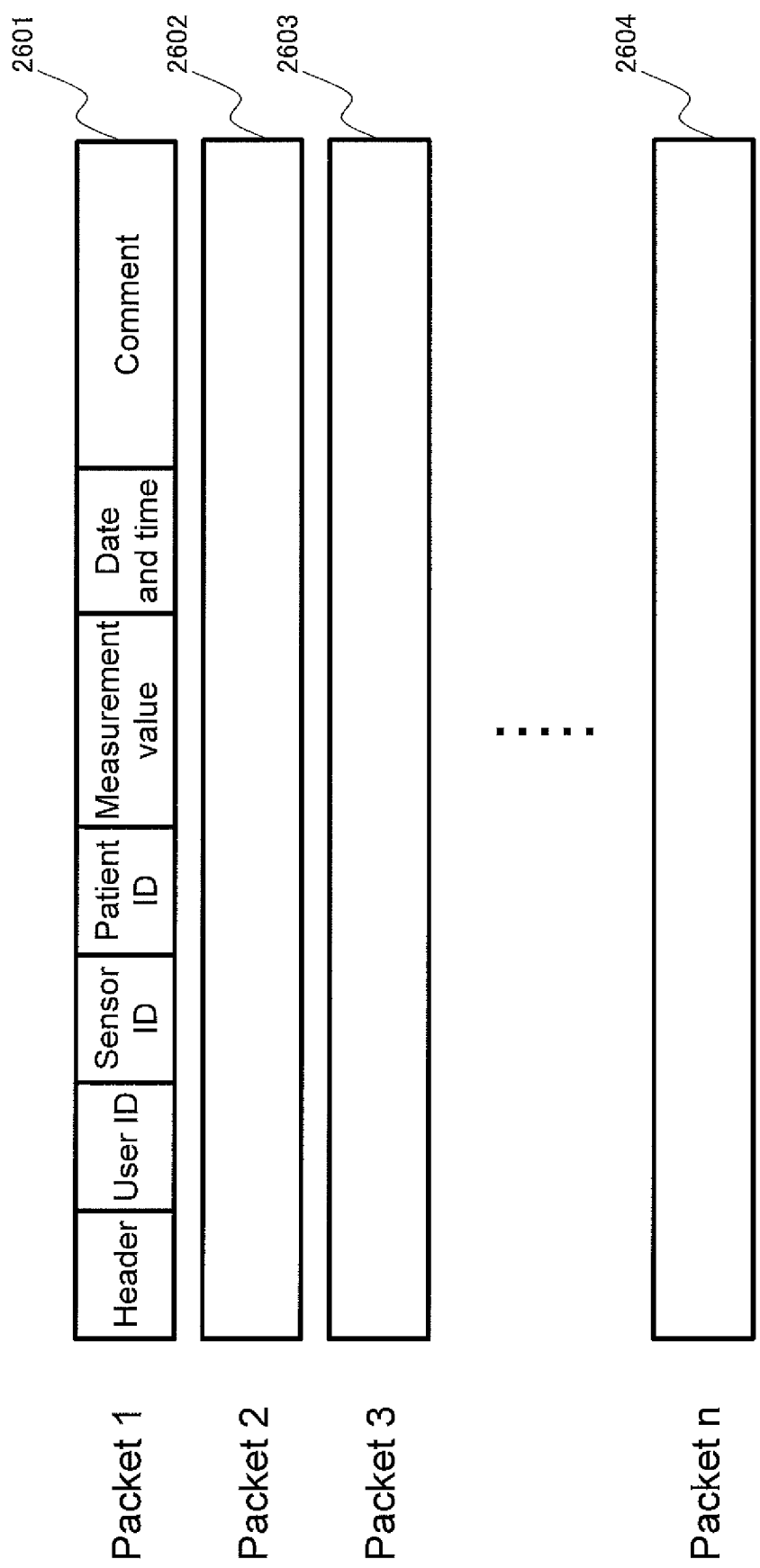
FIG. 26 shows an example of the format of a typical laboratory terminal output file.

FIG. 26 shows the format of the laboratory terminal output file thus produced. This has the same format as that of a conventional file.

2601 to 2604 are packets of the information obtained in each single measurement.

One packet holds various kinds of data for one measurement. The results for n measurements are compiled as a single file.

Measurement data transmitted from all the testing devices in the hospital is compiled into this file. Accordingly, measurement results from something other than the measurement device that is the object of this embodiment, such as a urinalysis apparatus, are also collected as data for this file.

That is, measurement results from various measurement devices are recorded for each packet. Therefore, the type of measurement device, the measurement device ID, and so forth are stored in the header portion, and data indicating which measurement device was used to measure the packet is recorded.

The flow up to the storage of the measurement result and the metric data according to this embodiment in the laboratory terminal output file by the above method was shown. The fact that the collection of metrics, which is a new function, can be performed without any change whatsoever to the communication system on the hospital side is a major effect of this embodiment.

How to produce and make use of evaluation data from the collected metric data will now be described.

Figure 27:
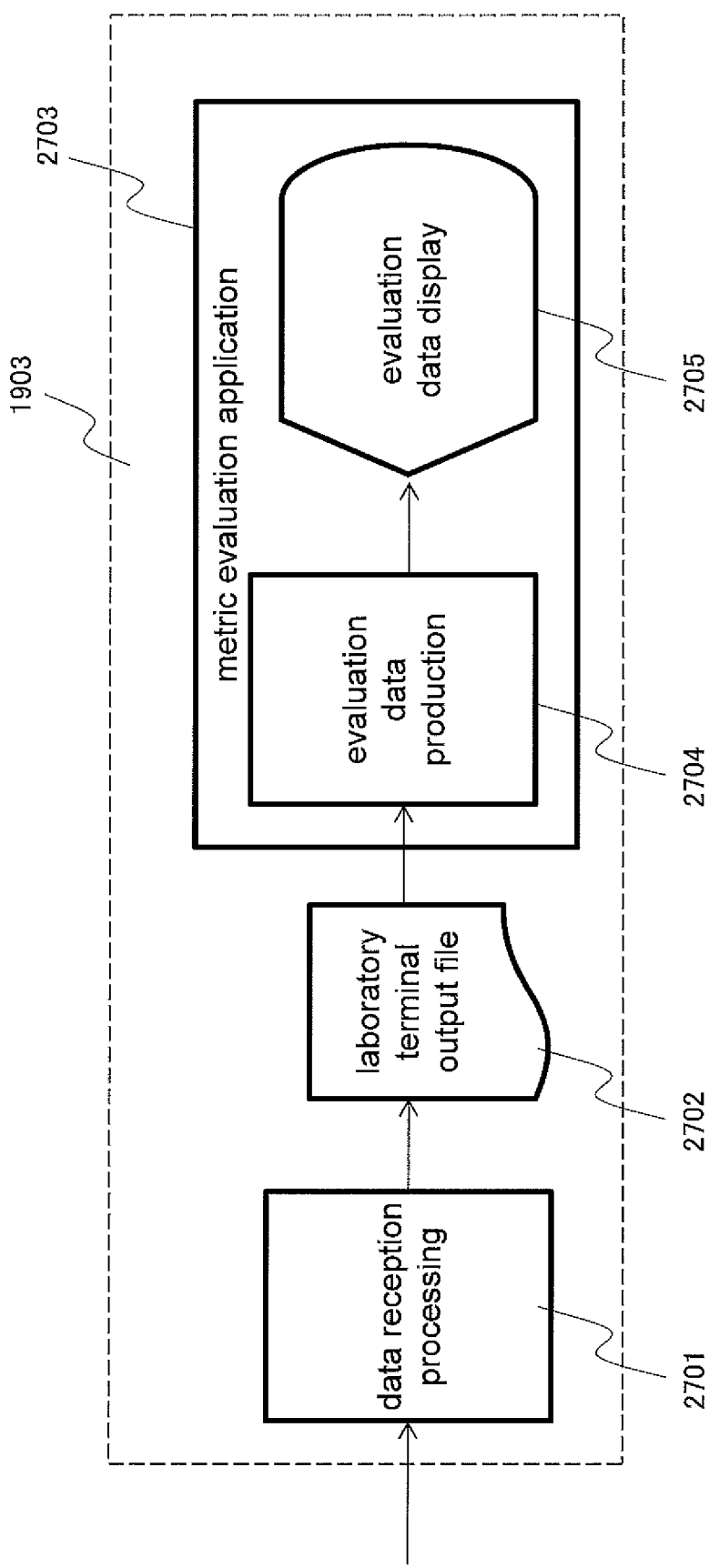
FIG. 27 is a functional block diagram in the laboratory terminal in Embodiment 2 of the present invention.

FIG. 27 is a block diagram of functions in the terminal 1903 of the clinical laboratory.

In FIG. 27, 2701 is the step of data acceptance shown in FIG. 25.

2702 denotes a laboratory terminal output file produced as a result of the data acceptance step 2701, and is shown in FIG. 26. As described above, the data acceptance step 2701 and the laboratory terminal output file 2702 are the same as those used in the past.

In this embodiment, a metric evaluation application 2703 is added to this.

In the metric evaluation application 2703, an evaluation data production step 2704 involves reading the metric data collected by the blood glucose measurement device 1801 according to this embodiment from the laboratory terminal output file 2702, and analyzing the metric data to produce evaluation data.

The evaluation data is displayed on the screen of the terminal 1903 of the clinical laboratory by an evaluation data display 2705, and various kinds of information can be presented to the person in charge of the clinical laboratory.

In the description here, the metric evaluation application 2703 will be described as standalone independent software. However, in the actual operation, the metric evaluation application 2703 may be integrated with the software for collecting data in the terminal 1903 of the clinical laboratory.

Figure 28:
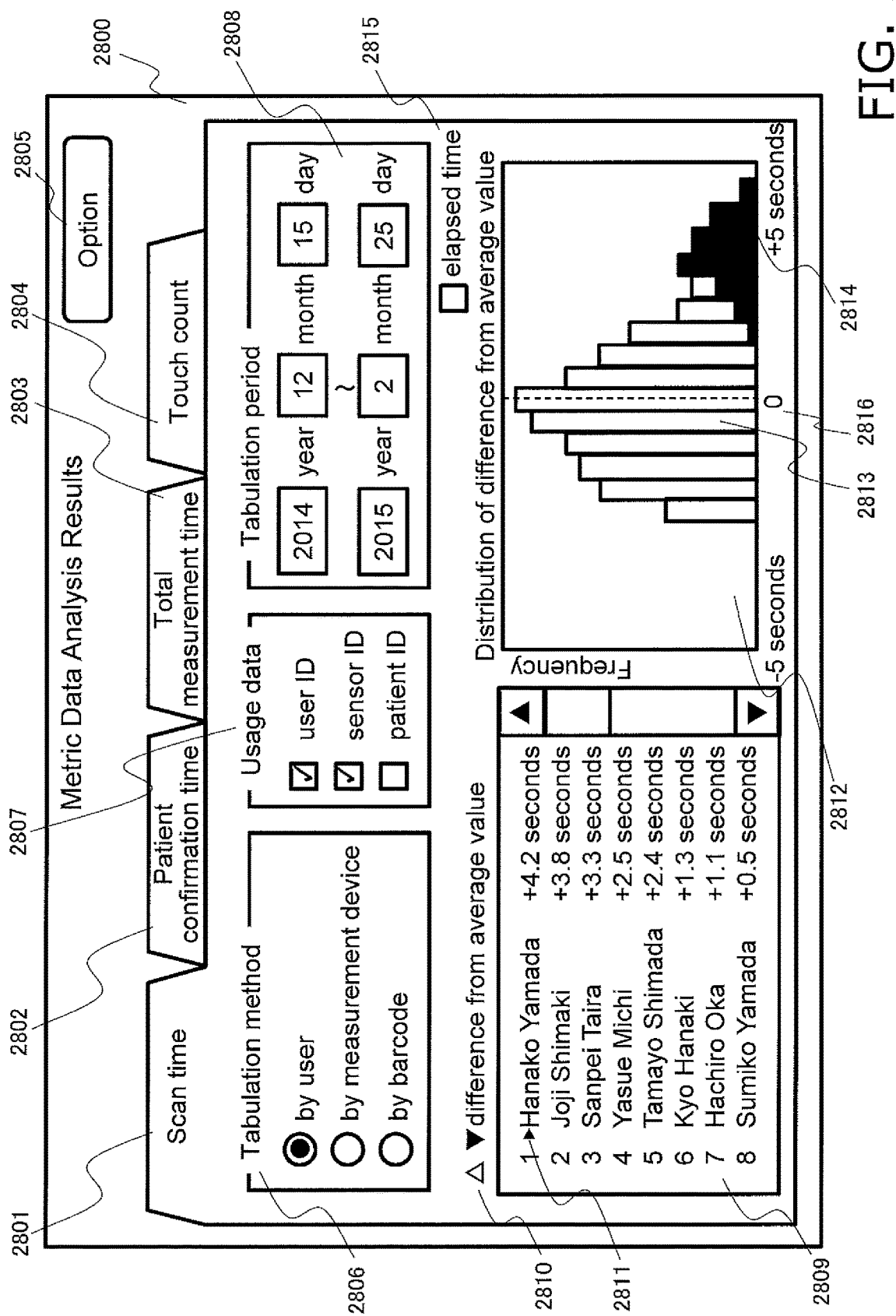
FIG. 28 is a metric evaluation application screen A in Embodiment 2 of the present invention.

FIG. 28 shows an example of a display screen produced by the metric evaluation application 2703.

On this display screen, three types of metric data are utilized, namely, the time required to scan the user ID (metric data 2108), the metric data (measurement of the time) 2109 required to scan the sensor ID, and the metric data (measurement of the time) 2110 required to scan the patient ID, and the results of analyzing the time taken for these scans for each user are shown.

In FIG. 28, 2800 represents the entire display screen. On the screen 2800, the metric data that is to be analyzed is switched by selecting among the four tabs.

2801 is a tab for evaluating the time (metric data 2108 to 2110) required for scanning as metric data. In FIG. 28 this tab 2801 shown as being selected.

2802 is a tab for evaluating the metric data (measurement of the time) 2111 required for patient confirmation as a metric.

2803 is a tab for evaluating the metric data (measurement of the time) 2112 required for the entire measurement as a metric.

2804 is a tab for evaluating the number of screen touches (metric data 2113) required for the entire measurement as a metric.

The option button 2805 is used to display a screen for setting parameters such as various threshold values, or changing the screen display method, such as the scale of a graph display, but details thereof will not be given.

With the tabulation method 2806, it is possible to select from which viewpoint the evaluation is to be performed. If it is by user, then analysis and evaluation are performed focusing on individual users, and this screen shows a case in which the selection is by user. In addition, it is also possible to select an evaluation by measurement device or by barcode.

The usage data 2807 is for selecting the metric data to be used for the evaluation, and the user can select whether to use the time (metric data 2108) required to scan the user ID, the metric data (measurement of the time) 2109 required for scanning the sensor ID, or the metric data (measurement of the time) 2110 required for the patient ID scan, for evaluation.

The tabulation period 2808 designates the period of the metric data used in the evaluation. By default, the entire period over which there is data is displayed, but this can be changed as necessary.

In the ranking table 2809 are listed the differences between the user name and the overall average, in descending order of the difference between the average value for each user and the overall average. In this case, the difference from the overall average of each user in the ranking table 2809 is the quantified skill of each user.

In this ranking table 2809, it is possible to switch between descending order and ascending order by using the descending/ascending order selection button 2810. If a person has a long time displayed in the ranking table 2809, this means that the average time taken for a scan is long, indicating that the person is likely to be unskilled at scanning.

The times required for the scan of a user ID, the scan of a sensor ID, and the scan of a patient ID are all different. For this reason, in finding the difference from the average, it is found for each type, namely, scan of the user ID, scan of the sensor ID, and scan of the patient ID. This calculation method will be described below. As a result, the differential thus found for each user is a part of the evaluation data produced from the metrics that are the times required for the scan (metric data 2108 to 2110).

The distribution graph 2812 shows the difference from the average between all the scan times selected with the usage data 2807, with the horizontal axis being the time differential, and the vertical axis the number of measurements that time differential was encountered (the frequency).

The white histogram 2813 shows the overall distribution, and the black histogram 2814 shows the data of particular users of interest.

The user of interest can be switched by clicking on a user name in the ranking table 2809. The currently selected user of interest has a selection mark 2811 next to it.

By default, the top position of the ranking table 2809 becomes the user of interest, and the situation of the user having the highest probability of having a problem can be confirmed immediately with the black histogram 2814.

For this reason, in the ranking table 2809, the display goes in order from the top, starting with the largest problem.

2816 shows the average value of all the data, and in this case it is the difference from the average, so 0 is the average value.

When there are a large number of people, the frequency of the white histogram 2813 is higher, and the black histogram 2814 relatively indicating individuals becomes extremely low in height, making the distribution more difficult to understand. Therefore, the graph may be drawn so that the scale on the vertical axis is different in the two histograms. These histograms 2813 and 2814 are also evaluation data produced from metric data.

Focusing on what is shown on this screen, the user with the longest average time is Hanako Yamada. Looking at the distribution, the black histogram 2814 is shifted toward a longer time with respect to the white overall histogram 2813.

Consequently, it can be recognized visually that, statistically speaking, the time required for scanning by Yamada Hanako is distributed over a range that is considerably longer compared to the overall average. That is, this screen can be used to confirm the distribution of the time taken for scanning and the average time for each user. Since it is possible to confirm skill by user, measures such as retraining can be adopted for a user who is presumed to be greatly inferior in skill.

Also, if the data used for the usage data 2807 is switched to change the distribution of this histogram, this tells us which ID the user of interest was not good at scanning. As a result, we know what should be emphasized in this user's training.

In the past, there was no way to judge an individual's skill in this way. Accordingly, it was not possible to easily identify a user who needed training.

In FIG. 28, when the elapsed time display check box 2815 is checked, the distribution graph 2812 switches to a diagram showing the elapsed time. The display in this case is shown in FIG. 29.

Figure 29:
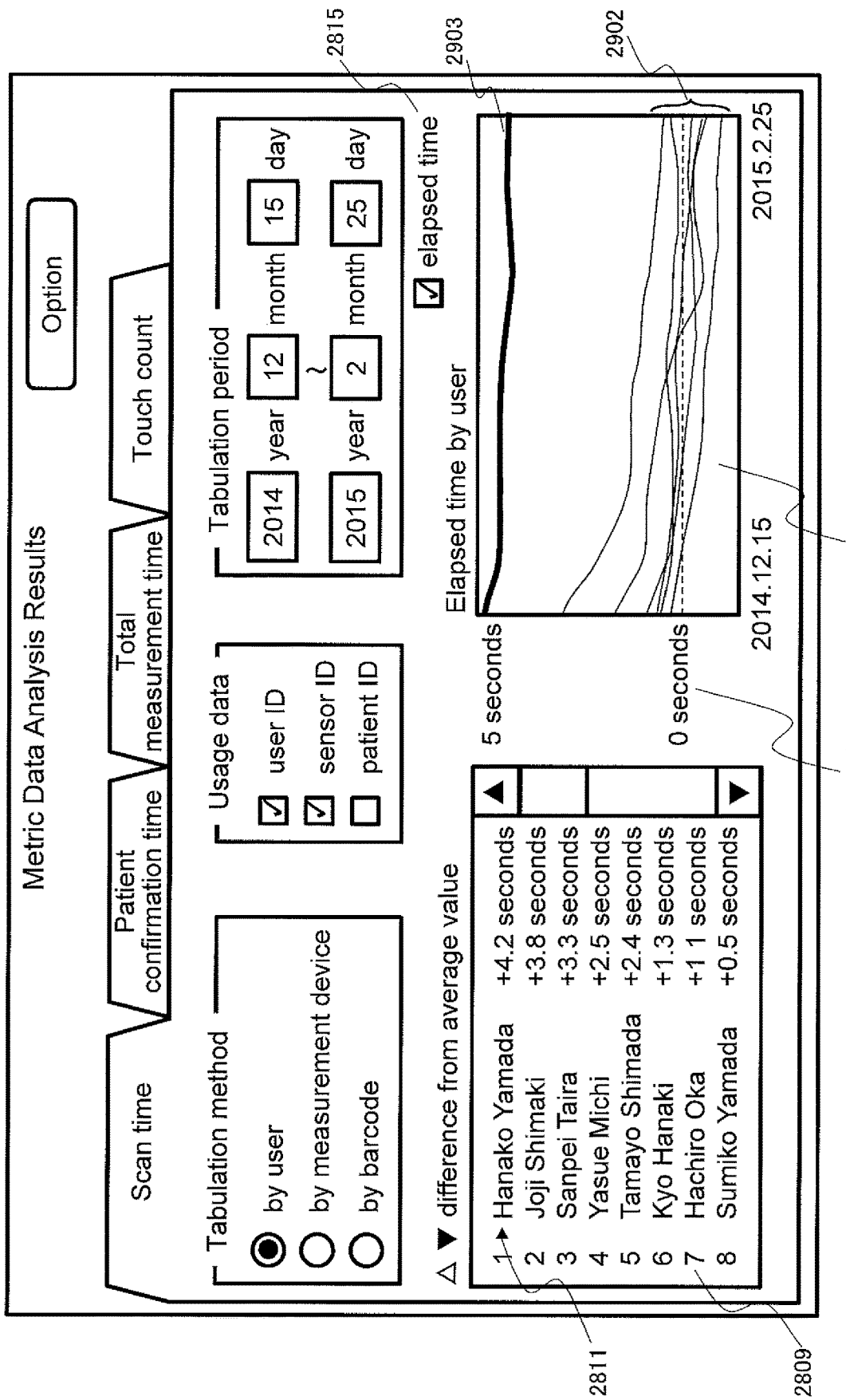
FIG. 29 shows a screen on which is displayed an elapsed time graph in Embodiment 2 of the present invention.

In FIG. 29, only the distribution graph 2812 portion is changed to the elapsed time graph 2901.

In the elapsed time graph 2901, 2902 denotes learning curves by user, and 2903 is the learning curve of a user of interest.

Here, the learning curves 2902 and 2903 are curves obtained by applying a low-pass filter to a plot in which the measurement date and time are on the horizontal axis and the scanning time is on the vertical axis, and show the proficiency of the users. These learning curves 2902 are also evaluation data produced from metric data.

The learning curve 2903 of the user of interest is displayed with a bold line or in a different color to distinguish it from the curves of other users.

Again in the elapsed time graph 2901, as with the distribution graph 2812, the user of interest can be switched by clicking on a user name in the ranking table 2809, and the learning curve 2903 of the user to be viewed can thus be distinguished from the learning curves 2902 of the other users.

2904 shows the average value of all the data. In this case, since it is a difference from the average, 0 is the average value.

In FIG. 29, the learning curve 2903 of the user of interest is slower as of Dec. 15, 2014, and although it does improve somewhat, the learning speed is slower than the learning speed of other users. As a result, it can be seen that there is a considerable difference by Feb. 25, 2015.

As described above, giving a display as shown in FIG. 29 tells us the skill levels of the various users over elapsed time.

Figure 30:
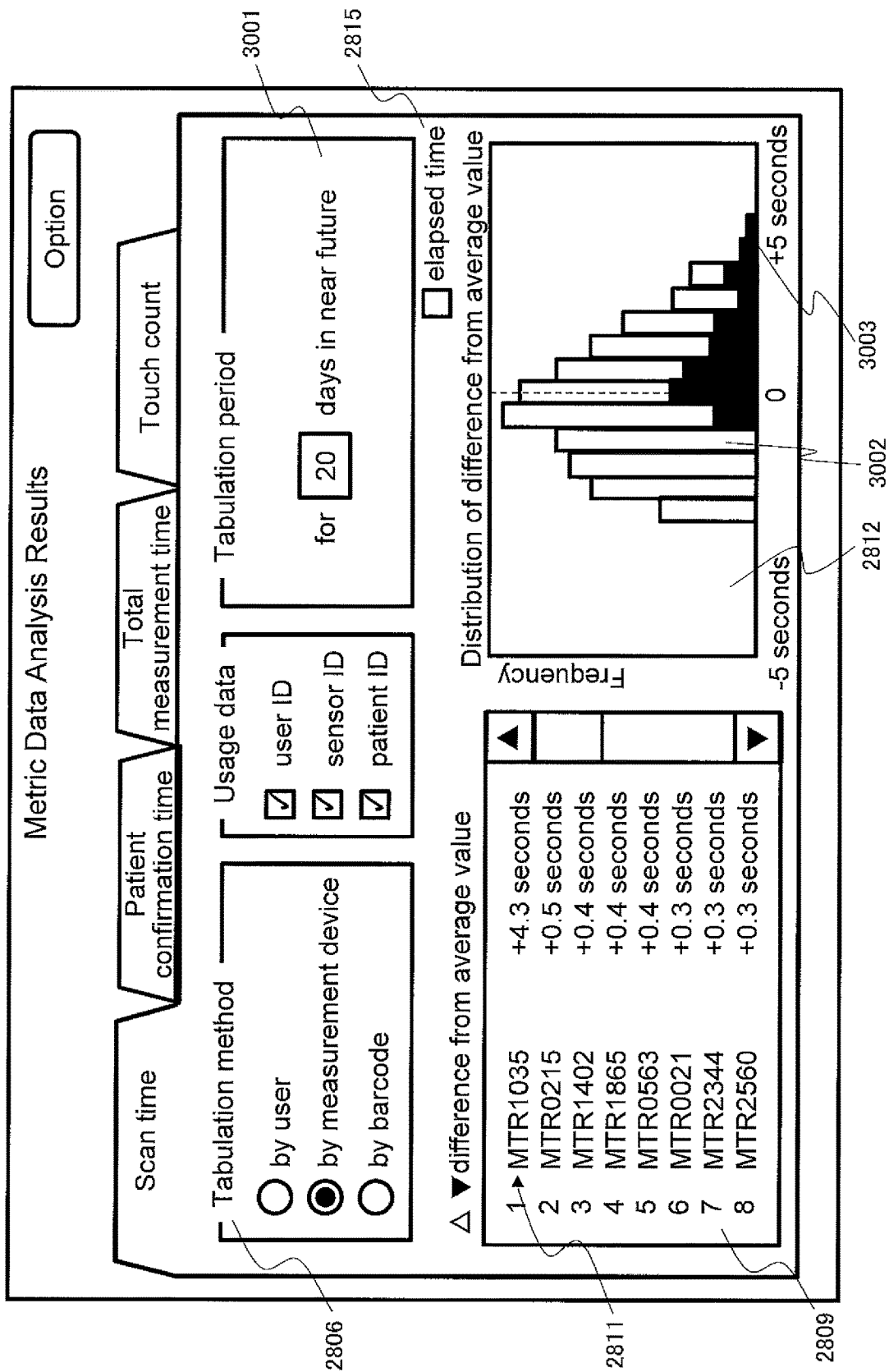
FIG. 30 is a metric evaluation application screen B in Embodiment 2 of the present invention.

On the other hand, FIG. 30 is the screen when the measurement device type has been selected from the tabulation method 2806 in FIG. 28. FIG. 30 is a screen for confirming the time taken for scanning, by measurement device.

In the ranking table 2809 shown in FIG. 30, lists are made in descending order of the difference between the average value for each individual measurement device and the overall average.

If a measurement device has a time listed in the ranking table 2809 that is long, that indicates that scanning takes a long time on average. Therefore, there is a high probability that there is a problem with the scanning function of the measurement device. That is, the ranking table 2809 in FIG. 30 indicates the possibility of soiling or malfunction, such as soiling of the scanning portion or degradation of the light emitting portion, and quantifies the degree of soiling of the measurement device or malfunction of the measurement device.

The distribution graph 2812 shows the difference from the average of all scan times, with the horizontal axis being the time difference, and the vertical axis the number of times this time difference time was encountered (the frequency).

The white histogram 3002 shows the overall distribution, and the black histogram 3003 shows the data for the measurement device of interest.

The device of interest refers by default to the measurement device with the longest average time (MTR1035 in this example), and a selection mark 2811 is added in front of the name in the ranking table. The measurement device of interest can be switched by clicking on the measurement device number portion in the ranking table.

In FIG. 28, the tabulation period 2808 is provided for designating the date and setting the period, whereas in FIG. 30 the tabulation period 3001 is provided for designating the number of days.

This is because malfunction, soiling, and so forth of the measurement devices to be detected on this screen have occurred recently, and if too much past data is included, the desired information becomes buried in the data and difficult to find. Therefore, short-term analysis is preferable, and when analyzing over a short period, the system is switched to a day count input method.

On the display screen shown in FIG. 30, the measurement device with the longest average time is the measurement device MTR1035. A look at this distribution reveals that the black histogram 3003 is shifted to a longer time with respect to whole of the white histogram 3002.

Consequently, it can be visually ascertained that, statistically speaking, the time required for scanning with the measurement device MTR1035 is distributed over a range that is longer considerably than the overall average. In other words, this screen can be used to check the distribution of the time taken for scanning for each measurement device and the average time, and to confirm the sensitivity of each measurement device.

Therefore, measures such as cleaning or repairing can be taken for a measurement device whose sensitivity is deemed to have deteriorated greatly. Conventionally, there was no way to judge the sensitivity of each measurement device as described above, so it came down to a report from the user. As a result, there was a risk that the burden on the user would increase, or maintenance of the device would be overlooked, or that it could not be used in an emergency.

In FIG. 30, when the elapsed time display check box 2815 is checked, the distribution graph 2812 is switched to a diagram showing the elapsed time. The display in this case is shown in FIG. 31.

Figure 31:
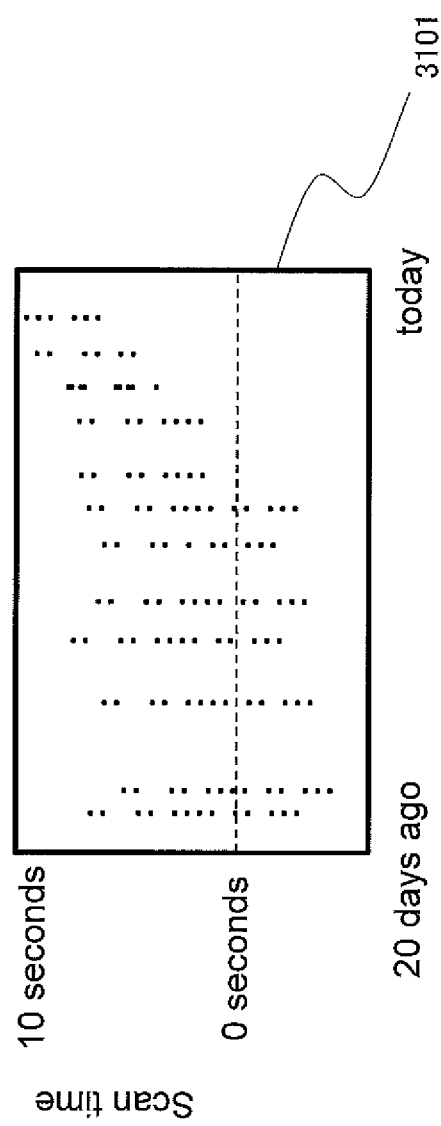
FIG. 31 shows an elapsed time graph screen A in Embodiment 2 of the present invention.

In FIG. 31, only the elapsed time graph 3101 displayed at the position of the distribution graph 2812 in FIG. 30 is shown. This data is the result of plotting all the data for the measurement devices of interest, with the measurement date on the horizontal axis and the scanning time on the vertical axis.

In FIG. 31, the scanning time of the measurement device of interest tends to become longer from several days ago. For this reason, the measurement device of interest will have a pronounced decrease in function due to the effect of soiling, malfunction, etc., several days earlier, and can immediately be scheduled for maintenance inspection.

Figure 32:
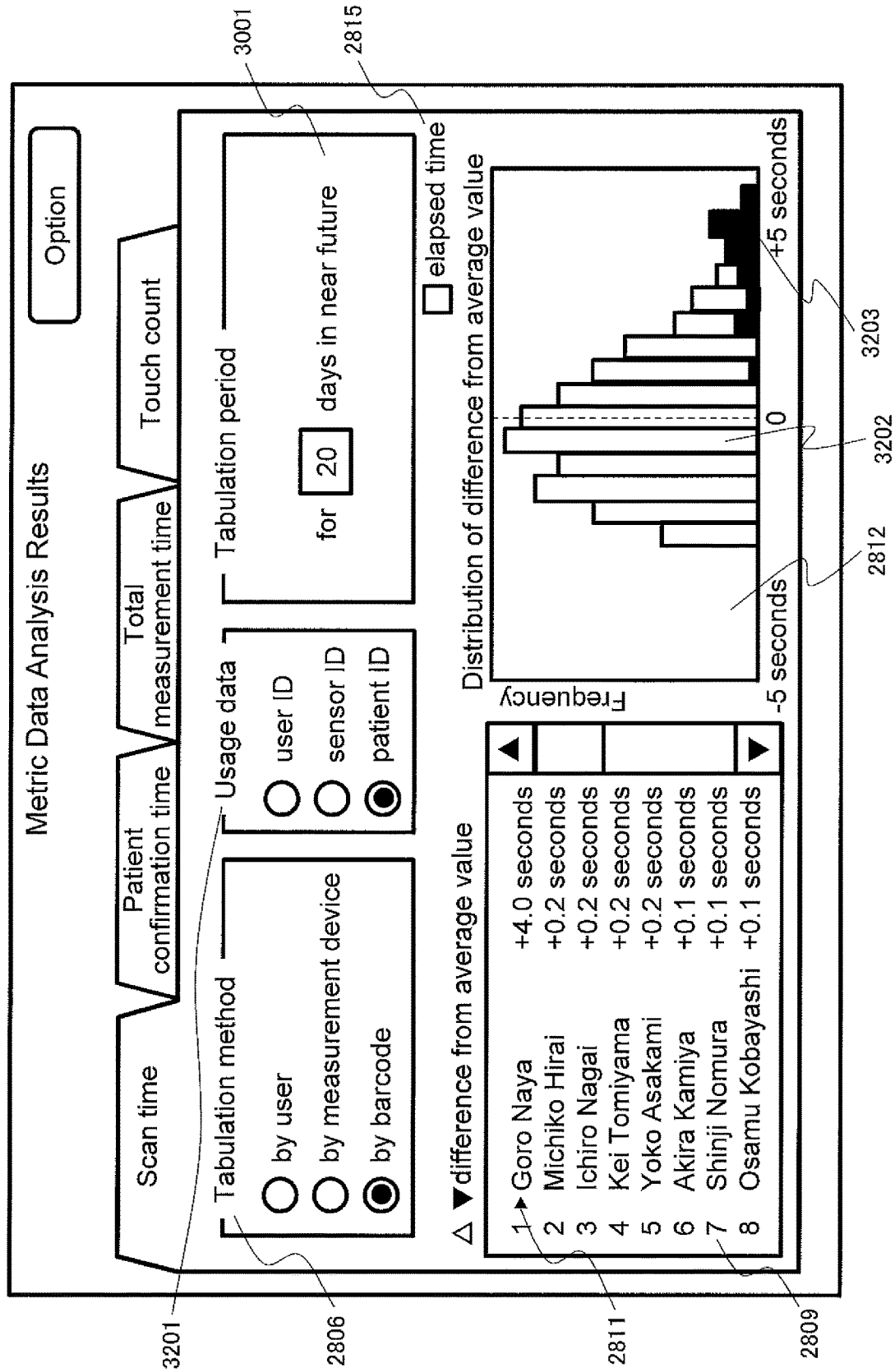
FIG. 32 shows a metric evaluation application screen C in Embodiment 2 of the present invention.

Next, FIG. 32 shows a screen when "by barcode" is selected from the tabulation method 2806 in FIG. 28. FIG. 32 is a screen for confirming the time taken for scanning for each barcode.

The display screen in FIG. 32 allows the user to visually compare the overall distribution and the distribution by barcode for how long the scanning takes.

The usage data 3201 consists of three types: the user ID, the sensor ID, and the patient ID. With the tabulation methods of "by user" and "by measurement device" shown up to this point, a plurality of types of usage data could be selected.

On the other hand, in the case of "by barcode," in order to extract an issue for a particular barcode, the configuration is such that only one type of ID that can be used in the usage data 3201 is selected.

FIG. 32 shows an example of a screen in which a patient ID has been selected, so the time it takes to scan the barcode 204 on the tag 203 of a patient's wrist is analyzed. Also, regarding the tabulation period 3001, a day count designation input method is used that makes it particularly easy to set to a recent short period, so as to facilitate detection of soiling of a barcode or the like.

The ranking table 2809 lists in descending order the difference between the average value for each patient ID barcode and the overall average.

A patient ID barcode with a long time shown in this ranking table 2809 indicates that scanning takes a long time on average. Therefore, there is a possibility that scanning will take longer due to soiling of the barcode or other such causes, or due to the qualities of the individual patient.

That is, the time shown here means the result of quantifying the soundness of a non-contact tag, or the result of quantifying of the compliance of a patient. In this case, if the difference from the average increases when the tabulation time is shortened and the difference from the average decreases when the tabulation time is lengthened, this means that the recent scan times have increased, so there is a high probability that the barcode is dirty.

On the other hand, if the difference from the average is large regardless of the tabulation time, it is highly likely that it is due to the qualities of the individual patient.

Thus, by changing the tabulation period, it is possible to distinguish whether the time indicated here is the result of quantifying the soundness of a non-contact tag or the result of quantifying the compliance of the patient.

The distribution graph 2812 shows the difference from the average of all the scan times selected in "usage data," with the horizontal axis being the time differential, and the vertical axis the number of measurements in which this time differential was encountered (the frequency).

The white histogram 3202 shows the entire distribution, while the black histogram 3203 shows data for the barcode of a patient ID of interest. The black histogram 3203 by default shows the patient ID barcode with the longest average time (in this example, the barcode for Goro Naya), marked with the selection mark 2811 in front of the name in the ranking table 2809.

In the ranking table 2809, it is possible to switch the barcode patient ID of interest by clicking on the patient name portion.

This screen can be used to confirm the distribution of time spent scanning a barcode patient ID and the average time. Therefore, when a patient barcode is checked and the barcode is soiled or faint, the dirt on the patient barcode can be wiped off or the barcode replaced. Also, as a result of checking a plurality of users, if scanning takes more time due to the qualities of an individual patient, this can be conveyed to the nurses.

Conventionally, there was no way to judge the sensitivity of each measurement device as described above. Therefore, it came down to a report from the users, which was a burden on the users.

Although a case of using a barcode was given here as an example, an RF tag or other such non-contact tag may be used instead of a barcode.

Figure 33:
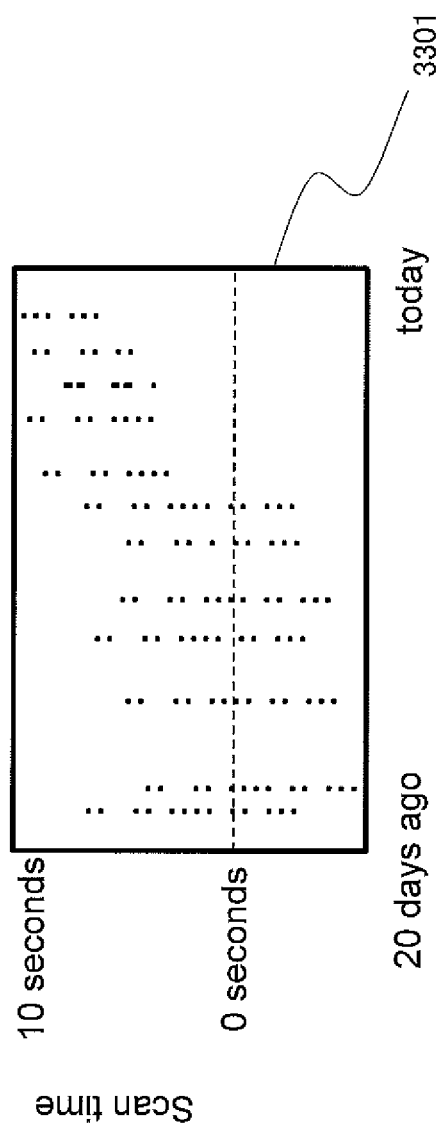
FIG. 33 shows an elapsed time graph screen B in Embodiment 2 of the present invention.

In FIG. 32, when the elapsed time display check box 2815 is checked, the distribution graph 2812 switches to FIG. 33 showing the elapsed time.

In FIG. 33, only the elapsed time graph 3301 displayed at the position of the distribution graph 2812 in FIG. 32 is shown. The data shown in FIG. 33 is obtained by plotting all the data of the measurement devices of interest, with the measurement date on the horizontal axis and the scanning time on the vertical axis.

In FIG. 33, it can be seen that while the difference from the overall average was distributed around 0 at the outset, it there is a tendency to be considerably longer starting a few days ago. In such a case, there is a high probability that the barcode became soiled a few days ago.

Figure 34:
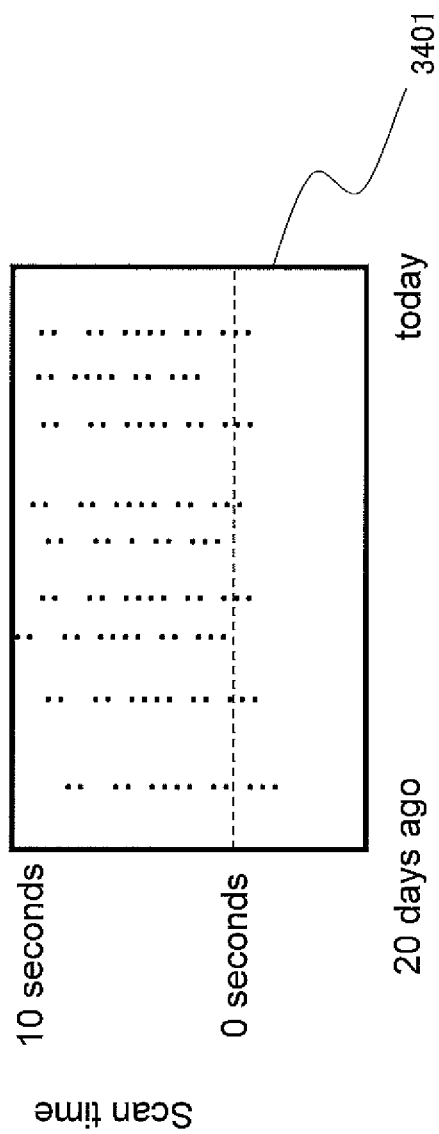
FIG. 34 shows an elapsed time graph screen C in Embodiment 2 of the present invention.

Also, in the elapsed time graph 3401 shown in FIG. 34, since the time has always been long right from the beginning, it can be concluded that it takes more time to scan due to the qualities of individual patients, except when the barcode is dirty from the beginning. Therefore, the nurses can be urged to take extra care in this case.

The example given above was of the evaluation data display 2705 produced by the metric evaluation application 2703 when three types of metric data were used: the time required to scan the user ID (metric data 2108), the metric data (measurement of the time) 2109 required to scan the sensor ID, and the metric data (measurement of the time) 2110 required to scan the patient ID.

Although only the scan times are used as metric data, these can be used to produce evaluation data from a number of angles, making it possible to imagine many different situations, such as the user's skill level, device malfunction, barcode soiling, and qualities of the patient.

Next, an example of clicking on the patient confirmation time tab 2802 in FIG. 28 will be described through reference to FIG. 35.

Figure 35:
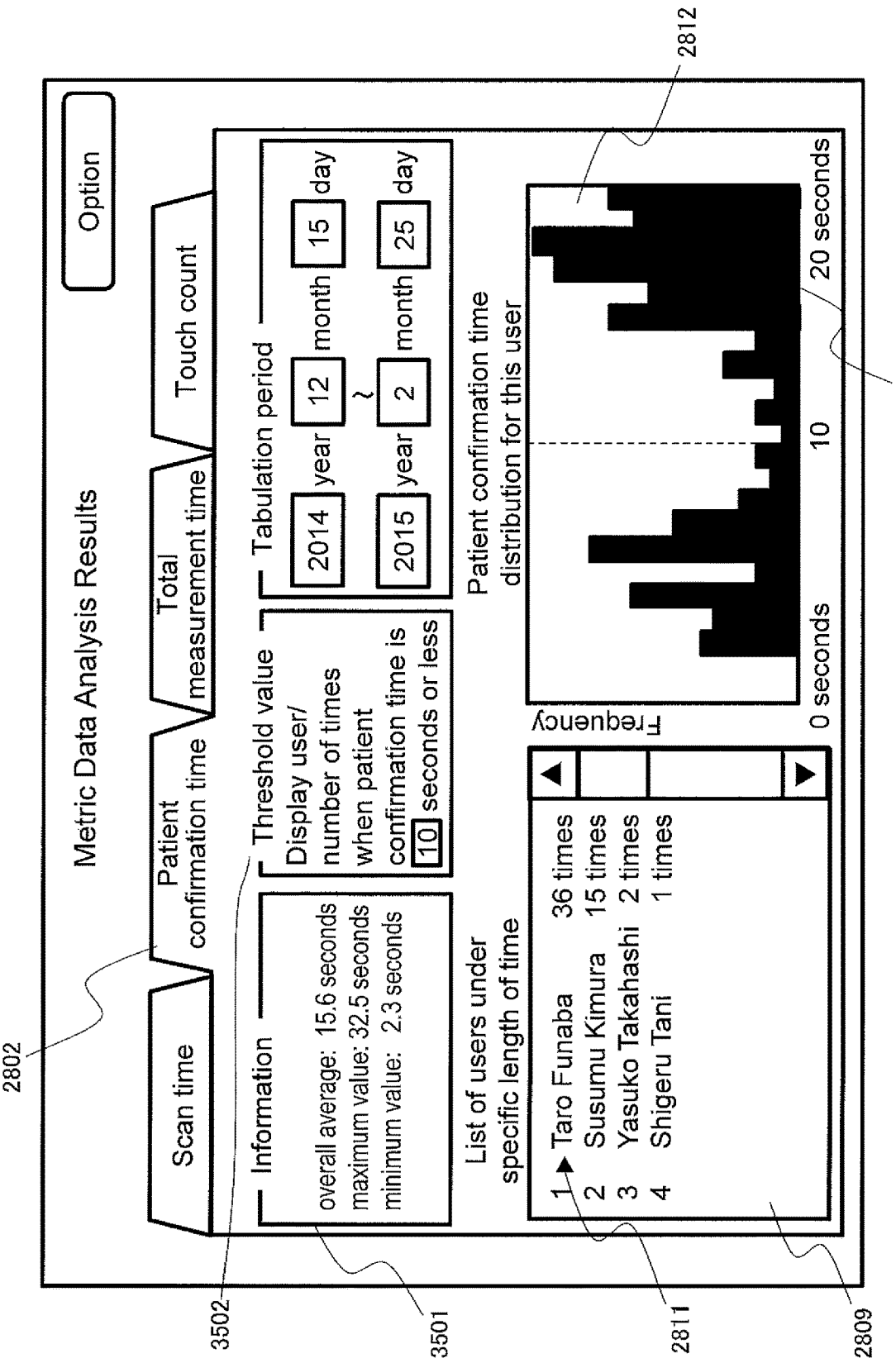
FIG. 35 shows a metric evaluation application screen D in Embodiment 2 of the present invention.

FIG. 35 is a screen displaying evaluation data in the case of using the metric data (measurement of the time) 2111 required for patient confirmation as metric data. This screen can be checked to confirm the time spent for patient confirmation by user.

In a hospital, the staff is obliged to confirm a patient's identity in order to avoid accidentally mistaking one patient for another. Patient confirmation is displayed on the screen in the form of the scanned patient name, date of birth, and so forth after the patient ID has been scanned. Therefore, at this stage the user asks the patient to state his or her name, date of birth, and so forth, confirms whether that information matches what is displayed on the screen, and at the same time, the user confirms the age, sex, and the like visually (step 2213 in FIG. 22).

In FIG. 35, the average value, maximum value, and minimum value for the entire data are displayed on the information display component 3501, and the overall tendency is confirmed.

The shortest time that it should take for patient confirmation time is inputted to the threshold designation component 3502. Patient confirmation usually takes about 15 seconds, so 10 seconds is set as the threshold value here. Therefore, users whose patient confirmation times are shorter than 10 seconds are displayed. Also, as with the previous example, the tabulation period 2808 can also be set.

In the ranking table 2809, the names of users whose confirmation times are below the threshold value are listed in descending order of the number of times they were below the threshold value. This ranking table 2809 shows the number of times that the time required for patient confirmation was extremely short. Thus, the ranking table 2809 shows users who are highly likely not to confirm a patient sufficiently.

Also, the number of times in the ranking table 2809 is obtained by quantifying the measurer's awareness of rule compliance.

In the distribution graph 2812, the vertical axis is the frequency and the horizontal axis is the time taken for patient confirmation, and the distribution of the patient confirmation times of the user of interest is shown in the black histogram 3503.

Unlike in the previous examples, the entire histogram is not displayed here. The user whose distribution is indicated here (in this example, Taro Funaba) is by default the user with the highest number of times, and the selection mark 2811 is added in front of the name in the ranking table 2809.

The user of interest in the ranking table 2809 can be switched by clicking on the name portion.

Since the number of times blood glucose is measured varies from one user to the next, there will be times when the frequency of deviation from the rules cannot be compared simply by the number of times between users with many measurements and users with few.

In such a case, the tendency may be made easier to perceive by changing the scale on the vertical axis of the distribution graph 2812 for each user of interest. In this case, the tendency can be confirmed more easily by setting the vertical axis to the ratio to the total number of measurements of the user of interest, rather than the number of measurements.

As described above, using the screen shown in FIG. 35 allows the distribution of time spent on patient confirmation to be confirmed for each user. Furthermore, it is possible to identify users who may be neglecting patient confirmation. Measures such as giving a warning and re-implementing training can be taken for any identified users.

Conventionally, it was difficult to evaluate whether or not patient confirmation was being carried out properly because there was no way to confirm how long each user was spending on patient confirmation.

Figure 36:
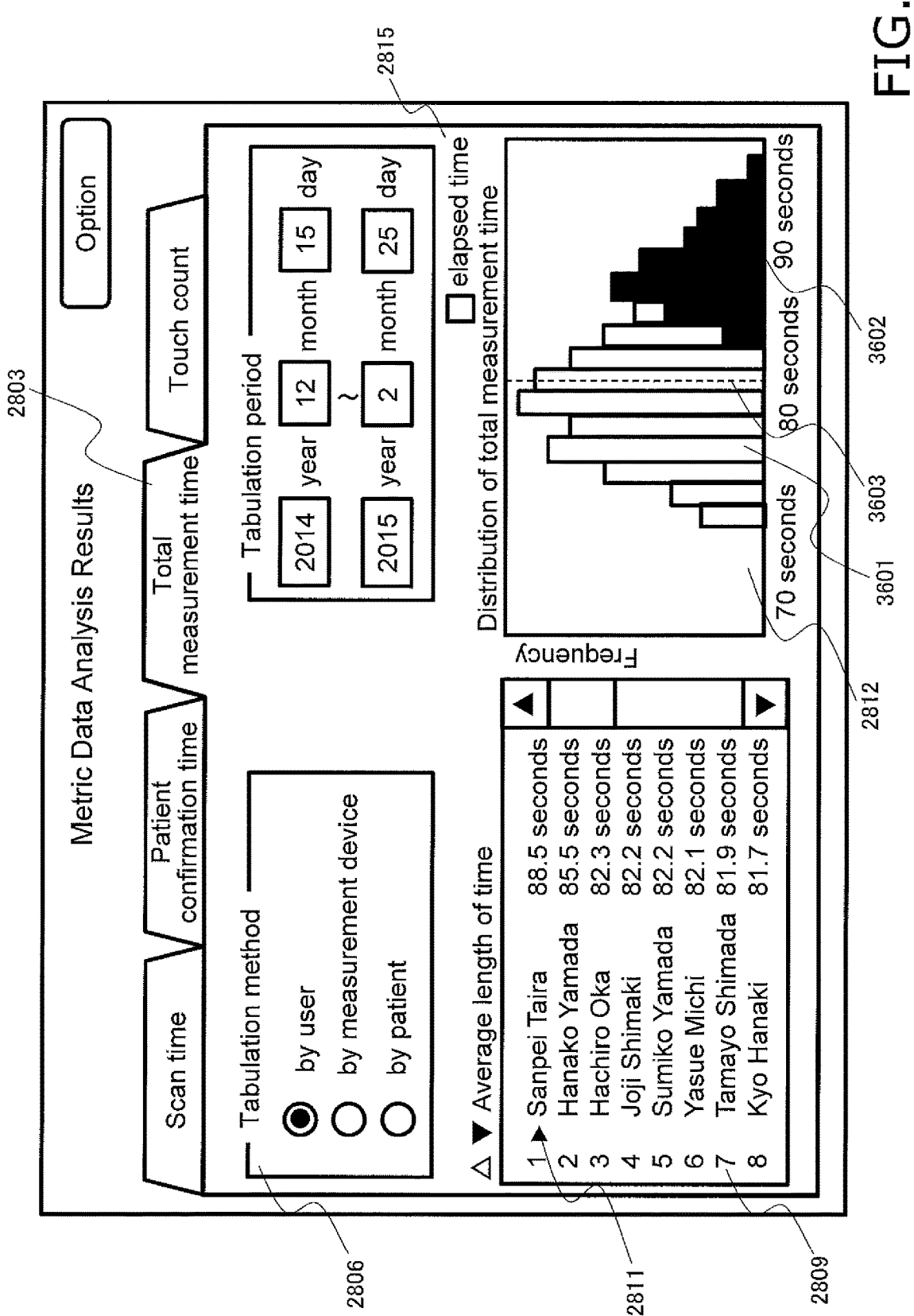
FIG. 36 shows a metric evaluation application screen E in Embodiment 2 of the present invention.

When the total measurement time tab 2803 in FIG. 28 is clicked on, the screen shown in FIG. 36 is displayed.

FIG. 36 is a screen displaying evaluation data when the metric data (measurement of the time) 2111 required for all measurements is used as metric data. Checking the screen in FIG. 36 makes it possible to confirm the time required for the measurement for each user.

FIG. 36 is almost the same as FIG. 28. In FIG. 28, however, there are three types of scan time as metric data, so data can be selected with the usage data 2807. On the other hand, in FIG. 36, the metric data is just one type, namely, the total measurement time, so there is no usage data 2807.

Also, in FIG. 28, the evaluation data displayed on the screen was represented by the difference from the average value of all users. In FIG. 36, the evaluation data is displayed on the basis of times that were actually measured.

In the ranking table 2809 in FIG. 36, the by-user average values of all measurement times are listed in descending order. Users with longer times shown in this table take longer on average to measure blood glucose, which means that the efficiency of those users is likely to be poor.

The distribution graph 2812 shows a histogram of all the measurement times, in which the horizontal axis is the measurement time and the vertical axis is the frequency of measurement. The white histogram 3601 shows the entire distribution, and the black histogram 3602 shows the data for the user of interest.

For reference, the overall average value is indicated by a dotted line (3603). The user of interest can be switched by clicking on the user name portion in the ranking table 2809.

Also, when the elapsed time display check box 2815 is checked, a learning curve is displayed. This is the same as the elapsed time graph 2901 in FIG. 29, so it will not be described again here.

Furthermore, it is possible to switch between performing the evaluation for each measurement device or for each patient can be switched by using the tabulation method 2806 in FIG. 36. This part is similar to that in FIGS. 30 and 32, and therefore will not be described again.

With the above method, when evaluating for each measurement device, it is possible to detect the sensitivity of the touch panel, as well as any soiling stain of the scanner or other such abnormalities in the measurement device. Also, when evaluating by patient, it is possible to issue advice about how to deal with patient problems, such as when it is difficult to collect blood, or when there are problems in the qualities of individual patients.

Thus, there is only one type of metric data, the metric data (measurement of the time) 2111 required for the entire measurement, but many different problems, such as problems with the user, the measurement device, and the patient, can be detected by producing evaluation data from different angles.

Also, by comparing the patient-specific evaluation results produced by this function with the results by patient barcode shown in FIG. 32, it is possible to surmise whether the problem is in the patient himself or in the patient's barcode.

Figure 37:
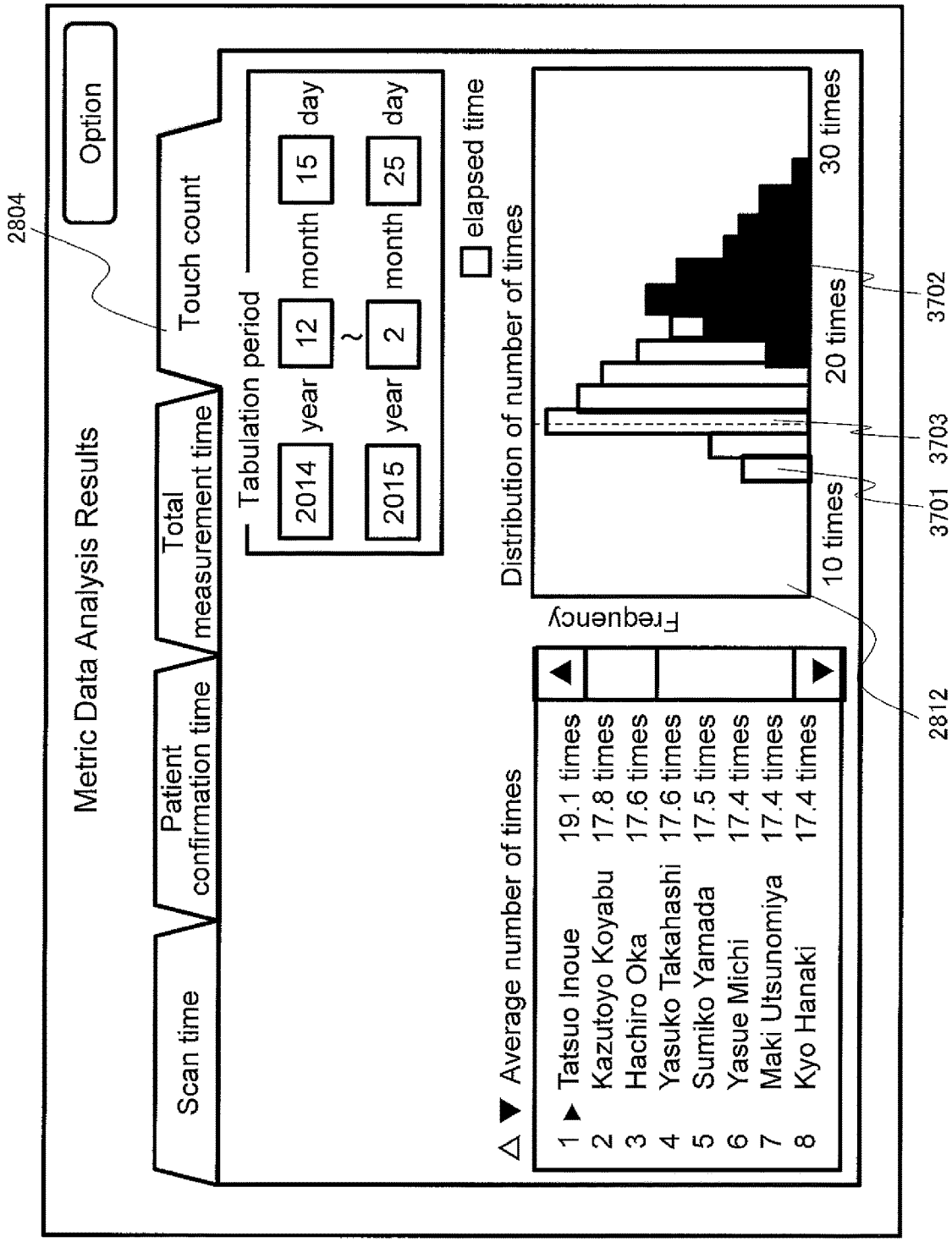
FIG. 37 shows a metric evaluation application screen F in Embodiment 2 of the present invention.

In FIG. 28, when the number of touches 2804 is clicked on, the screen shown in FIG. 37 is displayed.

FIG. 37 is a screen displaying evaluation data when the number of screen touches (metric data 2113) required for the entire measurement is used as the metric data. The screen in FIG. 37 can be used to confirm the number of screen touches required for measurement for each user.

The display screen in FIG. 37 is similar to FIG. 36, but compared with FIG. 36, since the number of screen touches (metric data 2113) required for the entire metric data measurement is related to the skill of the user, there is no tabulation method 2806, and only the evaluation results by user are displayed.

Also, the units in the display are the number of times rather than the number of seconds. In FIG. 37, the distribution graph 2812 shows a histogram of the number of touches, in which the horizontal axis is the number of times and the vertical axis is the frequency. The white histogram 3701 shows the overall distribution, and the black histogram 3702 shows the data of the user of interest.

For reference, the overall average value 3703 is indicated by a dotted line. This display is useful in judging the need for training because it tells us which users have been performing screen operations more than necessary in measurement.

The evaluation data display 2705 in this embodiment was described above, and now we will describe the processing involved in the evaluation data production step 2704 for achieving this display.

Figure 38:
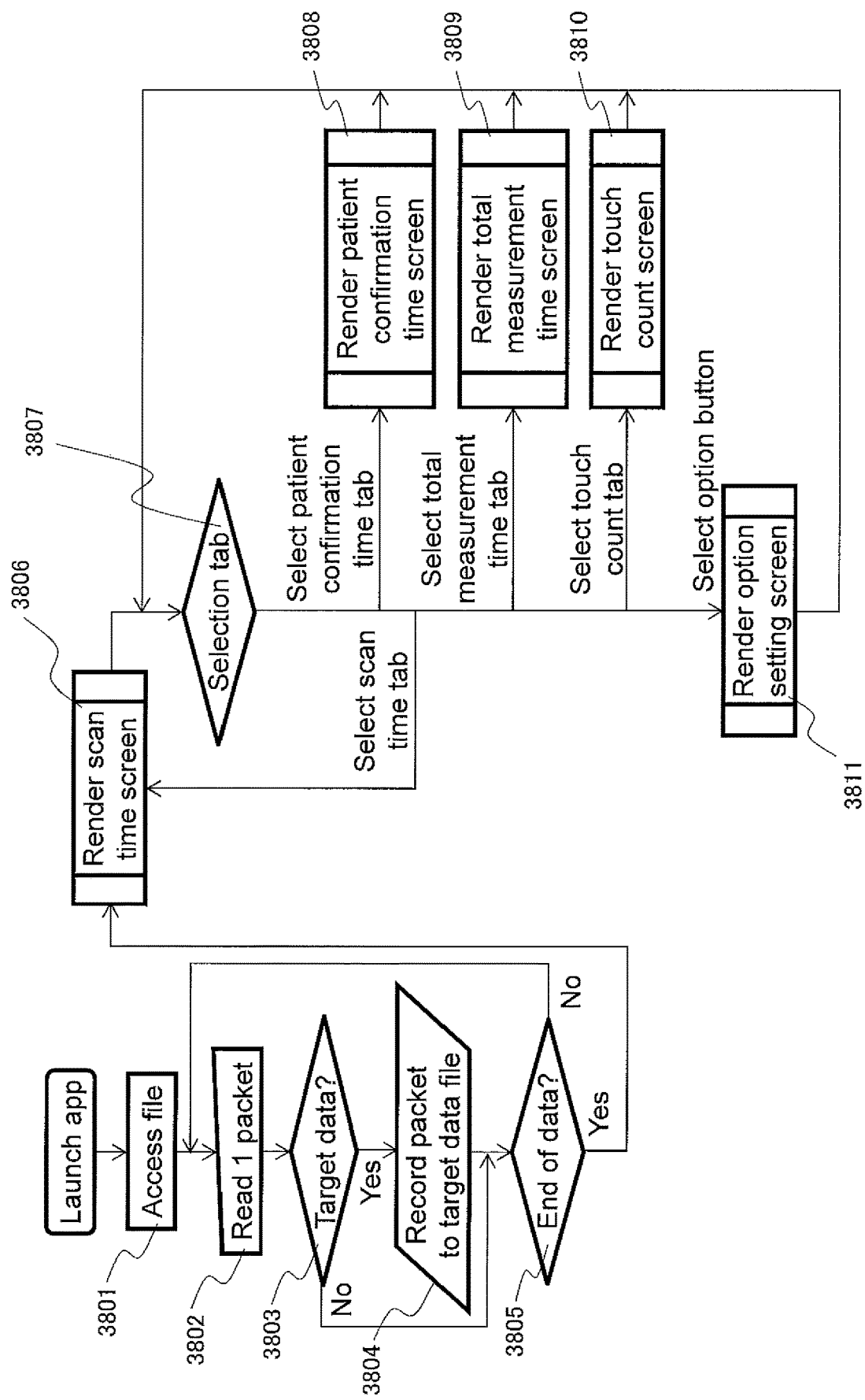
FIG. 38 shows the processing main flow of a metric evaluation application in Embodiment 2 of the present invention.

FIG. 38 is a flowchart of the main step in the metric evaluation application 2703.

After launching the application, in step 3801 the laboratory terminal output file 2702 is accessed, and the necessary information is sequentially read out from this file.

First, in step 3802, one packet is read from the file.

In step 3803, it is determined whether or not this was produced by the blood glucose measurement device 1801. This determination is made by examining the measurement device ID of the header portion.

Here, in the case of a packet produced by the blood glucose measurement device 1801, this is recorded as a target data file in step 3804.

On the other hand, if it is not a packet produced by the blood glucose measurement device 1801, it is not recorded.

In step 3805, it is checked whether all the packets in the laboratory terminal output file 2702 have been checked.

Here, if all the checks are not completed, the flow returns to step 3802 and reading is repeated.

In step 3806, when all the packets in the laboratory terminal output file 2702 have been checked, that means that all the data produced by the blood glucose measurement device 1801 has been stored in the target data file, so the actual processing is started.

After the processing begins, first, as default processing, in step 3806 a scan time screen is drawn, and the screen shown in FIG. 28 is displayed.

After that, when the selection tab is clicked on, classification is performed in step 3807. Here, the processing of steps 3806 to 3810 is performed according to which tab was clicked on, and either FIG. 28, FIG. 35, FIG. 36, or FIG. 37 is displayed according to the processing.

When the option button 2805 is clicked on, processing to display the option setting screen is performed in step 3811.

Next, a processing example of when the results of analyzing the scan time are displayed in step 3806 will be described through reference to FIG. 39.

Figure 39:
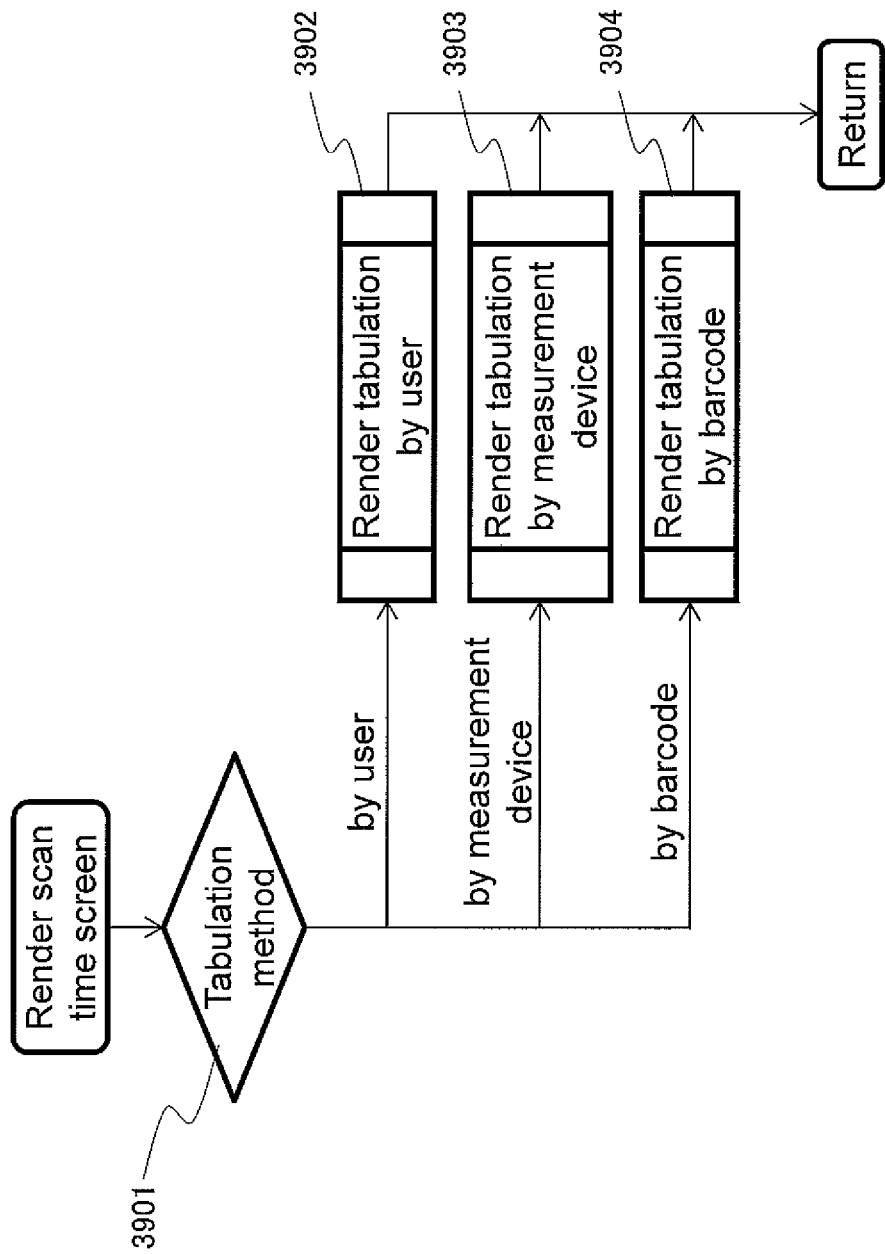
FIG. 39 shows the scan time screen drawing processing flow in Embodiment 2 of the present invention.

FIG. 39 is a processing flowchart of step 3806 for drawing a scan time screen.

In FIG. 39, in step 3901 the processing is switched depending on which tabulation method 2806 in FIG. 28 has been chosen.

When by-specific has been selected in the tabulation method 2806, by-user tabulation drawing 3902 is executed, when by-device has been selected, by-device tabulation drawing 3903 is executed, and when by-barcode has been selected, by-barcode tabulation drawing 3904 is executed.

The method for producing the evaluation data and the flow of processing for the actual drawing will be described through reference to FIG. 40, using step 3806 of performing scan time screen drawing as an example.

Figure 40:
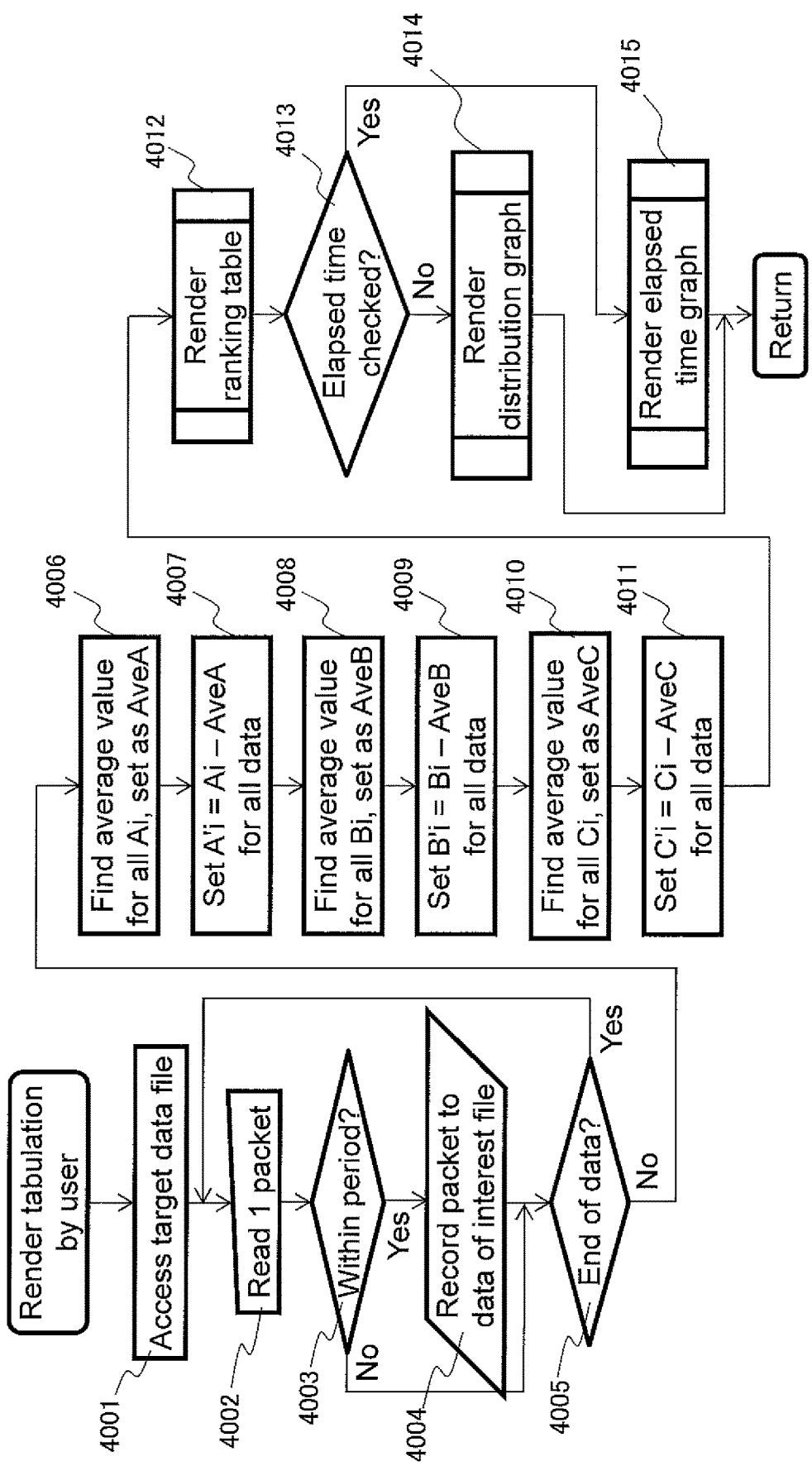
FIG. 40 shows the user counter drawing processing flow in Embodiment 2 of the present invention.

FIG. 40 is a processing flowchart of step 3806 of performing scan time screen drawing.

In step 4001, the target data file produced in FIG. 38 is accessed.

In step 4002, one packet of data is read.

In step 4003, since the date and time of measurement are recorded in the packet, they are read and compared with period set with the tabulation period 2808 in FIG. 28. Here, if it is within the period, this packet is recorded as the data file of interest in step 4004.

In step 4005, it is checked to see whether or not all of the target data file has been read, and if data still remains, step 4002 and below is repeated.

If all the data in the object data file is processed, the flow proceeds to processing of the target data file.

The packet structure of the data file of interest is the same as before. If we let n be the total number of packets, the i-th packet includes the user (ID data Ui), the time required to scan the user ID (data Ai), the time required to scan the sensor ID (data Bi), and the time required to scan the patient ID (data Ci).

As described above, the time required to scan must be compared to the difference from the average value, instead of comparing to the absolute value, so here the difference from the average value is found.

To this end, first, in step 4006, the average value is found for n pieces of data Ai, and this is termed AveA. Next, in step 4007, Ai-AveA values are successively found for all n pieces of Ai, and these are termed A'i. Consequently, A'i is the difference from the average value.

Similarly, in step 4008, the average value is found for n pieces of data Bi, this is termed aveB, and in step 4009, Bi-aveB values are successively found for all of Bi, and these are termed B'i.

Furthermore, in step 4010, the average value of n pieces of data Ci is found, and this is termed AveC. Then, in step 4011, Ci-AveC values are successively found for all of Ci, and these are termed C'i.

In step 4012, this data is used to produce the ranking table 2809.

In step 4013, the elapsed time display check box 2815 in FIG. 28 is examined to see whether or not it has been checked. If there is no check, a distribution graph 2812 is produced in step 4014, and if there is a check, an elapsed time graph is produced in step 4015.

Figure 41:
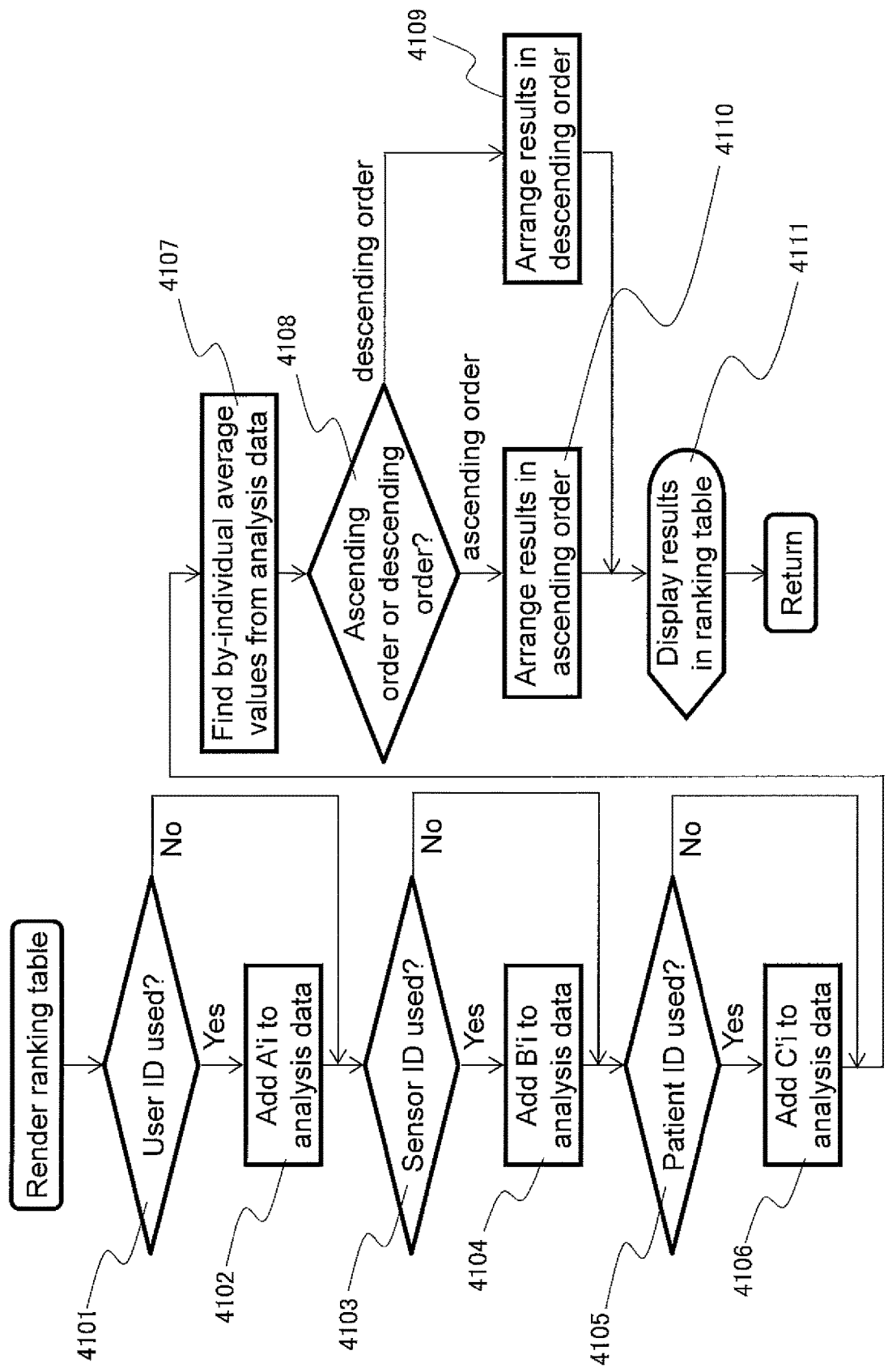
FIG. 41 shows the drawing processing flow for a ranking table in Embodiment 2 of the present invention.

FIG. 41 is a flowchart of a step 4012 for producing a ranking table 2809.

In step 4012, first, analysis data is prepared according to whether A'i, B'i, or C'i will be used in the analysis of data.

In step 4101, the usage data 2807 in FIG. 28 examined to see whether or not the user ID has been selected. If the user ID has been selected, A'i is added to the analysis data in step 4102.

Similarly, in step 4103, the usage data 2807 in FIG. 28 is examined to see whether or not the sensor ID has been selected. If the sensor ID has been selected, in step 4104 B'i is added to the analysis data.

Furthermore, in step 4105, the usage data 2807 in FIG. 28 is examined to see whether or not the patient ID has been selected. If the patient ID has been selected, in step 4106 C'i is added to the analysis data.

In step 4107, the by-individual average values are found from the analysis data.

In step 4108, the descending/ascending order selection button 2810 in FIG. 28 is switched, and it is determined whether the order is descending or ascending. If the order is descending, in step 4109 the by-individual average values are sorted in descending order. On the other hand, if the order is ascending, in step 4110 the by-individual average values are sorted in ascending order.

In step 4111, the result of this sorting is displayed in the ranking table 2809 of FIG. 28.

Figure 42:
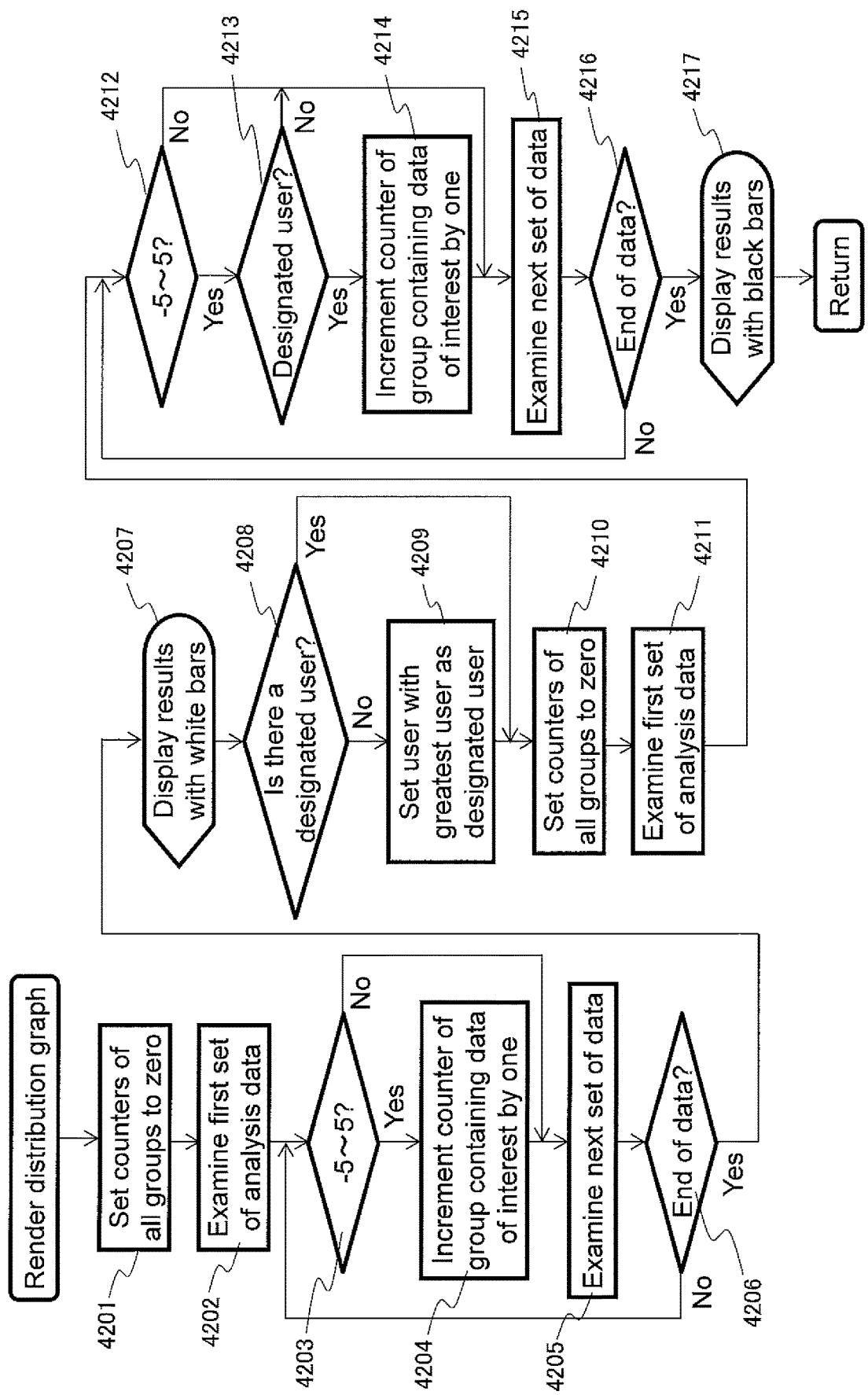
FIG. 42 shows the drawing processing flow for a distribution graph in Embodiment 2 of the present invention.

Next, the flow of step 4014 for drawing the distribution graph 2812 will be described through reference to FIG. 42.

In order to render the distribution graph 2812, it is first necessary to produce the data of the histogram.

In this histogram, the horizontal axis shows the groups, and the vertical axis shows the number of elements in each group.

The groups are formed by quantifying the difference from the average value every 0.5 second, for example. In the first group the difference from the average value is at least −5.0 seconds and less than 4.5 seconds, in the second group the difference from the average value is at least −4.5 seconds and less than 4.0 seconds, . . . , in the eleventh group the difference from the average value is at least 0.0 seconds and less than 0.5 seconds, . . . , and in the twentieth group the difference from the average value is at least 4.5 seconds and less than 5.0 seconds.

To produce the entire histogram, all the A'i, B'i, and C'i data included in the analysis data is classified into the first to twentieth groups, and the number included in each of the 20 groups is found.

The processing involved here will be described. First, in step 4201, counters indicating the number of elements included in the 20 groups are all reset to zero.

Next, the first data included in the analysis data is examined in step 4202.

In step 4203, it is determined whether or not this data is included within a range of −5 to 5 seconds, and only if it is included, the counter of the group in which this data is included is incremented by 1 in step 4204.

After this, in step 4205, the following data is examined. This is repeated for all the analysis data (step 4206), which allows the entire histogram to be found.

This is displayed by white bars in step 4207, with the group number on the horizontal axis and the number of elements on the vertical axis, which allows the entire histogram to be displayed within the distribution graph.

Next, preparations are made to display a histogram of only the designated user.

The designated user can be designated by clicking on a user name in the ranking table 2809 in FIG. 28. However, until something is clicked on, there is still no designated user. Therefore, in this case, the user with the greatest difference from the average value is termed the designated user.

The processing for this involves checking whether or not there is a specified user in step 4208. If there is no designated user yet, in step 4209 the user with the greatest difference is termed the designated user.

To produce a histogram for just the designated user, in step 4210, first the counters indicating the number of elements included in the 20 groups are all reset to zero.

Next, in step 4211, the first data included in the analysis data is examined. This data is included in a range of −5 to 5 seconds (step 4212), and only if the data is for the designated user (step 4213), the counter for the group in which that data is included is incremented by 1 (step 4214). After this, the next data is examined (step 4215).

This is repeated for all the analysis data (step 4216), which allows a histogram for the designated user to be found. This is displayed by black bars, with the group number on the horizontal axis and the number of elements on the vertical axis (step 4217), which makes it possible to add a histogram the designated user in the distribution graph.

If the total number of people is very large, the height of the black bars with respect to the white bars will be low, and it may be difficult to see the trend of the black bars. In such a case, the trend can be made easier to discern by enlarging the scale in the vertical axis direction of the black bars.

In actual processing, the scale may be varied in the display so that the height of the maximum data in the black histogram 2614 is approximately 70% that of the height of the maximum data in the white histogram 2813.

From there on, the screens shown in FIGS. 29 to 37 can be obtained by displaying using the same processing.

As described above, in this embodiment, six types of metric data were used as an example, but other useful metric data and information obtained therefrom will be described through reference to FIG. 43. FIG. 43 is a list of this other useful metric data.

Metric data 4301 shows the blood deposition time, which is the length of time from when the sensor strip is inserted until blood is deposited on the sensor. The metric data 4301 can be obtained by measuring the difference between the start time of step 2216 and the start time of step 2217 in FIG. 22.

Also, the metric data 4301 is the time required for blood collection, and includes the time until a nurse disinfects and washes a patient's finger, inserts the needle to produce blood, and deposits the blood on the sensor. Accordingly, this length of time will be affected by the skill of the nurse, and will also depend on conditions attributable to the patient, such as a patient whose blood comes out slowly.

Therefore, when this metric has been acquired, it is compared for each user by the metric evaluation application 2703. Consequently, a user who takes a particularly long time will be deemed to be lacking in skill, which makes it possible to deal with the situation by offering additional training, etc.

If this metric is compared for each patient at the same time, this length of time can be assumed to be a numerical value that quantifies the health of the patient. Therefore, patients who take a particularly long time can be deemed to patients whose blood comes out slowly. Accordingly, this information can be conveyed to a nurse so that he or she can take appropriate measures, such as warming the patient's finger before pricking it, or pricking it more deeply.

In addition, with some patients who have been judged difficult to collect blood from, there is also the possibility of diminished blood flow due to deterioration of physical condition, so prompting the nurse to take extra care can prevent the patient from falling into a dangerous state.

Also, in practice, simultaneously with this, there may be a lack of patient compliance, with the patient being hesitant to have blood drawn, and this could conceivably make the process take longer.

In this case, the blood deposition time can be interpreted as a numerical value that quantifies the compliance of the patient, and for such patients that take a very long time, this can be conveyed to the nurse so that appropriate measures can be taken, such as having a veteran nurse handle those patients.

As described above, if the process takes a long time, it cannot be determined from numbers alone whether the problem is based on the health of the patient or on compliance. But in any case, if this number is large, it is something the nurses should be apprised of, and their being aware of the situation will improve the quality of care.

Metric data 4302 indicates the length of time until the sensor is removed, and is how much time passed from when blood is applied to the sensor until the sensor is removed. The metric data 4302 can be obtained by measuring the difference between the start time of step 2216 and the start time of step 2220 in FIG. 22.

This time includes the time it takes for the measurement result to come out, and the time it takes until the sensor is actually removed once the user is prompted to remove it. The time it takes for the measurement result to come out is a fairly steady period of time. Therefore, in practice, this time is affected by the time it takes for the sensor to be actually removed once the user is prompted to remove it.

In this period, the patient's blood is in a state of being deposited on the sensor, so the risk of infection through blood is high during this period. Therefore, after the instruction to remove the sensor is issued, it is necessary to discard the sensor quickly into a waste bottle.

Therefore, when the metric data 4302 has been acquired, it is compared for each user, and since a user who takes a particularly long time is deemed to lack enough experience to be aware of infection, appropriate measures such as having the user undergo safety training can be taken.

Metric data 4303 is used as a help usage count, and is the number of times the user presses the help button 1806 in a single measurement period. The metric data 4303 can be acquired by the same procedure as the number of screen touches required for the entire measurement (metric data 2113).

When the metric data 4303 has been acquired, the metric evaluation application 2703 compares it for each user, and since users who take a particularly long time are deemed to be lacking in skill, measures can be taken such as having those users undergo training.

Metric data 4304 is used as the number of times an operation is done or redone, that is, the number of times the "back" button is pressed, and is the number of times the user presses the back button 1808 in a single measurement period. The metric data 4304 can be acquired by the same procedure as the number of screen touches required for the entire measurement (metric data 2113).

When the metric data 4304 has been acquired, the metric evaluation application 2703 compares it for each user, and since users who take a particularly long time are deemed to be lacking in skill, measures can be taken such as having those users undergo training.

Metric data 4305 is used as the number of warnings, and is the number of times a warning is displayed in a single measurement period. The metric data 4305 can be acquired by the same procedure as the number of screen touches required for the entire measurement (metric data 2113).

A warning is generated not only by a problem with the user's operation, but also by hyperglycemia in the patient, etc., and when viewed statistically, the probability of a warning being generated by something other than the user's operation is fairly constant. Therefore, when it is compared for each user, the comparison can have a correlation with the skill of the user.

Therefore, when the metric data 4305 has been acquired, the metric evaluation application 2703 compares it for each user, and since users who take a particularly long time are deemed to be lacking in skill, measures can be taken such as having those users undergo training.

Metric data 4306 is used as a comment input time, and is the time it takes for the user to input a comment, which can be obtained by measuring the difference between the start time of step 2220 and the start time of step 2221 in FIG. 22.

When the metric data 4306 has been acquired, it is compared for each user, and since users who take a particularly long time are deemed to be lacking in skill, measures can be taken such as having those users undergo training.

Metric data 4307 is used as the remaining battery charge, and is the amount of charge remaining in the rechargeable battery in the blood glucose measurement device 1801 at each measurement.

A voltmeter for the rechargeable battery is disposed in the blood glucose measurement device 1801. This makes it possible to find ascertain the remaining charge.

When the metric data 4307 has been acquired, this metric can be used to produce two new, different metrics. One is a metric that indicates whether or not the blood glucose measurement device 1801 has been returned to its docking station, and one is the amount of charge in the rechargeable battery after charging.

To learn the first one, that is, whether or not the user has returned the device to a docking station that functions as a charger, packets with the same measurement ID in analysis data are examined in time series. A packet immediately before the remaining charge increases indicates when the user returns the measurement device to the docking station.

The measurement device does not necessarily have to be returned to the docking station every time, but should be returned to the docking station if it will not be used for some time after continuous measurement of a plurality of patients.

The number of times a device is returned to the docking station is statistically compared by user, and users with a particularly small number of times are deemed to have a tendency not to comply with the rule of returning the device to its docking station, so measures can be taken such as having those users undergo instruction.

To learn what the battery charge is after charging, packets with the same measurement device ID in the analysis data are examined in time series. The power after charging can be obtained from the power level in the packet immediately after the remaining charge is increased.

Because the battery may be used before being fully charged, the power level at this point will not match the capacity of the battery itself. However, by plotting the power level in time series for each measurement device, it can be surmised that a measurement device that tends statistically to have a low remaining charge will have a near the end of its battery life, so measures can be taken such as replacing the battery.

Metric data 4308 is used as the wireless link time, and is the length of time required until the blood glucose measurement device 1801 is linked with the wireless communication means 2001 at the time of measurement. Furthermore, in this case, the ID of the wireless router where the device is linked must be acquired as metric data to identify the location.

When these metrics have been acquired, they are compared for each location. The displayed time is a numerical value that quantifies the location-specific communication state, and since places where linking takes a particularly long time are deemed to indicate a poor wireless state, measures can be taken such as inspecting the wireless router or looking for a source of noise generation.

The wireless link time was used here as a metric, but the number of communications retries or how long it takes for data transfer may be used instead.

Metric data 4309 is used as the cleaning time, and is the elapsed timed from when the blood glucose measurement device is cleaned until measurement.

In a hospital, measurement devices must be cleaned after each measurement in order to prevent hospital acquired infection. In reality, however, this rule is often not followed, and it is common practice to clean a device only when blood is visually apparent.

This metric is used in order to comprehend this situation.

Metric data 4308 can be obtained by storing how long cleaning took the last time and finding the difference from the measurement time.

Also, how long cleaning took last time may itself used as a metric, and in analyzing in the metric evaluation application 2703, the difference from the measurement time may be taken.

When cleaning is performed, it is necessary to record how long it took. For this purpose, a sensor for detecting a component of the cleaning liquid cleaning, such as an alcohol sensor, may be attached to the measurement device, or an acceleration sensor or the like may be provided to the measurement device to detect motion that is unique to cleaning, or the user may simply press an end button or the like when cleaning is finished to record that the cleaning has been completed.

When the metric data 4308 has been acquired, the elapsed time since the cleaning is compared for each user, and any users who take a particularly long time are deemed to be lacking awareness of hospital acquired infection, so measures can be taken such as providing more education.

Metric data 4310 is used as the number of discarded measurements.

The discarding of measurements here means that after measuring a patient's blood glucose level or a QC solution, the user decides to redo the measurement and discards the measurement result. For instance, if a patient's blood comes out slowly and only a small amount of blood is deposited on the sensor strip, the insufficient amount of blood will result in a measurement error, so this measurement result may be discarded and the measurement performed again. In this case, with a conventional method, the measurement result to be discarded is deleted and therefore not sent to the terminal 1903 of the clinical laboratory.

In this embodiment, a flag that distinguishes whether a measurement result is normal or the measurement result was discarded is provided as metric data. Then, the discarded measurement result is sent to the terminal 1903 of the clinical laboratory just as a normal measurement result is.

In the metric evaluation application 2703, because the ratio of the number of times a measurement is discarded to the total number of measurements, and the user-specific number of times a measurement is discarded are displayed in an elapsed time graph, it is possible to pick out users who frequently discard measurement results. Therefore, users for whom this time is particularly long are deemed to have problems in the measurement procedure, so measures can be taken such as providing more training.

Also, if the ratio of the number of times a measurement is discarded to the total number of measurements, and the measurement device-specific number of times a measurement is discarded are displayed in an elapsed time graph, measurement devices with which measurement results are frequently discarded can be picked out.

With a measurement device with which measurement results are frequently discarded, the resistance value changes due to soiling of the sensor strip connector 1802, for example, and it is surmised that there is a possibility that this will adversely affect the measurement results, etc., so measures can be taken such as performing maintenance.

Further, users who frequently discard results can be picked out by displaying in the elapsed time graph the ratio of the number of times a measurement result is discarded to the total number of measurements, and the patient-specific number of times a measurement result is discarded. Patients whose results are frequently discarded are deemed to potentially have problems with measurement due to their health condition, such as when their blood comes out slowly, so measures can be taken such as making this well known among the users so that it can be taken into consideration during measurement.

A means for acquiring new metric data, analyzing it, and displaying it as evaluation data was given above, but rather than new metric data, data that has been acquired in the past may be treated as metric data, and evaluation data can also be produced from this.

Specifically, an example in which the medical data 2101 to 2107 shown in FIG. 21 is used as metric data, in addition to contributing to diagnosis, will be described through reference to FIG. 44.

FIG. 44 is a table showing an example of using medical data as metric data.

In FIG. 44, the QC result (metric data 4401) is the result of QC measurement, serving as a measurement result for quality control.

Conventionally, the results of QC measurement verify that a measurement device is operating normally, and the veracity of the values from patient measurement are guaranteed by this, with users being classified merely by either "normal" or "abnormal" values.

In this embodiment, this is used as a metric because the measurement device has measurement results as numerical values internally.

The original correct value for the QC solution is known from a QC solution database (not shown), using the QC solution ID (2104), for the results of each QC measurement. Therefore, measurement error can be obtained by taking the difference between the measurement result and the correct value.

When this is compared for each user, a comparison having correlation with the skill of the user is possible. Therefore, when this metric is used, the metric evaluation application 2703 can compare this for each user, and any users who tend to have a particularly large accuracy error are deemed to be lacking in skill, so measures can be taken such as providing more training.

Metric data 4402 is a STAT measurement serving as an emergency measurement.

Conventionally, a STAT measurement is used in the diagnosis of patients in substantially the same way as normal patient measurement, but if it is made clear that the measurement is STAT, this alerts the staff that accuracy of the measurement value cannot be guaranteed because the measurement was made in a state of being unable to guarantee the quality of the measurement device. In this embodiment, this is used as a metric.

When the metric data 4402 is used, in order to find the STAT usage frequency for each user, the metric evaluation application 2703 finds the ratio of the number of STAT measurements versus the total number of measurements for each user. These are then compared for each user, and for any users who tend to have a particularly high STAT measurement ratio, it is deemed possible that they are using STAT measurement without performing the established QC measurement, so measures can be taken such as providing more training.

Metric data 4403 is a measurement device ID, which is an individual identification code of the measurement device.

Conventionally, when a problem is seen in a measurement device, the measurement device ID is used for such purposes as alerting the staff to measurement results measured with that measurement device.

In this embodiment, this is used as a metric. When the metric data 4403 is used, in determining how often each measurement device is used, the metric evaluation application 2703 compares the number of measurements within a certain period made with each measurement device, by measurement device, which allows the operation status of the individual measurement devices to be compared.

Consequently, if the operation rate of measurement devices in one particular department is high, while the operation rate of measurement devices in another department is low, it is surmised that the measurement devices may not be disposed optimally, so measures can be taken such as rearranging the measurement devices.

Metric data 4404 is a sensor ID, which is a recognition code for a sensor strip.

Conventionally, sensor IDs have been used for the purpose of alerting the staff to measurement results for sensor strips taken from a certain sensor lot when a problem has been identified for that lot.

In this embodiment, this is used as a metric. When the metric data 4404 is used, for each sensor ID, the metric evaluation application 2703 counts the number of measurements made with the same sensor ID. The current date is then compared to the expiration date of the sensor ID, and for any that are already past the expiration date, the remaining sensors with that sensor ID are assumed to have been discarded.

For example, if a 50-pack sensor ID that has been used for measurement 36 times is past the expiration date, it is determined that the last 14 sensor strips have been disposed of.

Therefore, when the metric data 4404 is used, it is necessary to acquire the number of discarded measurements (metric data 4310) at the same time as metric data. This makes it possible to ascertain the number of sensor strips that were actually used, including those from discarded measurements, so the number of strips discarded can be accurately ascertained by using the expiration date.

With this method, the number of wasted sensor strips is ascertained, and the user who last used the sensor strips with this sensor ID can be compared for each user. A wasted sensor strip is not necessarily the fault of the last user. However, statistically speaking, if wasted strips are concentrated on a particular user, it is surmised that there is the possibility of some kind of problem in the awareness of the user, so measures can be taken such as providing more training of the user.

Metric data 4405 is a comment inputted by a user.

Conventionally, comments are used by the manager of the testing department to confirm the validity of measured values, or are used as a reference by doctors in diagnosis.

In this embodiment, this is used as a metric. When the metric data 4405 is used, the metric evaluation application 2703 compares the comments to a prepared list of comments for each measurement. Then, only custom comments that do not match anything are extracted, and the frequency of each custom comment within a certain period is displayed sequentially as a list, starting with the highest frequency.

The manager of the testing department confirms this, and adds those comments on the list with the highest frequency and importance to a comment list as needed, so that the comments that are being sought in the workplace can be reflected in the comment list.

Up to this point, we have discussed the metric data to be used, the means for producing evaluation data from this, and what is read from that evaluation data. According to the embodiment given so far, choosing topics is easy for a testing department manager who has plenty of experience, but a person with less experience may overlook topics, and may not even be capable of recognizing their importance.

To prevent this, in the following embodiment, an example is given in which what is presented to the staff includes an interpretation of the evaluation data.

Figure 45:
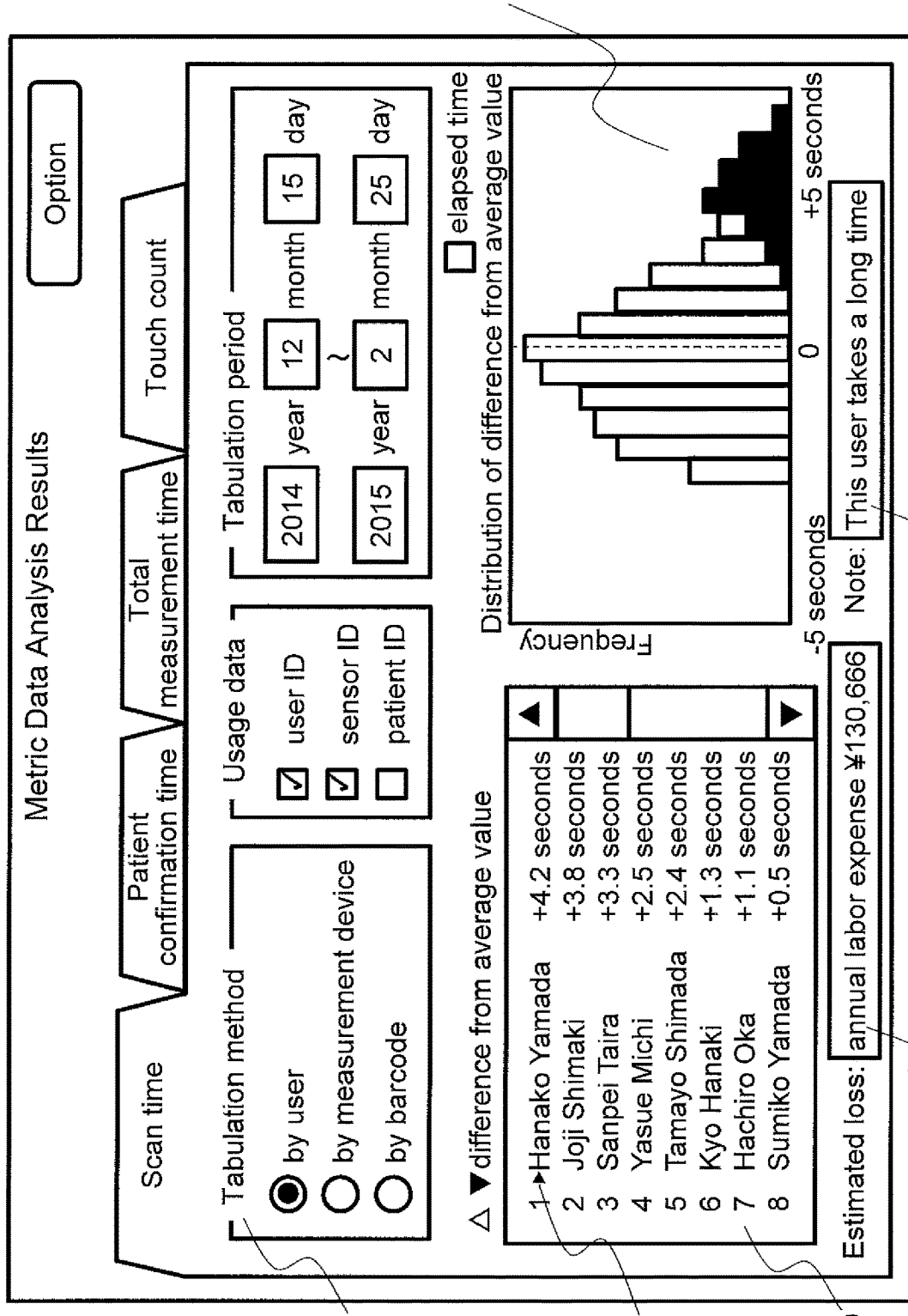
FIG. 45 shows a metric evaluation application screen A' in Embodiment 2 of the present invention.

FIG. 45 shows a screen when a presentation including an interpretation of the evaluation data is given on the display screen in FIG. 28. This screen adds an estimated loss display box 4501 and a note 4502 to the display screen in FIG. 28.

The estimated loss display box 4501 shows how much labor cost has been incurred over the average for the user of interest marked with the selection mark 2811 in the ranking table 2809.

This monetary amount is found by multiplying the labor cost per second and the number of measurements during the past year by the difference from the average for the user of interest.

In the ranking table 2809, if another user has been designated as the user of interest, the monetary loss for the new user of interest immediately appears in the estimated loss display box 4501.

Also, although the annual labor cost is used here as an example, the time period may be any other predetermined period, or may be the total value for the entire tabulation period.

Thus, in addition to the fact that displaying the loss as a monetary amount makes it easy for the severity to be grasped intuitively, it is also easy to compare the costs and loss amounts entailed by training, so another benefit is that it is easier to determine whether or not to give training to the users.

Furthermore, if the user of interest is a user who is more skilled than average and whose difference value is negative, there will be no loss, so the estimated loss display box 4501 may be left blank, or how much of a positive contribution was made may be displayed as a monetary amount.

In FIG. 45, if selection by the tabulation method 2806 is by measurement device, then the ranking table 2809 is also be measurement device, and the measurement device of interest is designated.

In this case, the monetary loss that is generated is displayed in the estimated loss display box 4501 according to the difference value of the measurement device of interest. In this case, how much of a monetary loss was incurred due to soiling or malfunction of a measurement device will be clear, so this becomes an incentive for maintenance.

However, with this embodiment, soiling or malfunction of a measurement device can be detected right away. Therefore, only a short time will pass from when the abnormality occurs, so the actual monetary loss is very small. Thus, the display shows how much of loss will be incurred in one year if no action is taken.

As a calculation method, for example, find the loss time in a short period such as the past 24 hours, and multiply this by 365 to determine the loss time for a year. Then multiply this by the labor cost to find the estimated loss display box 4501. This also applies when selection with the tabulation method 2806 is by barcode.

Then, when the metric data (measurement of the time) 2111 required for patient confirmation is used as metric data, a shorter time is advantageous in terms of labor cost. However, if a mix-up of a patient ends up being caused by this, the resulting loss will not even be comparable to labor cost.

Therefore, with this metric data, if a user of interest with a time below a threshold value is designated, no monetary amount is displayed in the estimated loss box, and instead a warning message is displayed that reads "it will be a serious problem if patient misidentification should occur as a result of this action."

Also, if a user having no time below the threshold value becomes the user of interest, the estimated loss box is left blank.

When the metric data 2112 (time required for the entire measurement) is used, the difference obtained by subtracting the average time for all users from the average time of the user of interest is the loss time. Accordingly, the loss amount can be found by multiplying this difference by the number of measurements within the tabulation period and the labor cost per second.

This value will be the same whenever the labor cost per second is multiplied by the total of the individual differences obtained by subtracting the average time for all users from the time required for the entire measurement, in all measurements within the tabulation period of the user of interest. The loss amount is displayed by displaying the value thus found in the estimated loss box.

Also, if a user whose difference value is negative becomes the user of interest, since there is no loss, the estimated loss box may be left blank, or how much of a positive contribution was made may be displayed as a monetary amount.

Information about the clinical department to which the user belongs, work shifts, and so forth (not shown) are also recorded separately to the terminal 1903 in the clinical laboratory. This information can be used to find the average value of the time required for the entire measurement by clinical department, the average value of the time required for the entire measurement by work shift, and the like. These findings can then be compared to evaluate user efficiency in work shifts and issues for each clinical department.

If the number of screen touches required for the entire measurement is used as the metric data 2113, the difference obtained by subtracting the average number of touches for all users from the average number of touches for the user of interest becomes loss number of touches. Therefore, the monetary loss can be found by multiplying the number of measurements within the tabulation period, the predetermined estimated time required per touch, and the labor cost per second by this difference.

This same value can also be found by multiplying the labor cost per second and the estimated time required per touch by the total of the individual differences obtained by subtracting the average number of touches for all users from the number of screen touches required for the entire measurement, in all measurements in the tabulation period for the user of interest. This monetary amount is displayed in the estimated loss box, which means that the monetary loss is displayed.

Also, if a user whose difference value is negative becomes the user of interest, since there is no loss, the estimated loss box may be left blank, or how much of a positive contribution was made may be displayed as a monetary amount.

If the blood deposition time is used as the metric data 4301, the processing will be substantially the same as for the time 211 required for the entire measurement, and the difference obtained by subtracting the average time for all users from the average time for the user of interest becomes the loss time. Therefore, the loss amount is found by multiplying the number of measurements within the tabulation period and the labor cost per second by this difference, and this result is displayed in the estimated loss box.

If the time until the sensor is removed is used as the metric data 4302, then this is related to rule compliance just as with the metric data (measurement of the time) 2111 required for patient confirmation, so if a user of interest with a time shorter than the threshold value is designated, a monetary amount will not be displayed in the estimated loss box, and instead a warning message of "this action will increase the risk of hospital acquired infection" is displayed.

Also, if a user who has no time shorter than the threshold value is the user of interest, the estimated loss box is left blank.

If the number of "help" requests and the number of "back" operations are used as the metric data 4303 and 4304, the processing is almost the same as with the number of screen touches (metric data 2113) in both cases, and the monetary loss is found by multiplying the number of measurements within the tabulation period, the predetermined estimated required time per touch, and the labor cost per second by the difference obtained by subtracting the average number of times for all users from the average number of times for the user of interest, and this finding is displayed in the estimate loss box.

When the number of warnings is used as the metric data 4305, the response will vary greatly depending on exactly how the warnings are generated, so the time loss cannot be found. Therefore, nothing is displayed in the estimated loss box.

If comment input time is used as the metric data 4306, the processing is substantially the same as with the metric data (measurement of the time) 2112 required for the entire measurement, and the loss time is the difference obtained by subtracting the average time for all users from the average time for the user of interest. Therefore, the monetary loss is found by multiplying the number of measurements within the tabulation period and the labor cost per second by this difference, and the finding is displayed in the estimated loss box.

If the battery remaining charge is used as the metric data 4307, sometimes the number of times the device has been returned to the docking station is evaluated by user from this metric, and sometimes the battery capacity after charging is evaluated by measurement device. In both cases, a loss is an opportunity cost because the measurement device cannot be used if the battery is dead.

Therefore, a warning message such as "there is an increased risk that the measurement device will be unusable due to inadequate charge" is displayed to a user of interest who has returned a device to its docking station only a few times.

Also, the monetary loss is found by the following calculation for a measurement device of interest with which the battery capacity after charging tends to be low.

First, the current charge capacity is divided by the original charge capacity to find the ratio of the currently usable usage period to the original usage period. The proportional period that can no longer be used is obtained by subtracting this ratio from 1. The depreciation equal to the lost time period out of the annual depreciation of the measurement device is obtained by multiplying the annual depreciation of the measurement device by this proportion. This monetary amount is displayed in the estimated loss box as the annual depreciation expense that was wasted.

If the wireless link time is used as the metric data 4308, since this time is the nurse waiting time, the processing is substantially the same as with the metric data (measurement of the time) 2112 required for the entire measurement, and the difference obtained by subtracting the average time for all locations from the average time for the location of interest becomes the loss time. Thus, the loss amount is found by multiplying the number of measurements within the tabulation period and the labor cost per second by this difference, and this finding is displayed in the estimated loss box.

If the cleaning time is used as the metric data 4309, since this is related to rule compliance just as is the metric data (measurement of the time) 2111 required for patient confirmation, if a user of interest with a time longer than the threshold value is designated, no monetary amount is displayed in the estimated loss box, and a warning message of "this action will increase the risk of hospital acquired infection" is displayed.

If the estimated loss when using the number of discarded measurements is used as the metric data 4310, it is necessary to acquire the metric data (measurement of the time) 2112 required for the entire measurement as metric data at the same time.

Consequently, in the discarding of one measurement, the time required for the entire measurement at this point is the loss time, and the monetary loss is the price of one sensor strip and the labor cost during this period. Therefore, for the user of interest, etc., the total monetary loss is found by adding up all of the loss amounts due to discarded measurements within the tabulation period, and this monetary amount is displayed in the estimated loss box.

If the QC result is used as the metric data 4401, since it is unclear how this is related to the monetary loss, nothing is displayed in the estimated loss box.

If STAT measurement is used as the metric data 4402, since this is related to rule compliance just as with the metric data (measurement of the time) 2111 required for patient confirmation, if a user of interest is designated who exhibits a frequency even higher than when a predetermined value is added to the average frequency for all users, then no monetary amount is displayed in the estimated loss box, and a warning message of "this action increases the risk of medical error" is displayed.

If the measurement device ID is used as the metric data 4403, when a measurement device of interest exhibiting a usage frequency higher than a predetermined threshold is designated, no monetary amount is displayed in the estimated loss box, and instead a warning message of "not enough measurement devices, which could lead to unnecessary labor cost" is displayed.

Also, when a measurement device of interest exhibiting a usage frequency lower than the remainder of subtracting a predetermined value from the average usage frequency of all measurement devices is designated, the quotient of dividing the usage frequency of the measurement device of interest by the average usage frequency is subtracted from 1, after which that remainder is multiplied by the annual depreciation of the measurement device, and the value thus obtained is displayed in the estimated loss box as wasted annual depreciation.

If the sensor ID is designated as the metric data 4404, since the user of interest (here, the user who last used a sensor strip with a certain sensor ID) does not correlate well to the number of wasted sensor strips, regardless of which user of interest is designated, the value obtained by multiplying the unit price by the number of all sensor strips wasted within the tabulation period is displayed in the estimated loss box as the wasted sensor cost.

When the sensor ID is designated as the metric data 4404, in the inputting of comments, a custom comment will take far longer than it takes to select from a comment list. Thus, the monetary loss is found by multiplying a reference time for a predetermined custom comment input by the number of times the user of interest inputs a custom comment within the tabulation period, and then multiplying this product by the labor cost per second, and this finding is displayed in the estimated loss box.

What is given in the estimated loss box was described above.

Meanwhile, in FIG. 45, the note 4502 indicates characteristics of the evaluation data for the user of interest that can be read from the distribution graph 2812. The note 4502 in FIG. 45 provides a tip about problem extraction to the manager of the testing department who is looking at the screen.

How to find the display content (note content) of the note 4502 will be described below.

Figure 46:
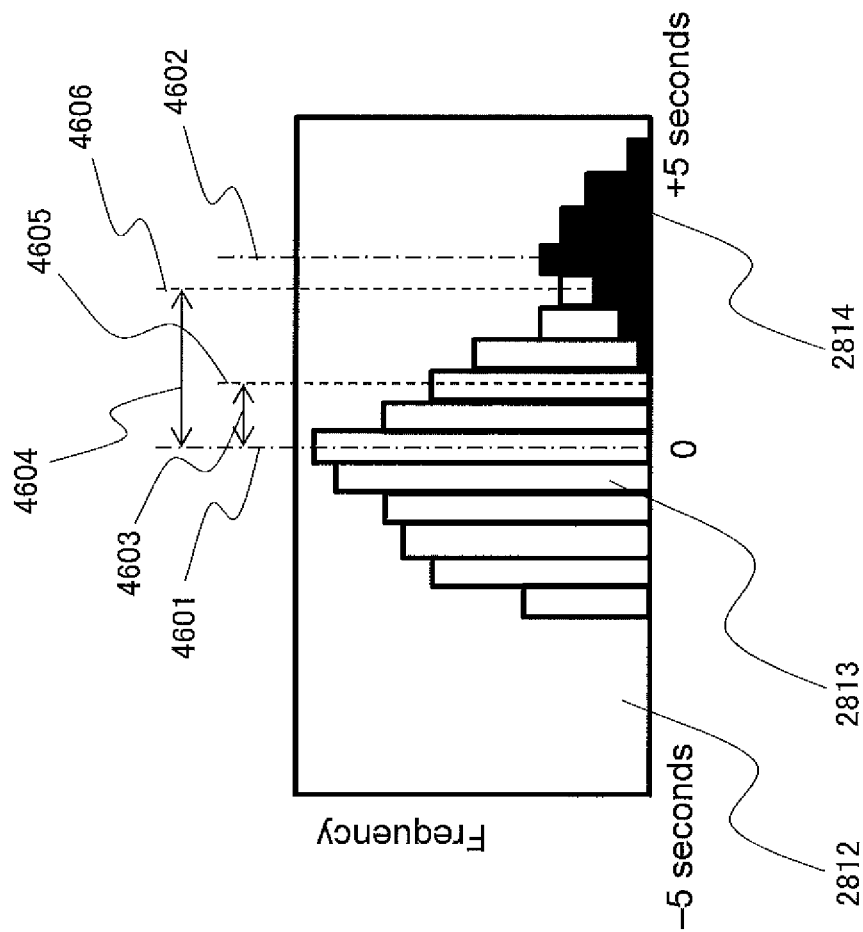
FIG. 46 shows an example A of a distribution graph in Embodiment 2 of the present invention A.

FIG. 46 shows just the distribution graph 2812 taken from FIG. 45, and illustrates the method for finding the most basic note contents therein.

In FIG. 46, the distribution graph 2812 shows a histogram 2813 of the entire distribution represented by white, and a histogram 2814 of the distribution of the data of interest represented by black.

FIG. 46 shows the peak position 4601 of the histogram 2813 of the overall distribution, and the peak position 4602 of the histogram 2814 of the distribution of the data of interest.

Two thresholds are prepared in advance for this. The first threshold value 4603 indicates that there is a certain amount of discrepancy with respect to the total, so caution should be urged. The second threshold value indicates that there is considerable discrepancy with respect to the total, so measures need to be taken.

Therefore, as shown in FIG. 46, if the peak position 4602 of the histogram 2814, which shows the distribution of the data of interest, is further to the right than the second boundary 4606, which is separated by the second threshold value 4604 from the peak position 4601 of the histogram 2813, which shows the overall distribution, then the note 4502 will display a note content that includes a countermeasure, namely, "this user takes a considerable amount of time to scan, so training is necessary."

Also, if the peak position of the histogram 2814, which shows the distribution of the data of interest, is at a first boundary 4605 and a second boundary 4606 that are separated by the first threshold value 4603 from the peak position 4601 of the histogram 2813, which shows the overall distribution, then the note 4502 will display note content urging caution, namely, "there is an alert that this user takes a relatively long time to scan."

Here, an example was given in which the determination is based on the distance between the peak positions of two histograms, but the difference between the average value for the data of interest and the overall average value may be used instead.

Figure 47:
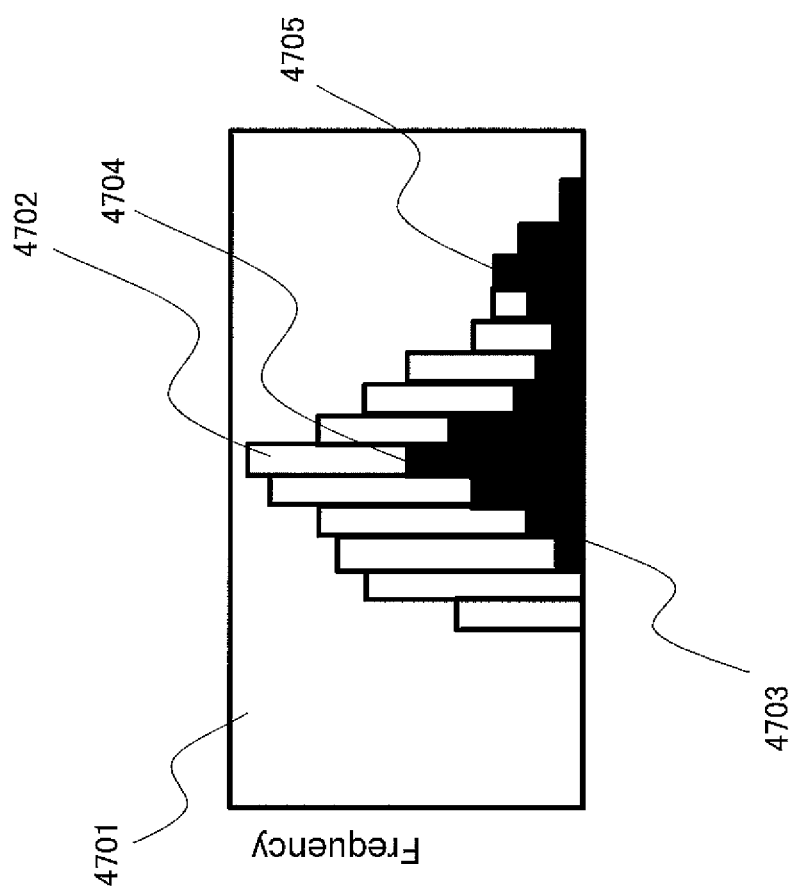
FIG. 47 shows an example B of a distribution graph in Embodiment 2 of the present invention A.

Also, the distribution graph is sometimes as shown in FIG. 47. In FIG. 47, 4701 is a distribution graph, 4702 is a histogram showing the overall distribution represented by white, and 4703 is a histogram showing the distribution of the data of interest represented by black.

In this drawing, there are two peaks in the histogram 4703 that shows the distribution of the data of interest: a first peak 4704 and a second peak 4705.

In such a case, for example, the barcode scanning time of the measurement device of interest is originally distributed around the first peak 4704, but the function of the barcode scanning is diminished at a certain point by soiling, and thereafter the distribution is around the second peak 4705, and such situations may change the characteristics of the distribution over time.

Accordingly, if a plurality of peaks are detected in the histogram of the data of interest, the note 4502 will display a note content of "check the elapsed timed," prompting the display of the elapsed time graph 3101.

Figure 48:
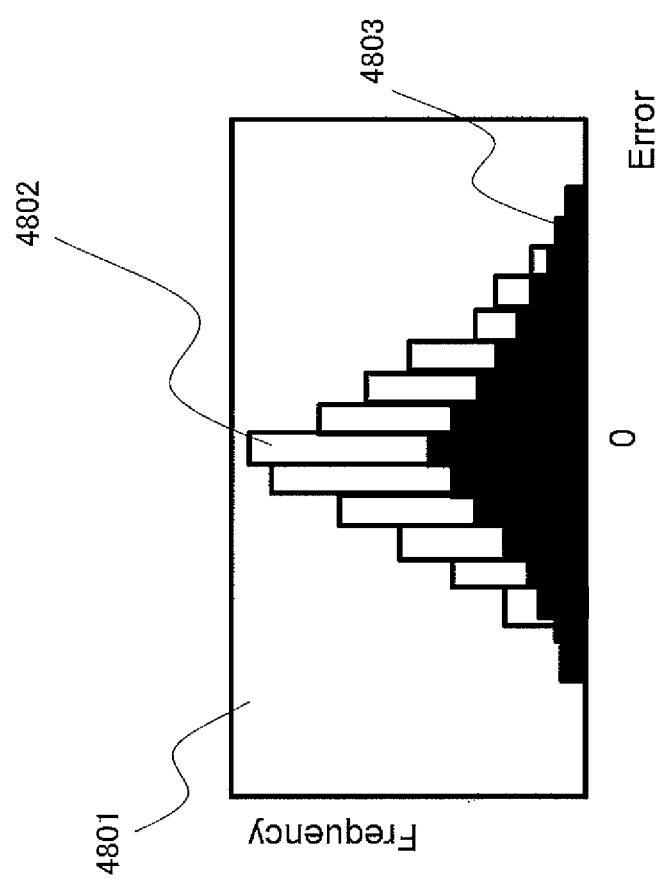
FIG. 48 shows an example C of a distribution graph in Embodiment 2 of the present invention A.

If a QC result is used as metric data, the distribution graph will sometimes be as shown in FIG. 48.

In FIG. 48, 4801 is a distribution graph, 4802 is a histogram of the overall distribution represented by white, and 4803 is a histogram of the distribution of the data of interest represented by black. In FIG. 48, the histogram 4803 of the distribution of the data of interest has a lower peak than the histogram 4802 of the overall distribution, and is more in the shape of a foothill.

A case such as this represents a state in which the QC measurements made by the user of interest contain many errors. Therefore, variance in the histogram of the user of interest, that is, the standard deviation, is found, and if this is greater by at least a predetermined value than the standard deviation in the overall distribution, a note of "this user has multiple QC errors" is displayed.

Also, if the variance is even greater, a countermeasure may be presented in the form of "since this user has very many QC errors, training is necessary."

If the results of QC measurements are distributed such that they skew to a higher concentration, it is possible that the concentration of the QC solution is actually rising because it is drying out due to forgetting to close the cap on the QC solution, so a note of "review QC solution management procedure" may be displayed.

Figure 49:
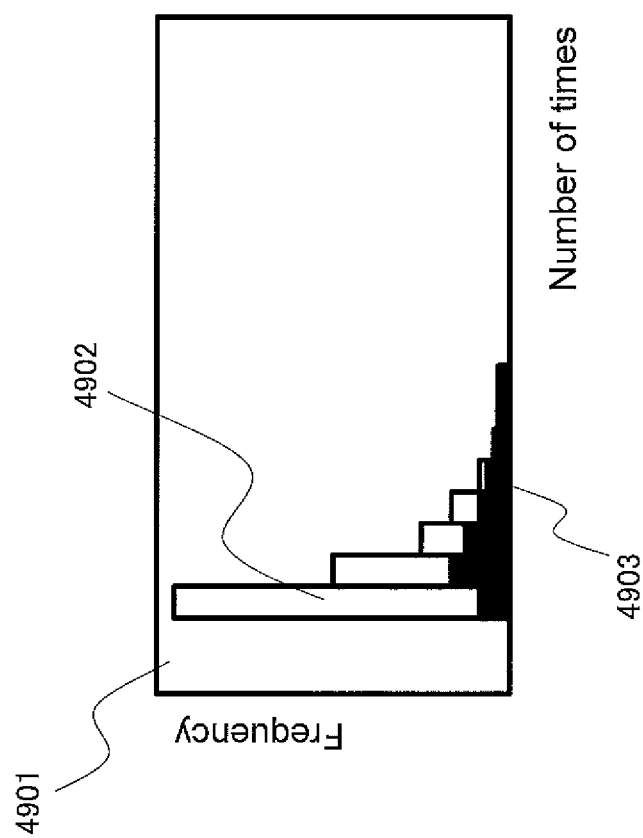
FIG. 49 shows an example D of a distribution graph in Embodiment 2 of the present invention A.

If the number of screen touches required for the entire measurement, the number of "help" requests, the number of "back" operations, and the number of warnings are used as metric data, the distribution graph may be as shown in FIG. 49.

In FIG. 49, 4901 is a distribution graph, 4902 is a histogram of the overall distribution represented by white, and 4903 is a histogram of the distribution of the data of interest represented by black. In FIG. 49, in the histogram of the overall distribution, the peak is at the smallest number of times on the left, and the frequency drops off sharply as the number of times increases.

On the other hand, if the user of interest is not very skilled, the peak may not be located all the way to the left, or the frequency may change gently as the number of times increases. Therefore, when the peak in the histogram 4903 of the user of interest is not all the way to the left, or when there is little change in frequency relative to the number of times, the note 4502 will display "this user may need more skill."

Figure 50:
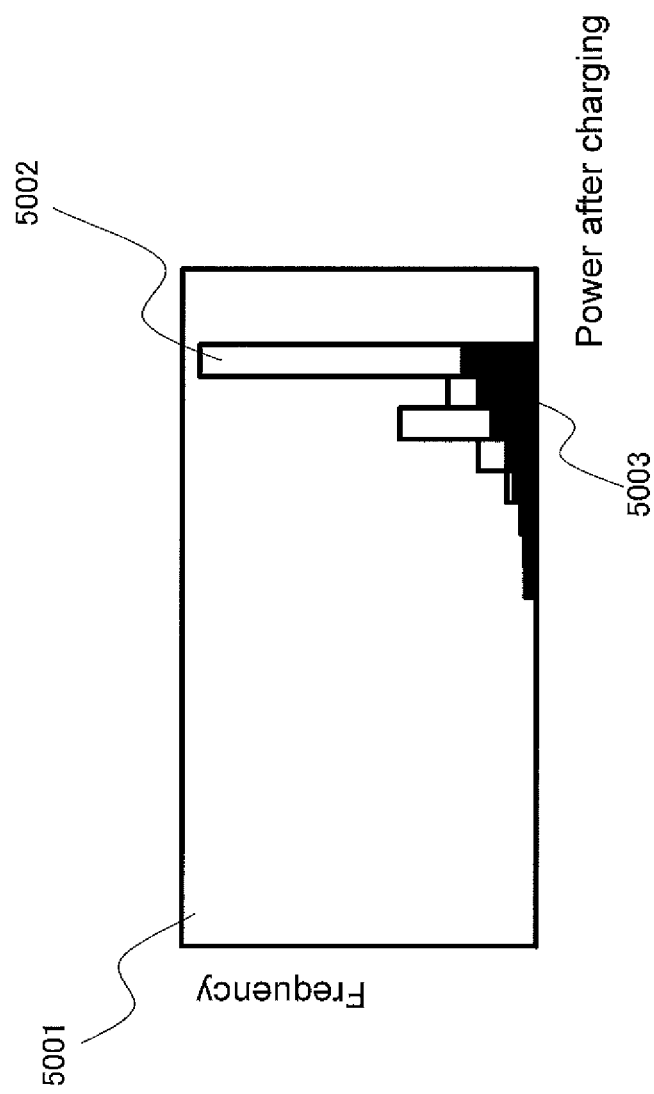
FIG. 50 shows an example E of a distribution graph in Embodiment 2 of the present invention A.

If the remaining battery charge is used as the metric data 4307, and the amount of power after charging is analyzed, the distribution graph may be as shown in FIG. 50.

In FIG. 50, 5001 is a distribution graph, 5002 is a histogram of the overall distribution represented by white, and 5003 is a histogram of the distribution of the data of interest represented by black. In FIG. 50, in the histogram of the overall distribution, the peak is at the maximum charge on the right, and other than this, the results are relatively random depending on the charge.

On the other hand, if the battery of the measurement device of interest deteriorates and its charge capacity gradually decreases, the distribution will fall off to the left relatively gently. Therefore, if there is a tendency such as this in the histogram 5003 of the measurement device of interest, the note 4502 will display "the charge may have a tendency to decrease, so replacing the battery should be considered."

The method for determining the note that is left for a particular situation when displaying a distribution graph was described above, but next we will describe a method for determining the note content when displaying an elapsed time graph.

In this embodiment, if the elapsed time display check box 2815 has been checked, an elapsed time graph 2901 is displayed as shown in FIG. 29. The method for determining what will be written as the note 4502 when displaying the elapsed time graph 2901 will now be described through reference to FIG. 51 onward.

Figure 51:
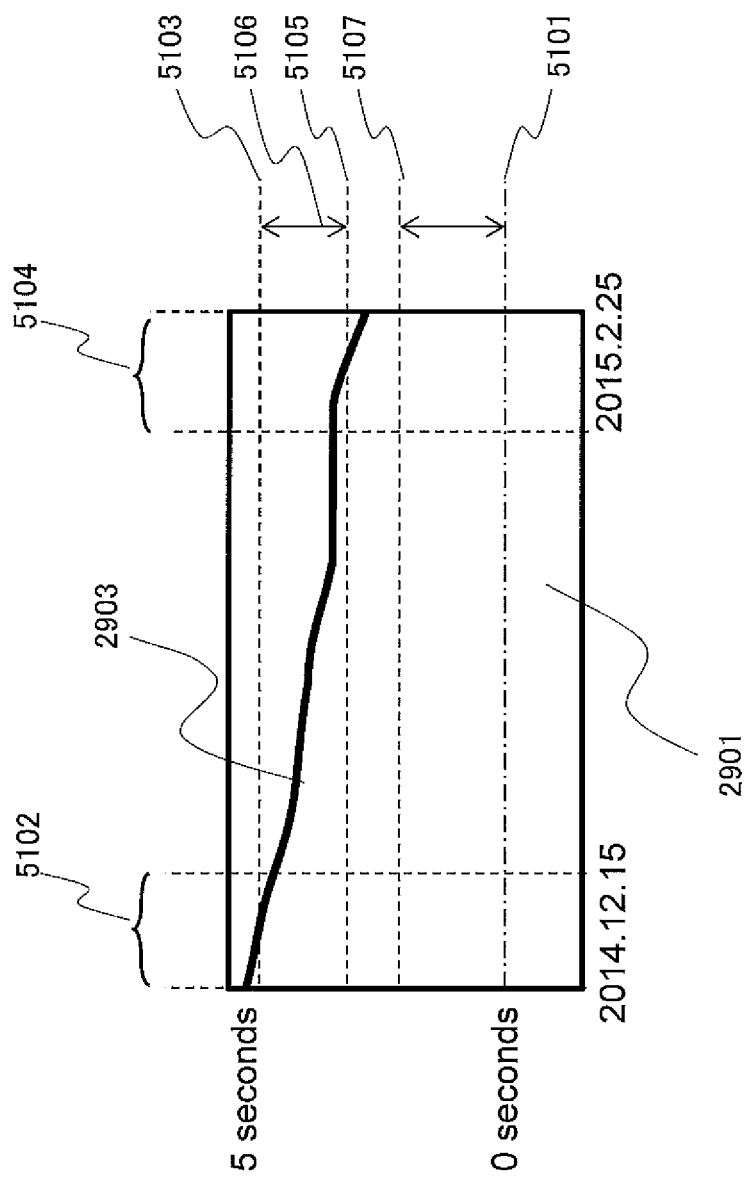
FIG. 51 shows an example of an elapsed time graph A in Embodiment 2 of the present invention.

FIG. 51 is an example of the elapsed time graph 2901, and shows the learning curve 2903 of the user of interest. Here, for clarity of illustration, the learning curves of other users are not shown.

The horizontal axis is the tabulation period, and in this embodiment, the date of the oldest data (here, Dec. 15, 2014) is displayed on the left end, while the current date (here, Feb. 25, 2015) is on the right end. The one-dot chain line indicates the time of the average value 5101 for all data, but since the time here is displayed by the difference from the overall average, this indicates that the difference is zero seconds.

FIG. 51 shows a situation in which the user of interest takes about 5 seconds longer than average early in the tabulation period, but gradually becomes faster, and currently only takes about 3 seconds longer than average.

In this situation, first, the average value 5103 of the learning curve 2903 in the first period 5102 of the tabulation period (such as the first one-tenth of the period) is found. The average value 5103 represents the skill level of the user of interest at the start of tabulation. Similarly, the average value 5105 of the learning curve 2903 is found in the last period of the tabulation period 5104 (such as the last one-tenth of the period). The average value 5105 represents the skill level of the current user of interest.

At this point, the difference 5106 between the average value 5103 and the average value 5105 represents the amount of improvement in the user of interest. Therefore, if this value is over a predetermined threshold, the note 4502 displays "high lever of proficiency indicated."

Also, another threshold value 5107 is prepared. The threshold value 5107 is the sum of adding a predetermined value to the average value 5101, and is a threshold for determining whether or not training is required.

The threshold value 5107 is compared with the average value 5105 representing the skill level of the current user of interest, and if the average value 5105 is larger, this indicates that training is required. Therefore, in this case, the note 4502 displays "high proficiency is exhibited, but training is still required."

The tabulation period displayed in the elapsed time graph 2901 can be selected, and a specific short period from the past can also be displayed. However, regardless of the displayed tabulation period in the elapsed time graph 2901, this step shall be assumed to be performed using all the data up to the present.

Figure 52:
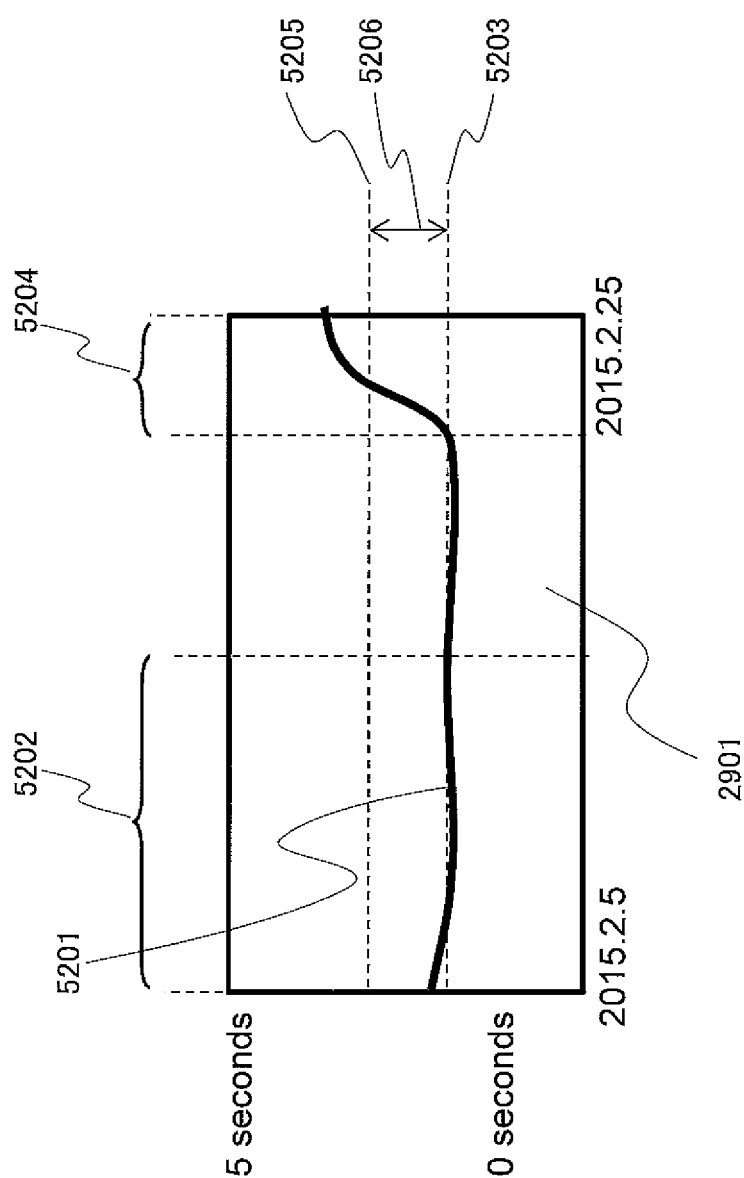
FIG. 52 shows an example of an elapsed time graph B in Embodiment 2 of the present invention.

Next, a method for choosing a problem in a shorter period will be described through reference to FIG. 52. FIG. 52 is another example of the elapsed time graph 2901, in which the shape of the learning curve 5201 of the user of interest differs from that in FIG. 51. Also, since changes are detected in a shorter period, the tabulation period is also displayed over a shorter term of 20 days, with the left end of the horizontal axis being 20 days ago, and the right end the current time.

In FIG. 52, the learning curve 5201 shows a case in which the user of interest has encountered some kind of problem recently and is not working as efficiently. In this case it is more likely that a medical error will be committed, so this situation must be detected and dealt with early on.

Therefore, first the average value 5203 of the learning curve 5201 is found in the first period 5202 (such as the first half of the period). The average value 5203 represents the original skill level of the user of interest.

Similarly, the average value 5205 of the learning curve 5201 in the last period 5204 of the tabulation period (such as the last one-tenth of the period) is found. The average value 5205 represents the current state of the skill of the user of interest.

At this point, if the difference 5206 between the average value 5205 and the average value 5203 is over a predetermined threshold, the note 4502 displays "the efficiency of this user has fallen off recently, and therefore needs to be checked."

The tabulation period displayed in the elapsed time graph 2901 can be selected, but regardless of the displayed tabulation period in the elapsed time graph 2901, this step shall be assumed to be performed using the data for a predetermined short period (in this example, 20 days) up to the present.

In actual processing, first the processing of high importance described through reference to FIG. 52 is performed, and if there is no problem, the processing described through reference to FIG. 51 is performed. Consequently, a note of higher importance is displayed at a higher level of priority.

The step of determining what is written in the note 4502 in comparing evaluation data by user was discussed above, but a means for determining what to write in the note 4502 in comparing evaluation data by other criteria, such as by measurement device, by barcode, or by patient, will now be described through reference to FIG. 53.

Figure 53:
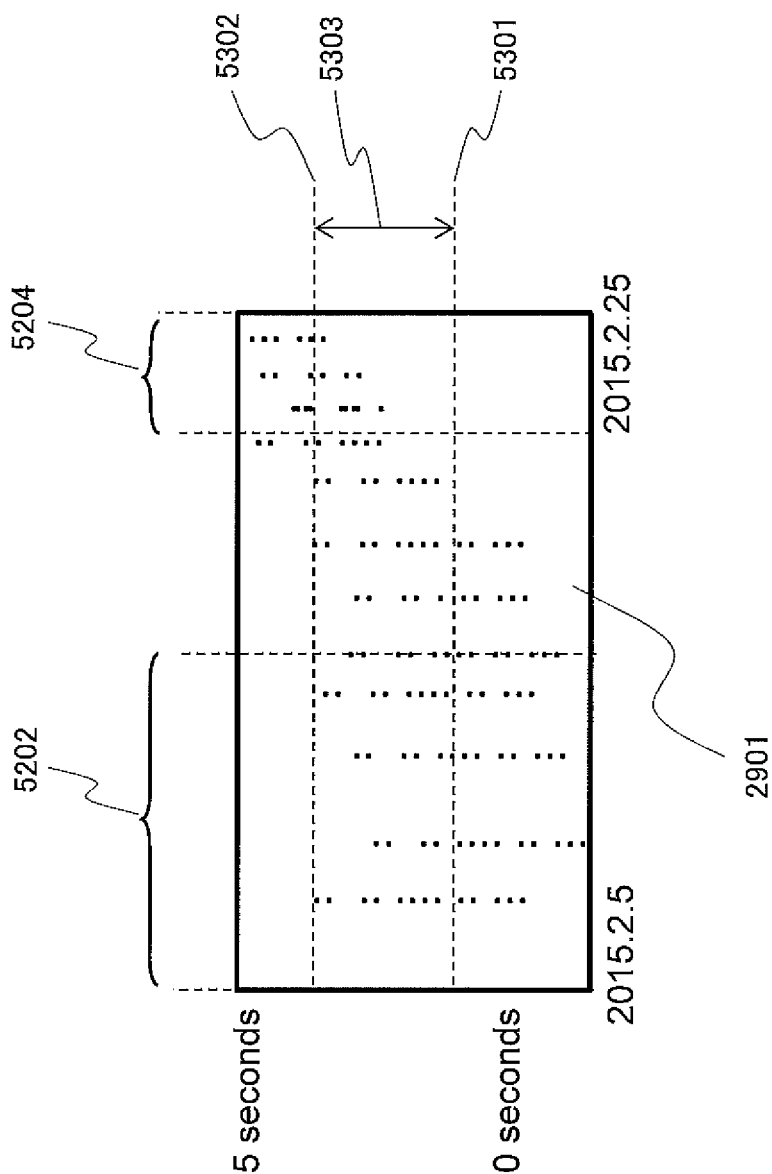
FIG. 53 shows an example of an elapsed time graph C in Embodiment 2 of the present invention.

The method shown in FIG. 53 is the same as in FIG. 52. FIG. 53 is yet another example of the elapsed time graph 2901, in which the horizontal axis is the measurement date and time, with the left end being 20 days ago and the right end the current time, and the vertical axis is time. The time it took to scan with the measurement device of interest is plotted.

FIG. 53 shows a state in which scanning performance is diminished by soiling of the scanner of the measurement device of interest three days ago. Accordingly, plot points tend to concentrate upward from three days ago.

To detect this situation, first the average value 5301 of plot points in the first period 5202 (such as the first half of the period) is found. The average value 5301 represents the original scan time of the measurement device of interest.

Similarly, the average value 5302 of plot points in the last period 5204 of the tabulation period (such as the last one-tenth of the period) is found. The average value 5302 represents the scan time of the current measurement device of interest.

At this point, if the difference 5303 between the average value 5302 and the average value 5301 is over a predetermined threshold, the note 4502 displays "the performance of this measurement device has decreased; maintenance necessary."

In the same method, in the case of evaluation by barcode, for example, the note 4502 displays "this barcode may be soiled; needs to be replaced," etc.

Also, the tabulation period displayed in the elapsed time graph 2901 can be selected, but regardless of the displayed tabulation period in the elapsed time graph 2901, this processing is performed using the data from a predetermined short period up to the current time (in this embodiment, 20 days).

Figure 54:
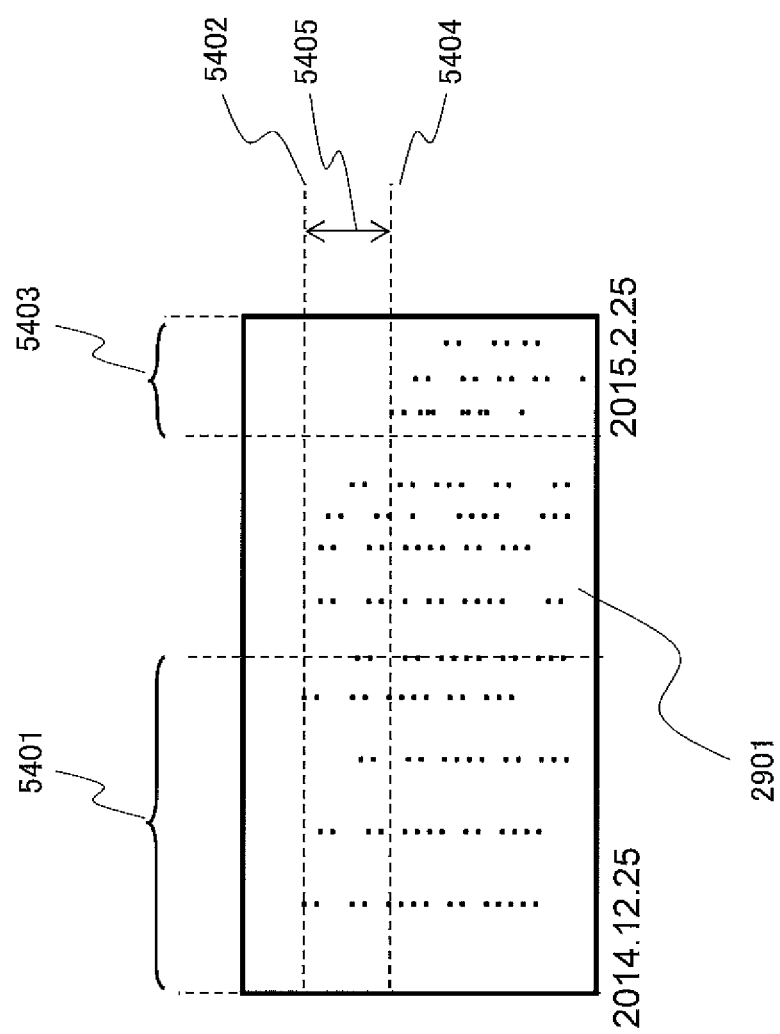
FIG. 54 shows an example of an elapsed time graph D in Embodiment 2 of the present invention.

Next, an example of evaluating the power capacity of the battery in the measurement device as evaluation data will be described through reference to FIG. 54. FIG. 54 is an elapsed time graph for evaluating the power capacity of a battery, in which the horizontal axis is the measurement date and time, with the left end being 2 months ago and the right end the current time, and the vertical axis is the amount of power.

To produce this elapsed time graph, the remaining battery charge is acquired as the metric data 4307, and just the packet of the measurement device of interest is examined in time series. Then, the amount of power in the packet immediately after the remaining charge was increased is plotted.

The amount of power plotted here may also be used before a full charge is reached, so it does not coincide with the power capacity of the battery itself. However, the highest point in the plot can be assumed to approximate the power capacity of the battery itself.

FIG. 54 shows an elapsed time graph in which the power capacity of the battery is deteriorating.

To detect this situation, first, the maximum value 5402 of the plot points in the first period 5401 (such as the first half of the period) is found. The maximum value 5402 represents the original power capacity of the battery of measurement device of interest.

Similarly, the maximum value 5404 of the plot points in the last period of the tabulation period 5403 (such as the last three days) is found. The maximum value 5404 represents the power capacity of the battery measurement device of interest at the current time.

At this point, if the difference 5405 between the maximum value 5402 and the maximum value 5404 is over a predetermined threshold, the note 4502 displays "the battery capacity of this measurement device has decreased; needs to be replaced."

Regardless of the tabulation period displayed in the elapsed time graph 2901, this processing is performed using the data from a predetermined short period up to the current time (in this example, two months).

The method for displaying in the elapsed time graph 2901 was described above.

Next, a method for eliminating disturbance and more easily detecting problems in the display of evaluation data will be described.

In FIG. 47, in the event that two peaks appeared, the barcode scanning time of the measurement device of interest was distributed around the original first peak 4704, for example, but it was assumed that the characteristics of the distribution might change over time, such as when at some point soiling diminishes the barcode scanning function, and after that the distribution is around the second peak 4705.

In practice, however, there is another possibility. Here, the first peak is the same, but the second peak 4705 always has a later operation by a specific user, so there is a possibility that the results when this user operates the device will be distributed around the second peak 4705.

In this case, first, a particular user exhibiting a distribution different from what is expected can be selected by the method shown in FIG. 46 from a distribution graph that gives a comparison by user. Therefore, the second peak can be erased by masking all the measurement results for that particular user, and again displaying the distribution graph by measurement device of interest. It then becomes clear that there is no problem with the measurement device of interest itself, so misdetection can be avoided if there is a possibility that the measurement device of interest is soiled.

Thus, in one piece of metric data, when evaluation data is compared by a plurality of tabulation method, the function of being able to mask certain data is added. This method will be described below.

The metric data used to compare evaluation data by a plurality of tabulation methods can be the time required for the scan (metric data 2108 to 2110), the metric data (measurement of the time) 2112 required for the entire measurement, the blood deposition time (metric data 4301), the number of measurements discarded (metric data 4310), or the like.

Therefore, the metric evaluation application 2703 is assumed to have a means for masking certain data before this evaluation data is displayed, and a mask removal means.

The masking method when using the metric data (measurement of the time) 2112 required for the entire measurement as the metric data will now be described through reference to FIG. 55.

Figure 55:
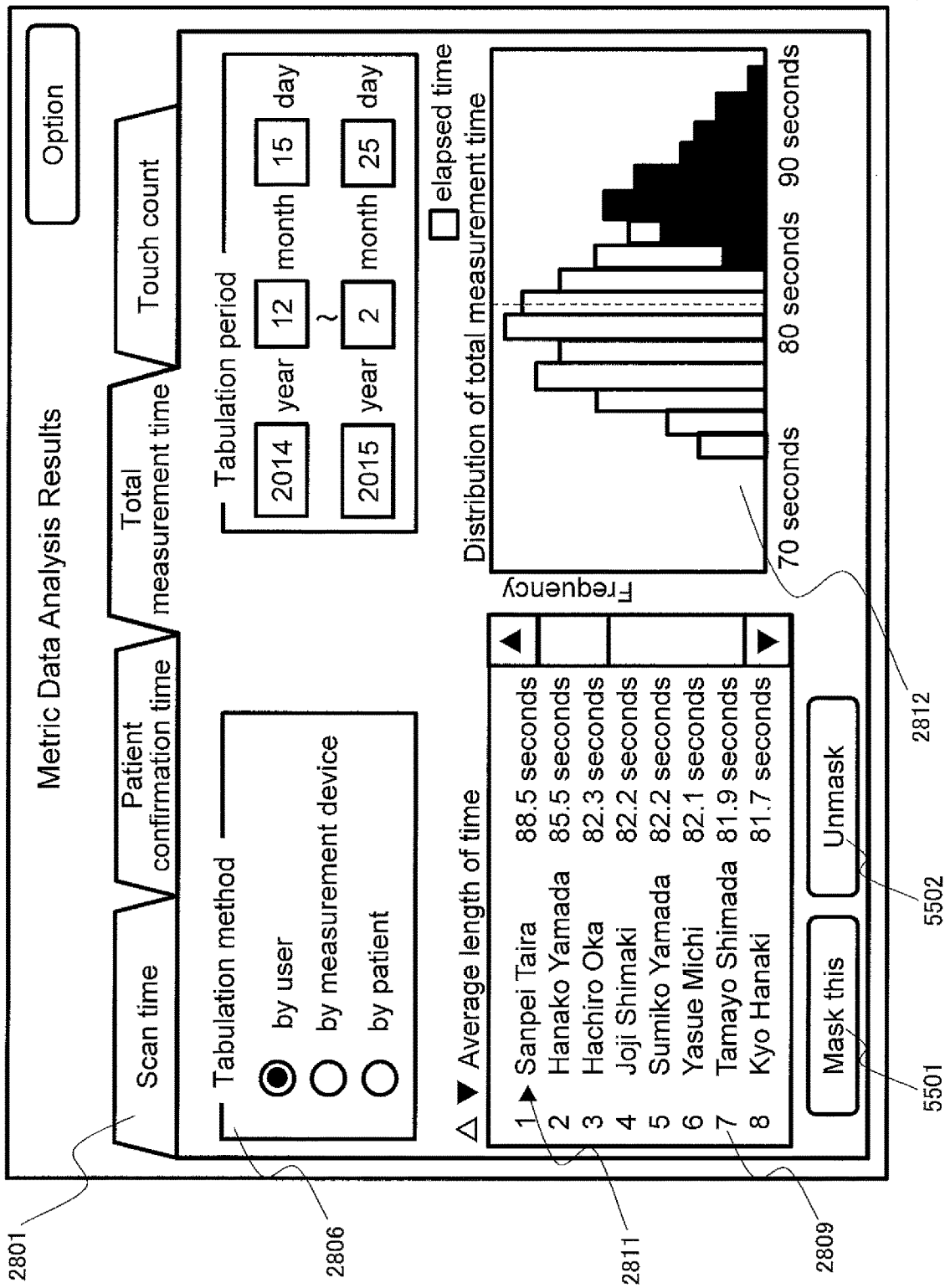
FIG. 55 shows a metric evaluation application screen E in Embodiment 2 of the present invention.

FIG. 55 shows the display screen when a masking means is added to FIG. 36. FIG. 55 differs from FIG. 36 only in that a mask button 5501 and a mask cancel button 5502 are added.

FIG. 55 shows the procedure when the characteristics of each measurement device are evaluated by excluding other influences on the measurement device.

First, the laboratory manager designates user of interest from the ranking table 2809 and confirms the distribution graph 2812 at that time.

If the distribution graph for the current user of interest exhibits a different distribution from what is expected, when the mask button 5501 is clicked on, the metric evaluation application 2703 masks the overall measurement results for the user of interest currently designated, and excludes those from subsequent evaluation data analysis.

The laboratory manager checks whether or not the distribution graph exhibits a distribution different from what is expected, just as for other users, and patients that are different are sequentially masked using the mask button 5501.

Typically, the users are checked sequentially starting from the top, and if the distribution graph for the user of interest is a normal distribution, all subsequent users will have the same distribution, so there is no need to examine any further.

When the check by user is finished, the laboratory manager now selects by patient with the tabulation method 2806.

In this case, since the ranking table 2809 is displayed by patient, an examination is similarly made by patient. Then, if the distribution graph for the current patient of interest exhibits a distribution that is different from what is expected, when the mask button 5501 is clicked on, the metric evaluation application 2703 makes all the measurement results for the patient of interest who is currently designated, and excludes them from subsequent evaluation data analysis.

When the check by patient is finished, the laboratory manager selects by measurement device with the tabulation method 2806.

The evaluation data by measurement device displayed here shows the results of excluding user and patient data exhibiting an abnormal distribution. Therefore, it is possible to display the pure measurement device characteristics that exclude these effects.

When the mask cancel button 5502 is clicked on, all the data that had been masked are restored, and evaluation data is displayed in all of the data just as before.

Next, the processing of the metric evaluation application 2703 when the mask button 5501 is clicked on will be described.

If the tabulation method 2806 is by patient, when the mask button 5501 is clicked on, the metric evaluation application 2703 first examines the user ID of the user of interest.

Next, the user IDs are sequentially examined for all packets in the target data file, and masking is performed on those that match the user ID of the user of interest.

The masking processing can be accomplished by various methods. For example, if the date and time of the packet are changed to a future date and time, this packet will be excluded from all processing even though the other processing is not changed.

After all the packets have been checked, the ranking table 2809 and the distribution graph 2812 are redrawn with the processed target data files. This deletes the original user of interest from the ranking table 2809, and the ranking table 2809 is displayed with one less person therein.

Similarly, if the mask button 5501 is clicked on when the tabulation method 2806 is by measurement device, the measurement device IDs are sequentially checked for all the packets in the target data file, and masking is performed on those that match the measurement device ID of the measurement device of interest.

After all the packets have been checked, the ranking table 2809 and the distribution graph 2812 are redrawn with the processed target data files.

Furthermore, if the mask button 5501 is clicked on when the tabulation method 2806 is by patient, the patient IDs are sequentially examined for all packets in the target data file, and masking is performed for those that match the patient ID of the patient of interest. After all the packets have been checked, the ranking table 2809 and the distribution graph 2812 are redrawn with the processed target data files.

Also, when the mask cancel button 5502 is clicked on, steps 3801 to 3805 in FIG. 38 are performed again, and a target data file is produced from the laboratory terminal output file, whereupon the target data file returns to the state it was in before the masking.

Here, a method in which the date and time of the target data file packets are changed is given as a method for masking. However, a method may be used in which a flag indicating whether masking is enabled or disabled may be provided for each packet, and this portion operated according to the state of masking.

In this case, only the flag is returned during unmasking, and it is not necessary to produce another target data file from the laboratory terminal output file.

Also, if the tab 2801 is clicked on, for example, in order to perform evaluation data analysis using other metric data after masking has been performed, the same processing as when the unmask button is clicked on will be automatically performed to prevent the current masking state from affecting different metric data.

In this embodiment, 19 types of metric data analysis have been mentioned so far, but the type of information that is required will vary from one hospital to the next.

More specifically, since there is also metric data for managing users, in a hospital where the nurses have a lot of power, for example, it is undesirable to acquire and analyze these types of metric data.

Therefore, in this embodiment, a means may be provided that allows only what is required from among the above 19 types of metric data, for each hospital.

More specifically, the selection means may be one that allows selection to be executed from the metric evaluation application 2703 at the terminal 1903 of the clinical laboratory, and this improves convenience of operation.

Figure 56:
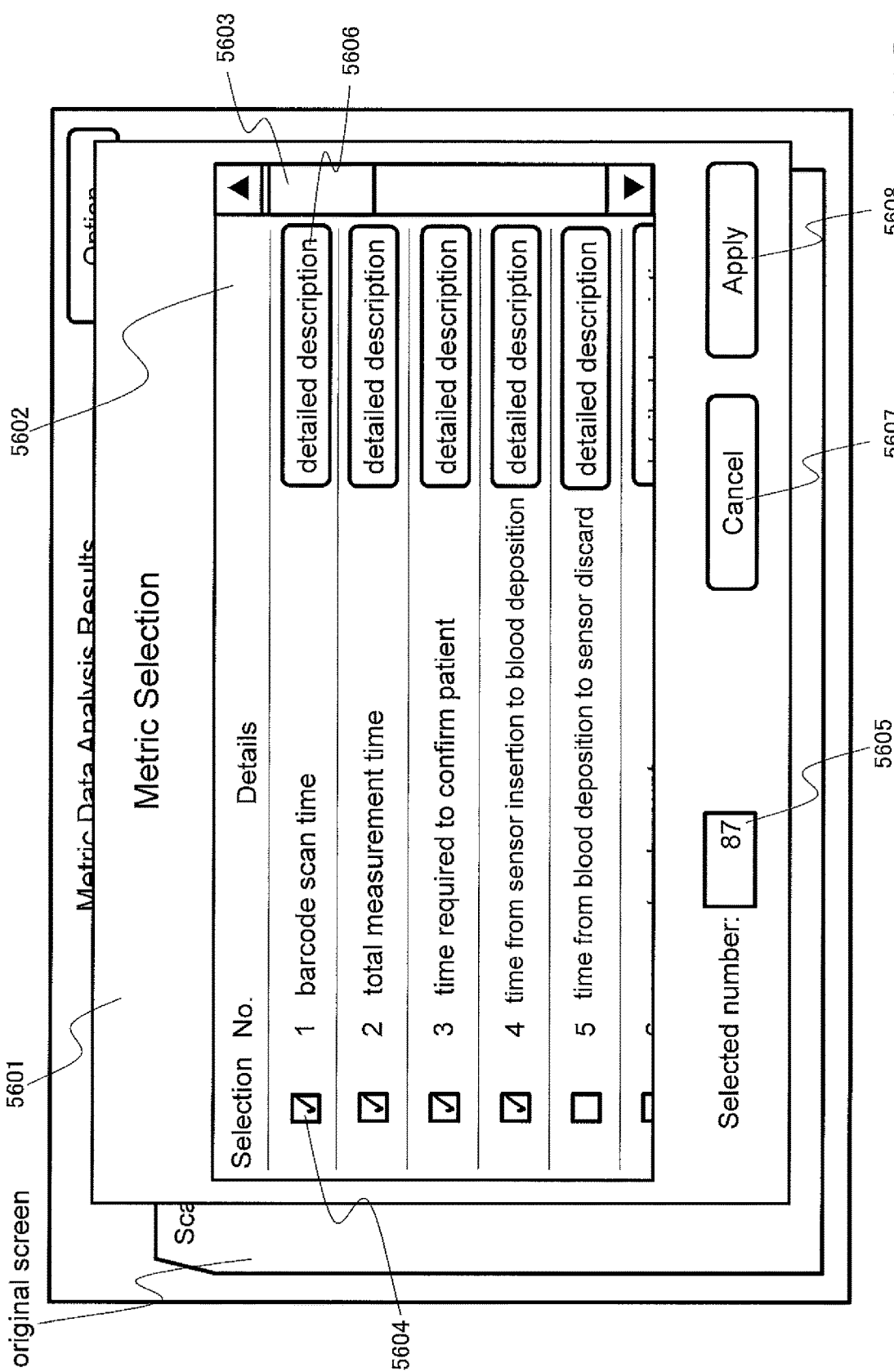
FIG. 56 shows a metric selection screen in Embodiment 2 of the present invention.

For instance, FIG. 56 shows the screen when the option button 2805 in FIG. 28 is clicked on. In FIG. 56, the metric selection screen 5601 is displayed superposed over the screen shown in FIG. 28.

In FIG. 56, all the usable types of metric data are listed in the metric list 5602. The scroll bar 5603 is then used to scroll up or down to view the desired part of the list.

A selection component 5604 is provided in front of each metric. Then, when the selection component 5604 is clicked on, a check mark appears or disappears. When the check mark is visible, it means that that metric has been selected.

When this screen has been opened, it is displayed in a state in which a check mark is placed in the selection component 5604 of the metric selected at that time.

The selected number 5605 portion indicates the number of metrics that have been selected at present. For instance, if the maximum number of metrics that can be acquired at the same is 10 due to constraints on the memory capacity, etc., when the selected number exceeds 10, there will be no selected state even if you click on a selection component that does not have a check mark.

When the detailed description 5606 button is clicked on for each metric list, a detailed description of that metric will be displayed in a pop-up window. The detailed description includes the meaning of that metric, the analysis method in which that metric is used, how to read the analysis results, and how to deal with the analysis results.

When the cancel button 5607 is selected, whatever was done after opening this metric selection screen will be discarded, and the metric that was selected immediately before opening this metric selection screen will be used.

On the other hand, when the apply button 5608 is clicked on, whatever was done after opening this metric selection screen will be reflected, and thereafter a new type of metric is acquired.

If a metric selected by the selecting means is changed, the terminal 1903 in the clinical laboratory notifies all the registered blood glucose measurement devices 1801 of the change via the wireless communication means 2001 and the wired communication means 2003.

Upon receiving a change instruction from the terminal of the clinical laboratory, a blood glucose measurement device 1801 sends a reply to the terminal 1903 of the clinical laboratory acknowledging transmission with a new metric for measurement results.

This reply method can be designed so that the data format from a conventional measurement device to the terminal 1903 of the clinical laboratory can be used just as it is, so there is no need to change the data reception processing by which the terminal 1903 of the clinical laboratory receives data from the blood glucose measurement device 1801.

This can be accomplished, for example, by setting 999999 as a system reservation number for the user ID in advance. Then, if the user ID is 999999, it is treated as system information in the metric evaluation application 2703.

When the terminal 1903 of the clinical laboratory receives data from the blood glucose measurement device 1801, the data is received as the measurement result for user ID 999999, just as with a conventional method. Then, this result is also outputted, by a conventional method, to the laboratory terminal output file 2702 outputted from the terminal 1903 of the clinical laboratory.

In the metric evaluation application 2703, if the user ID is 999999, rather than normal measurement, the ID is recognized as system information.

At this point, the sensor ID is referred to. In system information, the meaning of a sensor ID can be freely decided.

Accordingly, if the sensor ID is 000001, for example, this is given the meaning of sending a reply from the measurement device about a metric change instruction. Consequently, analysis will be performed assuming that all the measurement data from that point onward has been sent with a new metric appended, to the measurement device that issued this measurement data.

Sensor IDs other than 00001 can be used as system information for other purposes.

In this embodiment the user ID was used as a system reservation number, but the sensor ID or patient ID may instead be used as a system reservation number.

If this method is not employed, if blood glucose measurement is performed by a measurement device while the terminal 1903 of the clinical laboratory is notifying all the registered blood glucose measurement devices 1801 of a change, or even after that, if the measurement device is in a state in which communication is impossible, the previous metric data will be acquired and the transmission of transmission data will be awaited. After this, data is transmitted at the point when communication is restored. Thus, there is the possibility that the terminal 1903 in the clinical laboratory that receives will malfunction by treating this as a new metric.

However, by adopting the above method, at the point when communication is restored, the measurement device receives a notification of the changes from the terminal 1903 of the clinical laboratory that had been deferred. The measurement device transmits stored data that has already been measured before sending a reply acknowledging this, after which it sends a reply acknowledging the metric changes. Consequently, the timing of the metric changes can be ascertained for each measurement device, and there is no mingling of old metrics with new metric.

A method for switching the type of metric data to be acquired was described above, and now a method for detecting abnormalities automatically will be described.

In the description of the application screen shown in FIGS. 28 to 37, etc., an example was given in which the manager of the laboratory performed screen operations and designated what was to be analyzed, the results of which were then displayed.

In contrast, the application may, for example, perform automatic background processing periodically, such as once a day, and a warning may be issued if there is data that matches a specific predetermined condition.

A processing example of the application in that case will now be given.

For example, the application is automatically launched each day at 12:00, and for all the measurement results within the period of the past week, for example, the overall average value of the time spent on patient identification is compared individually with the user-specific average values. If the number of times shorter than a predetermined length of time (such as 10 seconds) is greater than a predetermined number of times (such as two times), a warning is issued as a pop-up window on the display screen. Furthermore, as a better abnormality detection method, the analysis described in FIGS. 46 to 54 may be performed automatically and sequentially.

The warning screen display includes the name of the user in question, the type of matching condition, the actual length of time, and data about the number of times.

The above method allows the manager of the laboratory to ascertain which cases are problematic without actively analyzing them.

Similarly, as another means for allowing the manager of the laboratory to ascertain which cases are problematic without actively analyzing them, a certain parameter may be compared with its values from the past, and a warning issued if there is a major change.

A processing example of the application in that case will now be given.

For example, the application is automatically launched each day at 12:00, and the average length of time it took for a scan over the last 24 hours is found for each measurement device. Separately, the average length of time for a scan in 24 hours is found for each measurement device.

The difference between these average values is found for each measurement device, and if there is a measurement device for which the current average time is longer by more than a predetermined length of time (such as 2 seconds) than a week ago, a warning is issued as a pop-up window on the display screen warning.

The warning screen display includes the ID numbers of the measurement device in question, the type of matching condition, how much longer the time was, and so forth.

The above method allows the manager of the laboratory to ascertain which cases are problematic without actively analyzing them.

Also, if the above automatic analysis reveals a problem with a user's skill, for example, an instruction to receive guidance from a highly skilled user can be issued automatically, which further reduces the workload of the laboratory manager.

Specific examples of this are given below.

The metric data (measurement of the time) 2112 required for the entire measurement is used as metric data, for example. For instance, one week after the introductory training of user A, the terminal 1903 in the clinical laboratory finds the average value of the time (metric data 2112) that it took user A for the entire measurement, and if this exceeds the 120 seconds, it is concluded that there is a skill problem.

When this happens, the system refers to the user's work shift table and organization chart stored in the terminal 1903 of the clinical laboratory, and searches for a user B with the shortest average value for the metric data (measurement of the time) 2112 required for the entire measurement among users with the same shift and the same organization.

The organization chart and work shift table may be inputted in advance, or may be automatically measured from the actual measurement situation.

After the search, the terminal 1903 of the clinical laboratory sends both guidance information A and guidance information B to all the blood glucose measurement devices 1801 via the wireless communication means 2001 and the wired communication means 2003.

The guidance information A includes information indicating that "user A is to receive guidance from user B." The guidance information B includes information indicating that "user B is to give guidance to user A."

A blood glucose measurement device 1801 that has incorporated the guidance information A notifies the terminal 1903 of the clinical laboratory, via the wireless communication means 2001 and the wired communication means 2003, that the display of the guidance information A is finished, after displaying the guidance information A on the touch panel 1804 when user A has logged in for patient measurement.

Upon receiving this, the terminal 1903 in the clinical laboratory stores this information indicating that the guidance information A has been displayed, and sends an instruction through the wireless communication means 2001 and the wired communication means 2003 to all the blood glucose measurement devices 1801 to clear the guidance information A. Consequently, user A will see the guidance information A only once.

Similarly, a blood glucose measurement device 1801 that has incorporated the guidance information B notifies the terminal 1903 of the clinical laboratory, via the wireless communication means 2001 and the wired communication means 2003, that the display of the guidance information B is finished, after displaying the guidance information B on the touch panel 1804 when user B has logged in for patient measurement.

Upon receiving this, the terminal 1903 in the clinical laboratory stores this information indicating that the guidance information B has been displayed, and sends an instruction through the wireless communication means 2001 and the wired communication means 2003 to all the blood glucose measurement devices 1801 to clear the guidance information B. Consequently, user B will see the guidance information B only once.

Users A and B contact each other separately, and training is conducted using any of the blood glucose measurement devices 1801.

After completion of the training, the blood glucose measurement device 1801 that was used notifies the terminal 1903 of the clinical laboratory via the wireless communication means 2001 and the wired communication means 2003 that user A has received guidance from user B.

Upon receiving this, the terminal 1903 in the clinical laboratory deletes the information indicating that guidance information A and guidance information B have been displayed, and assumes that that all the processing has been performed.

In a state in which guidance information A and guidance information B have already been displayed, if even the next day there is no notification to the effect that user A has received guidance from user B, the terminal 1903 in the clinical laboratory displays the guidance information again by transmitting the guidance information A and guidance information B again.

This is carried out every day until the arrival of a notification to the effect that user A has received guidance from user B. This makes it possible to prompt the user to receive guidance sooner.

The preceding description was given for a case in which analysis of metric data is done by the terminal 1903 in the clinical laboratory, but as another example, the metric data may be put in an external cloud server or the like, rather than in just the terminal 1903 in the clinical laboratory.

In this case, the system configuration in a hospital for acquiring metrics is assumed to have a function of uploading metric data to an external server, in addition to what has been discussed up to now.

The metric data uploaded to the external server may be the laboratory terminal output file 2702 mentioned above, used just as it is. However, since patient or user information is included, patient IDs and user IDs are replaced with something else for the sake of privacy.

In this case, these IDs can be made easier to deal with by the person doing the analysis if fictitious names are used, rather than just numbers and letters.

Also, the blood glucose measurement results for patients are deleted because they are private information and are not necessary for analysis.

Thus, let us assume that when the data is placed on an external cloud server or the like, analysis is obtained that is the same as what a third party other than the manager of the testing department of the hospital has indicated up to this point. Consequently, not only can a fair evaluation be made, but it is also possible to provide a service business run by a third party that performs analysis and gives business proposals, in place of the busy manager of the testing department.

As in this embodiment, when metric data is put on an external cloud server or the like, metric data from a plurality of hospitals may then be put on the server and shared.

In this case, the laboratory terminal output files 2702 acquired in a plurality of hospitals may be directly uploaded to an external cloud server or the like, or, depending on the purpose, just the required metric may be selected and uploaded from the laboratory terminal output file 2702.

For example, let us assume that the data to be uploaded is just the "total measurement time" selected from the laboratory terminal output file. In this case, the "total measurement times" are collected by hospital on a single server from a plurality of hospitals.

As a result of analyzing the data with a server data analysis application, the skill level at each hospital is learned by gathering information at the national level and comparing the average for a given department by hospital, for example. Also, operational efficiency for each type of measurement device is learned by comparing the average by model for the measurement devices used by each hospital.

Depending on the results, each hospital can take measures such as carrying out a review of workflow and work systems. In particular, comparing the by-hospital monetary loss to be displayed in the estimated loss display box 4501 with that of other hospitals clarifies the portions to be improved in hospitals where this numerical value is poor, and can lead to improvements in hospital management.

The server data analysis application may be on a server, or may be on another terminal that can access data on the server.

In another embodiment, analysis of metric data may be performed by a measurement device. Mall hospitals sometimes have no clinical laboratory terminal, and a stand-alone measurement device is used. In a case such as this, the acquired metric data may be stored inside the measurement device.

The metric data may be in the same format as the laboratory terminal output file mentioned above, or just the metric data required for analysis, excluding information such as the measurement device ID, may be stored in order to save the memory.

The analysis method is the same as what was discussed above, except for the comparison of each measurement device, and the results are displayed on the touch panel 1804 of the measurement device.

Embodiment 3

The blood glucose measurement device (biological information measurement device) pertaining to yet another embodiment of the present invention will now be described through reference to FIGS. 57 to 61.

In general, feedback from patients is important in a hospital. What is most often done is to obtain feedback about satisfaction and so forth from a questionnaire or the like at the time of discharge from the hospital. This, however, is limited to just assessing the overall impression, and detailed questions are not asked about individual procedures and so forth.

Also, if some time has passed since a particular treatment, a patient often does not remember what he thought about the treatment. For example, a patient usually forgets how satisfied he was with individual blood glucose measurements, and collecting this information entails quite a lot of work.

In this embodiment, we will describe a method for collecting and tabulating information such as the satisfaction of patients with various measurements.

The blood glucose measurement device in this embodiment comprises the same system configuration as the blood glucose measurement device described in the second embodiment.

This embodiment comprises a configuration that is the same as the system of the measurement device main body shown in FIG. 19, and even as an entire measurement system, comprises a configuration that is the same as that shown in FIG. 20.

Figure 57:
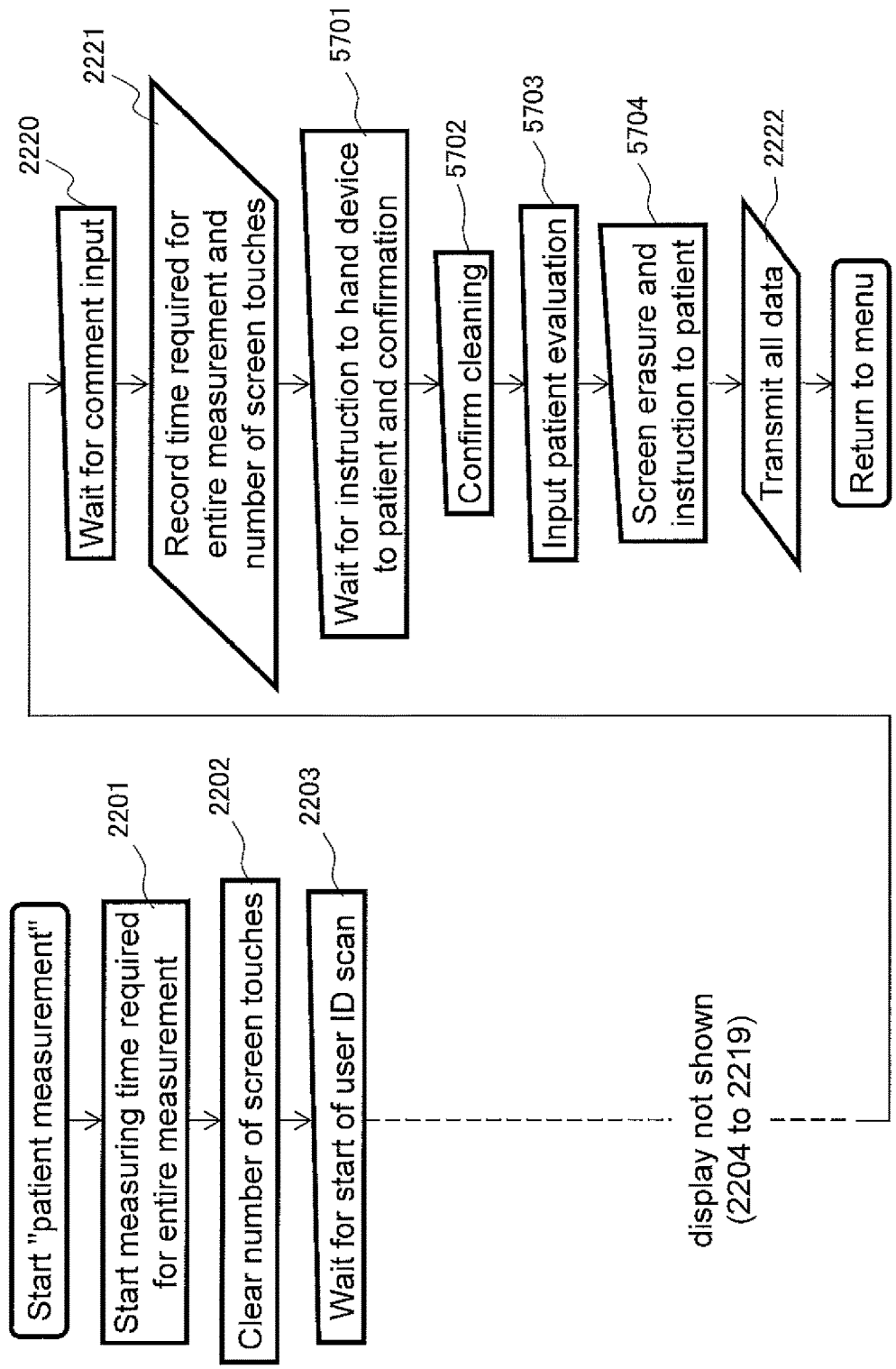
FIG. 57 shows the processing flow of a measurement device in Embodiment 3 of the present invention.

More specifically, FIG. 57 shows the measurement flow in the blood glucose measurement device 1801 of this embodiment.

In FIG. 57, steps 5701 to 5704 are added to the measurement flow in Embodiment 2 shown in FIG. 22, between step 2221 and step 2222. Therefore, the flow of steps 2201 to 2221 will not be described again.

In this embodiment, the metric data (measurement of the time) 2112 required for the entire measurement by the blood glucose measurement device 1801 is step 2221, etc., is recorded in the metric storage area 1909, and then in step 5701 an instruction to hand the measurement device to the patient is displayed. Consequently, the user (nurse), the hands confirms the instruction and then hands the measurement device to the patient.

Figure 60:
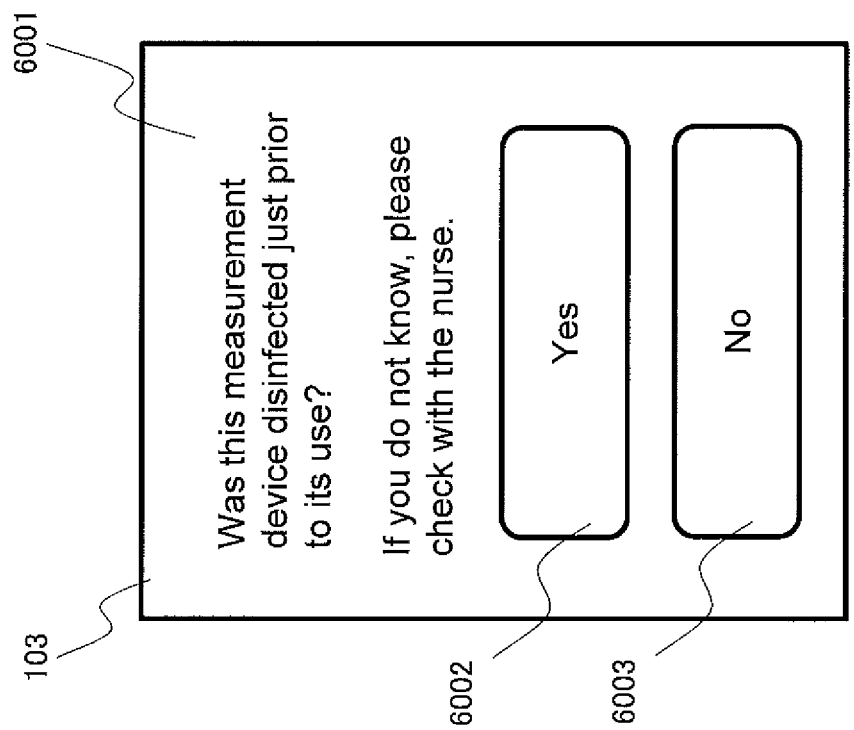
FIG. 60 shows a cleaning confirmation screen in Embodiment 3 of the present invention.

In step 5702, there is a state in which the screen shown in FIG. 60 is displayed. This is a screen which is displayed to prevent hospital-acquired infections.

That is, a measurement device that is assumed to be used for measuring the blood of a plurality of patients is supposed to be cleaned before measuring each individual patient. Here, however, since patient touches the measurement device, the device is checked again just to make sure.

In FIG. 60, on the screen of the liquid crystal display component 103 is shown, as a confirmation item 6001, a question regarding whether or not cleaning has been performed. There are two options: 6002 and 6003.

Normally, the "Yes" of option 6002 is selected, but in the event that cleaning has not been performed, the "No" of option 6003 is selected.

If the "No" of option 6003 is selected, although not depicted, a message of "return the measurement device to the nurse ask for it to be disinfected" is displayed. The nurse thereupon cleans the device and, at the same time, also disinfects the fingers of the patient that touched the measurement device before cleaning.

After confirmation of performing these tasks has been inputted, the flow goes back to step 5702, and the screen shown in FIG. 60 is displayed.

If the "Yes" of option 6002 has been selected on the screen in FIG. 60, in step 5703 in FIG. 57 a message is displayed requesting the input of information related to the patient's satisfaction, and the system waits for this input.

Information related to satisfaction inputted by the patient is recorded as part of the metric in the metric storage area 1909. Then, in step 2222, all the data is sent through the communication controller 1902 to the terminal 1903 of the clinical laboratory.

At this point, information about patient satisfaction acquired in step 5701 is sent placed in the reserve area 2309 shown in FIG. 24. Therefore, in the subsequent processing, this information can be handled the same as in the processing of metric data shown in the Embodiment 2.

FIG. 58 shows the patient satisfaction input screen displayed in step 5701. In FIG. 58, three questions 5801 to 5803 are displayed on the screen of the liquid crystal display component 103.

The first question 5801 asks about pain experienced by the patient during this measurement. The question 5801 comes with 11 radio buttons 5805 for selecting the degree of pain, with these buttons located below a simulation image 5804 that indicates the degree.

The patient taps a finger on one of the radio buttons 5805 to make a selection. A state in which "3" has been selected is shown in FIG. 58.

The second question 5802 asks about the patient's satisfaction. The question 5802 comes with five options 5806, which have radio buttons 5807 for selecting one of the options.

The patient taps one of the radio buttons with a finger to make a selection. A state in which "normal" has been selected is shown in FIG. 58.

The third question 5803 asks about the patient's perceptions. The question 5803 comes with four items as the options 5808. The items that can be selected here, in addition to those related to the current measurement, ask for the patient's opinion regarding the general experience in the hospital.

In FIG. 58, "unsatisfied with diet" is an example of this. Also, repeatedly asking numerous questions during a single measurement can be hard on the patient. Thus, the number of questions may be kept small, with different questions being displayed for each measurement.

Also, the options 5808 come with check boxes 5809 so that a plurality of items can be selected. The patient taps these check boxes with a finger to select as many options as desired.

FIG. 58 shows a state in which the "took a long time" "was stressful" have been selected. When the patient selects one of the radio buttons 5805 and one of the radio buttons 5807, then the OK button 5810 becomes selectable. The OK button 5810 is then tapped with a finger by the patient to end the input.

At the point when input is finished, the screen used for input in step 5704 is erased, and in its place a message of "return measurement device to nurse" is displayed.

The patient complies with this and returns the blood glucose measurement device 1801 to the user, at which point the screen shown in FIG. 58 is erased so that the user will not see the evaluation given by the patient.

Although not depicted, the settings can be adjusted to switch between enabling and disabling this function.

That is, when enabled, as indicated above, patient satisfaction is inputted in step 5701. On the other hand, when disabled, step 5701 is skipped and patient satisfaction is not inputted. When disabled, a code that means "disabled" is placed as metric data pertaining to patient satisfaction in the reserve area 2309 and sent.

Figure 59:
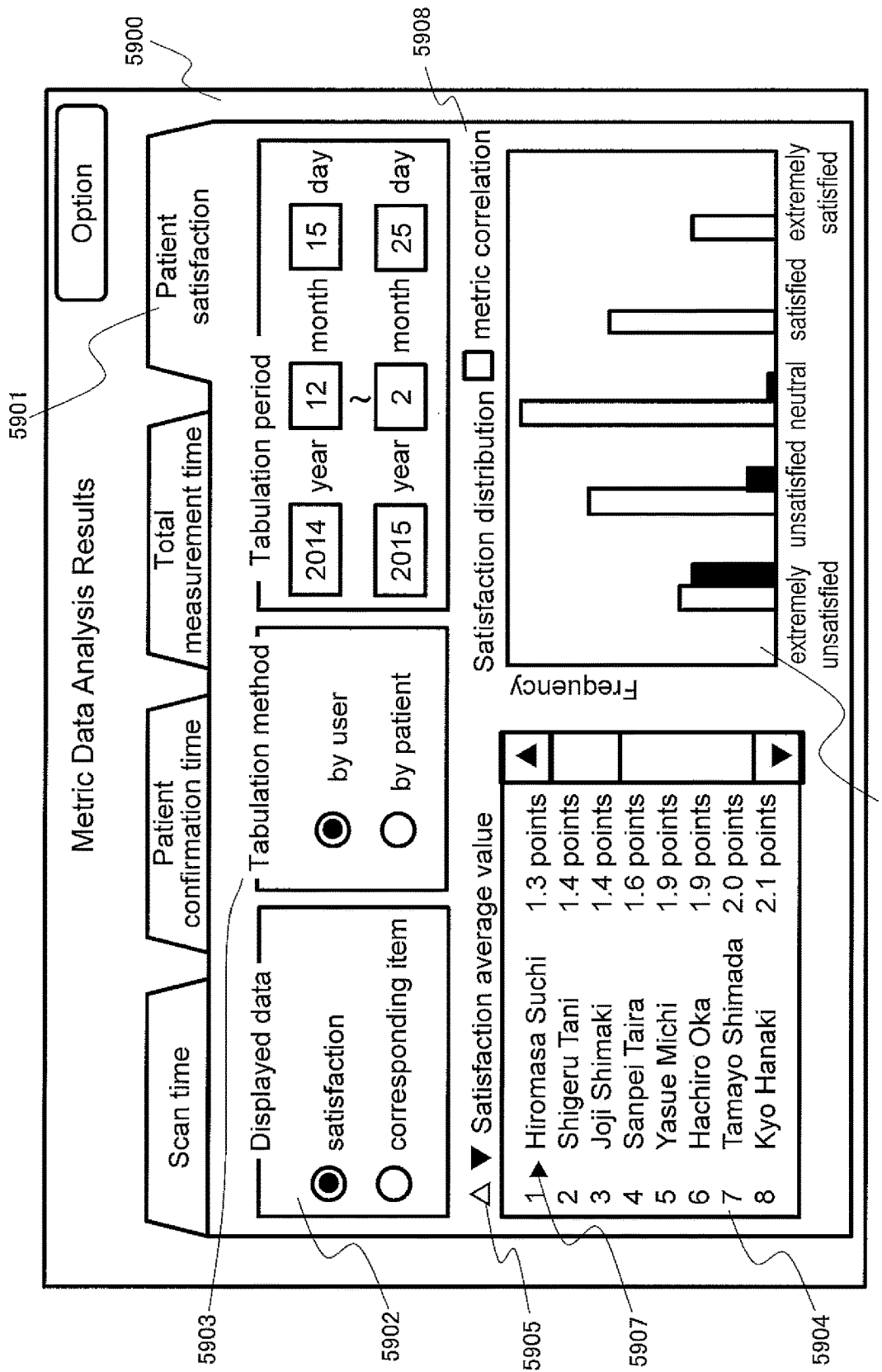
FIG. 59 shows a metric evaluation application screen in Embodiment 3 of the present invention.

FIG. 59 shows an example of the screen when displaying a metric related to patient satisfaction in the evaluation application 2703 in FIG. 27.

This screen uses patient satisfaction as metric data, and shows the result of analyzing this by user. In FIG. 59, 5900 is the entire display screen. On the screen 5900 is shown a state in which a patient satisfaction display tab 5901 is selected.

A displayed data selection 5902 is provided to select the results of which questions 5801 to 5803 shown in FIG. 58 to display as the data to be displayed on this screen. Here, when "pain index" is selected, the result of question 5801 is displayed. When "satisfaction" is selected, the result of question 5802 is displayed. When "corresponding item" is selected, the result of question 5803 is displayed.

In FIG. 59 is shown a state in which "satisfaction" is selected. Since the display on the screen is similar when "pain index" and "corresponding item" are selected, the description is omitted here.

With the tabulation method 5903, it is possible to select the viewpoint from which to perform the evaluation. If the evaluation is by user, analysis and evaluation are performed by focusing on the user individually. This screen shows the case when by-user has been selected. In addition, evaluation by patient can also be selected, in which case it is possible to display the satisfaction by patient.

The ranking table 5904 displays a list of user names and average values, starting with the lowest average value for each user. A switch 5905 can be used to switch between descending and ascending order in this table. The average shown here is the average value when five points means "very good," four points means "good," three points means "normal," two points means "bad," and one point means "very bad." Therefore, if this value is small for a person, it means that the patient satisfaction is low.

A distribution graph 5906 shows the satisfaction distribution for all the data as a white histogram, and shows the data for a particular user of interest as a black histogram.

The user of interest is switched by clicking on the user name in the ranking table 5904. The user of interest that is currently selected has a selection mark 5907 next to it.

By default, the top position of the ranking table 5904 is the user of interest, and the display is such that the status of the user most likely to be problematic can be confirmed right away from the black histogram. Therefore, in the ranking table 5904, the users are displayed starting at the top with the most problematic user.

If we turn our attention to the content of this screen, the user with the lowest point average is Hiromasa Suchi. A look at the distribution shows that satisfaction in the black histogram is shifted in the bad direction with respect to the white entire histogram.

Consequently, it is visually apparent that satisfaction with measurement by Hiromasa Suchi is considerably lower. As a result, measures can be taken for Hiromasa Suchi, such as having him undergo training.

Since the step of producing this screen can be performed in substantially the same way as that shown in Embodiment 2, it will not be described again here.

Figure 61:
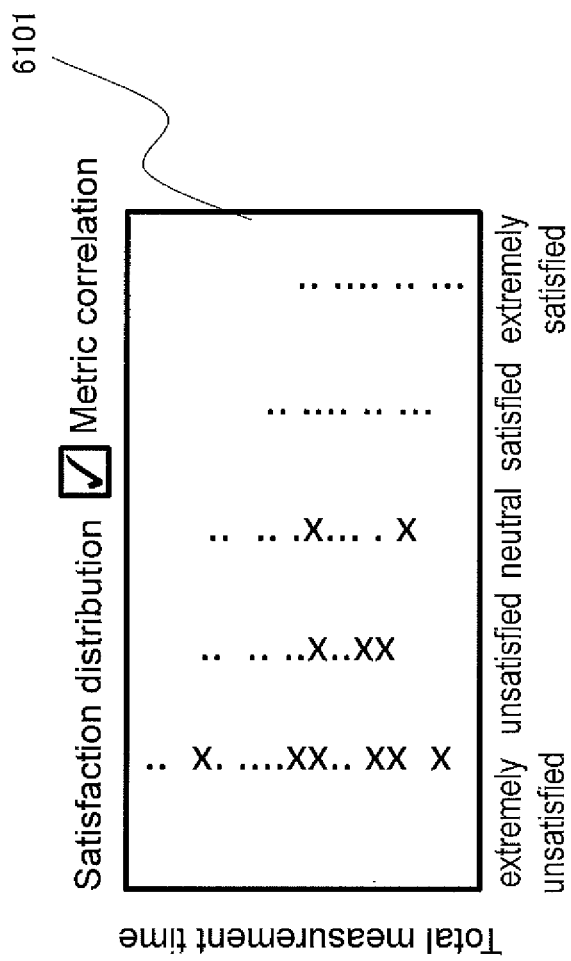
FIG. 61 shows a metric correlation diagram in Embodiment 3 of the present invention.

When a check is placed in the metric correlation display checkbox 5908, the distribution graph 5906 portion is switched to the metric correlation diagram 6101 shown in FIG. 61.

In FIG. 61, the horizontal axis is user satisfaction, the vertical axis is the metric data (measurement of the time) 2112 required for the entire measurement at that point, data is plotted in points for everyone, and just the data for the user of interest is plotted with x marks.

In general, the shorter is the measurement time, the higher is the patient satisfaction. Thus, if satisfaction with the user of interest is low and there is a tendency for the measurement time to be longer, measures can be taken with this user of interest, such as providing more training, so that the user can measure more quickly.

Also, even though a user tends to take a long time for measurement, if satisfaction with that user is high, there is a possibility that the measurement time is longer because the user is communicating more thoroughly with the patient. Accordingly, whether or not retraining is necessary, etc., can be easily determined.

In this regard, more accurate overall determination can be performed than when determining the need for training solely from the metric data (measurement of the time) 2112 required for the entire measurement as described in the second embodiment.

With the user of interest shown in FIG. 61, although satisfaction is low, the measurement time is far from tending to be long. Therefore, in this case, it is considered that the user himself is having some other problem, and measures can be taken such as resolving the problem through interviews and the like.

As described above, it is possible to take measures that match the circumstances by combining the information about patient satisfaction with other metric data, so that the situation becomes clearer.

In the above example, it is assumed that the patient's opinions pertaining to measurement and his general experience in the hospital are confirmed as the options 5808, but in addition to this, opinions about the patient's health and recovery status may be included.

For example, questions such as "Were you able to go to the toilet on your own ?", "Were you able to finish your meals ?", and "Were you able to sleep well at night ?" can be added. These answers can be tabulated and checked and then used to provide guidelines for when to discharge the patient and confirmation of the degree of recovery.

Embodiment 4

The blood glucose measurement device (biological information measurement device) pertaining to yet another embodiment of the present invention will now be described through reference to FIG. 62.

The blood glucose measurement device in this embodiment combines the principal features of the blood glucose measurement devices described in Embodiments 1 and 2. Therefore, the configurations of equipment and systems are the same as those shown in Embodiments 1 and 2 above.

The difference from Embodiments 1 and 2 above are as follows. In Embodiment 1, in step 327 in FIG. 3, in the transmission of the data from the temporary memory, exactly the same format as in the prior art in FIG. 15 is used, but in the embodiment given here, for comments A to C (1507 to 1509), information that distinguishes whether or not a comment was selected as a report comment is assumed to be added.

This distinguishing information is only one bit for each comment. Usually, the leading bit is 0 for both alphanumeric code and Japanese kanji code. For this reason, this portion is used as an example here, when the first bit of the leading byte of each comment is a report comment, it is "1," and otherwise it is "0."

In addition to this method of adding information that distinguishes whether or not a selected comment is a report comment, this information itself may be stored as a metric in the reserve area 2309 in FIG. 24.

Consequently, as shown in FIG. 15, the contents of report comments are associated with the user IDs 1502 and the patient IDs 1504 and stored in the temporary memory. In step 327, all the data stored in the temporary memory in this format is sent through the communication controller 105 to a terminal 106 (=1903) in the clinical laboratory. In the terminal 1903 of the clinical laboratory, the report comments are stored along with other metric data in the laboratory terminal output file 2702 shown in FIG. 27.

The metric evaluation application 2703 has the function of analyzing the report comments and the other metric data stored in the laboratory terminal output file 2702, and displaying these as evaluation data.

Here, as an example of this, the processing procedure for evaluating the metric data (measurement of the time) 2112 required for the entire measurement when report comments are displayed will be given below.

This procedure is carried out in order to evaluate how the time required for the entire measurement is affected by displaying the report comments. To simplify the description, the processing shown here is for when the report comments are displayed just once, at the time of the next measurement.

Figure 62:
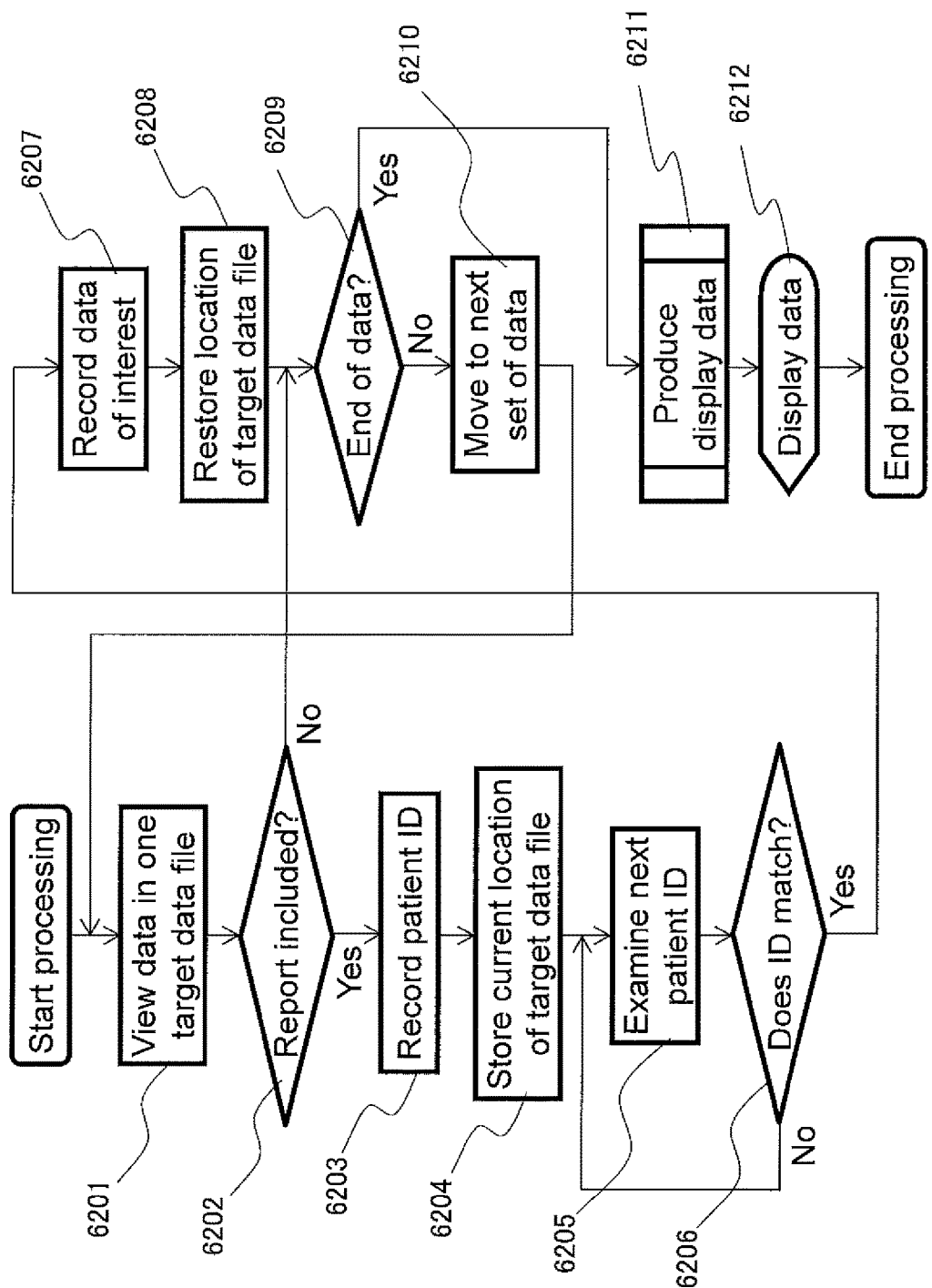
FIG. 62 shows the processing flow of report evaluation in Embodiment 4 of the present invention.

FIG. 62 is a flowchart of the selection of the metric data (measurement of the time) 2112 required for the entire measurement, when report comments are displayed, from the target data file. Here, the target data file is produced by the same processing as in steps 3801 to 3805 in FIG. 38.

In FIG. 62, first, in step 6201, the first packet data from the target data file is examined.

In step 6202, the system checks whether or not a report comment is included in this data, and if none is included, the subsequent processing is skipped.

If a report comment is included, in step 6203 the patient ID of the data of interest is read. Since the report comment for this patient will be displayed measurement of the next patient, thereafter the system searches for a record of the patient ID.

First, in step 6204, the order of the target data currently being processed is stored.

Next, in step 6205, the following data is examined, and the patient ID thereof is read.

Next, in step 6206, this patient ID is compared with the patient ID of the data of interest read in step 6203, and if they are different, steps 6205 to 6206 are repeated until the two match.

Next, in step 6206, if the two patient IDs match, it means that this data is the data from when the report comment was displayed. Therefore, in step 6207, various metrics are recorded, including the metric data (measurement of the time) 2112 required for the entire measurement this time.

In step 6208, the order of the target data stored in step 6204 is restored.

In step 6209, the system checks whether or not all of the data in the target data file has been searched, and not all has been searched, in step 6210 and the order of the target data is advanced by one, and everything from step 6201 onward is repeated with the next data.

On the other hand, if processing of all the data is finished in step 6209, display data is produced in step 6211, and data display is performed in step 6212.

In step 6211 of producing the display data, the various metrics from measurement in which a report comment was displayed, which were selected from among all the target data files, are used to produce display data indicating the difference between when there is and is not a report comment.

Many variations on this method are possible. For example, the average value of the metric data (measurement of the time) 2112 required for the entire measurement in all target data files, and the average value of the time (metric data 2112) required for the entire measurement only during measurement in which the report comment was displayed are found, and the two averages are displayed so that they can be compared in step 6212.

Thus, what kind of effect shows up in the average value of the time (metric data 2112) required for the entire measurement can be confirmed report comments.

These can also be displayed by user to evaluate the effect of the display of report comments for each user.

A method of comparing between overall measurement and measurement when a report comment is displayed was given above, but it is also possible to compare between measurement when a report comment is displayed and measurement when a report comment is not displayed.

Here, a method of evaluating the effect of report comments on measurement time was given, but various kinds of evaluation in which report comments are used are also possible.

For instance, the effect of a report comment can be ascertained more accurately by showing the correlation between the report comment usage status and patient satisfaction shown in Embodiment 3.

The biological information measurement device of the present invention includes a screen display means, a patient identification means, a means for measuring biological information about the patient, and a means for inputting a comments from the measurer. This biological information measurement device comprises a means for making some or all of the inputted comments report comments and storing them along with information identifying the patient, a means for searching for a patient in the memory component after that patient has been identified by the patient identification means, and a means for displaying on the screen display means any report comments corresponding to the patient for which the search was conducted. Consequently, a comment left by the measurer during the previous patient measurement can be conveyed to the measurer during the current measurement, without mistaking the patient and without overlooking any patients.

The present invention is also characterized by having a means for selecting a report comment to be stored along with information identifying the patient, from among the comments entered with the comment input component.

The present invention is also characterized by having a means for designating a report comment from among the comments inputted during comment input, as the report comment selection means.

The present invention is also characterized by having a means for designating which comments will be report comments in advance, as the report comment selection means.

The present invention is also characterized by having a means for deleting from the storage component any report comments that have already been displayed after the report comments are displayed on the screen display means.

The present invention is also characterized by having a means for selecting whether or not to delete displayed report comments when the report comments are displayed on the screen display means.

The present invention is also characterized by comprising a means for designating the number of times a report comment is to be displayed when report comments are selected during the comment input.

The present invention is also characterized by having a means for designating the period in which a report comment is to be displayed when report comments are selected during the comment input.

The present invention is also characterized by having a means for storing the date and time when a comment was inputted in the means for storing information identifying a patient, and deleting from the storage component any report comments for which a specific predetermined length of time has elapsed.

The present invention is also characterized by having a communication means, having a means for taking in, by this communication, report comments stored in a separate biological information measurement device, and having a means for storing these along with the report comments it has stored itself, and displaying on the screen display means the report comments corresponding to a patient when that patient has been identified.

Furthermore, in order to solve the above-mentioned conventional problems, the biological information measurement system of the present invention consists of a biological information measurement device and a data processing device for analyzing the data sent from the biological information measurement device, wherein the biological information measurement device comprises a means for measuring biological information about a patient, a means for acquiring metric data, and a means for communicating between these. The data processing device comprises a means for producing evaluation data from transmitted metric data, and various kinds of information other than biological information can be acquired and analyzed to obtain information that is useful in hospital management and the like.

The present invention is also characterized in that the metric data is a specific length of time.

The present invention is also characterized in that the specific length of time the time required to read a non-contact tag.

The present invention is also characterized in that the specific length of time is the time required for the entire measurement of the biological information.

The present invention is also characterized in that the specific length of time is the time required for blood collection.

The present invention is also characterized in that the specific length of time is the time required for patient confirmation.

The present invention is also characterized in that the specific length of time is the time required for comment input.

The present invention is also characterized in that the specific length of time is the time until a sensor strip is removed after being inserted.

The present invention is also characterized in that the specific length of time is the elapsed timed until measurement after the cleaning of a biological information measurement device.

The present invention is also characterized in that the specific length of time is the time required to link the biological information measurement device to a network.

The present invention is also characterized in that the metric data is a specific number of times.

The present invention is also characterized in that the specific number of times is the number of times the measurement results have been discarded.

The present invention is also characterized in that the specific number of times is the number of operations performed when biological information is measured.

The present invention is also characterized in that the specific number of times is the number of times help reference is performed when biological information is measured.

The present invention is also characterized in that the specific number of times is the number of times a warning is displayed when biological information is measured.

The present invention is also characterized in that the specific number of times is the number of times an operation is redone when biological information is measured.

The present invention is also characterized in that the specific number of times is the number of times an emergency test is conducted.

The present invention is also characterized in that the metric data is the remaining battery charge.

The present invention is also characterized by having a means for determining from the acquired remaining battery charge whether or not a biological information measurement device was returned to its charger.

The present invention is also characterized by having a means for comparing the remaining battery charge during the previous use with the remaining battery charge during the current measurement, and determining that the biological information measurement device was returned to its charger if the remaining battery charge during the current measurement is greater than the remaining battery charge during the previous use.

The present invention is also characterized in that medical data is used as metric data. The present invention is also characterized in that the medical data is a measurement result used for quality control of the measurement device.

The present invention is also characterized in that the medical data is a classification of whether or not the measurement is an emergency measurement.

The present invention is also characterized in that the medical data is the individual identification code of a measurement device.

The present invention is also characterized in that the medical data is the medical data is the recognition code of a sensor strip.

The present invention is also characterized in that the medical data is a comment input by the user.

The present invention is also characterized by comprising a means for finding the frequency at which a measurement device was returned to its charger, in the production of evaluation data from the acquired metric data.

The present invention is also characterized by comprising a means for finding the remaining battery charge in the first use after a measurement device was returned to its charger, in the production of evaluation data from the acquired metric data.

The present invention is also characterized by comprising a means for finding the error between the true value and the measurement result used for quality control, in the production of evaluation data from the acquired metric data.

The present invention is also characterized by comprising a means for finding the frequency of emergency measurement in the production of evaluation data from the acquired metric data.

The present invention is also characterized by comprising a means for finding the usage frequency of each instrument in the production of evaluation data from the acquired metric data.

The present invention is also characterized by comprising a means for finding the number of discarded sensor strips in the production of evaluation data from the acquired metric data.

The present invention is also characterized in that a means is provided for acquiring the number of sensor strips with a given recognition code and the sensor expiration date of that recognition code, and by comprising a means for finding the number of used sensors, by recognition code, from a sensor strip recognition code serving as the acquired metric data, and a means for setting the remaining number of sensors as the number of discarded sensors for any in which the sensor expiration date of that recognition code has already been reached.

The present invention is also characterized in that, in the production of evaluation data from the acquired metric data, a distinction is made between the selection of a comment inputted by the user, and custom input.

The present invention is also characterized in that a custom inputted comment is used as the evaluation data.

The present invention is also characterized in that a ranking table showing the ranking of the elements to be evaluated is used as evaluation data.

The present invention is also characterized in that a distribution graph of the elements to be evaluated is used as evaluation data.

The present invention is also characterized in that an elapsed time graph of the elements to be evaluated is used as evaluation data.

The present invention is also characterized in that the measurer is used as the evaluation target.

The present invention is also characterized in that a measurement device is used as the evaluation target.

The present invention is also characterized in that a patient is used as the evaluation target.

The present invention is also characterized in that a location is used as the evaluation target.

The present invention is also characterized in that a non-contact tag is used as the evaluation target.

The present invention is also characterized in that a barcode is used as a non-contact tag.

The present invention is also characterized in that an RF tag is used as a non-contact tag.

The present invention is also characterized by having a means for switching among a plurality of evaluation targets and producing a ranking table for the same metric data.

The present invention is also characterized by having a means for switching among a plurality of evaluation targets and producing a distribution graph for the same metric data.

The present invention is also characterized by having a means for switching among a plurality of evaluation targets and producing an elapsed time graph for the same metric data.

The present invention is also characterized in that a numerical value that quantifies the skill of the measurer is presented.

The present invention is also characterized in that a numerical value that quantifies the rule compliance awareness of a measurer is presented.

The present invention is also characterized in that a numerical value that quantifies the degree of soiling of a measurement device is presented.

The present invention is also characterized in that a numerical value that quantifies the malfunction of a measurement device is presented.

The present invention is also characterized in that a numerical value that quantifies the health of a patient is presented.

The present invention is also characterized in that a numerical value that quantifies the compliance of the patient is presented.

The present invention is also characterized in that a numerical value that quantifies the communication state by location is presented.

The present invention is also characterized in that a numerical value that quantifies the soundness of a non-contact tag is presented.

The present invention is also characterized by comprising a means for designating as data of interest one of the elements to be evaluated that are listed in the ranking table, and by having a means for displaying as a distribution graph the elements to be evaluated that correspond to the data of interest.

The present invention is also characterized by comprising a means for designating as data of interest one of the elements to be evaluated that are listed in the ranking table, and by having a means for displaying as an elapsed time graph the elements to be evaluated that correspond to the data of interest.

The present invention is also characterized by having a means for designating whether to select either a distribution graph or an elapsed time graph as the display format of the evaluation data.

The present invention is also characterized in that the distribution graph displays the distribution of only the data of interest as an overlay with the distribution of all the elements to be evaluated, so that they can be compared.

The present invention is also characterized in that the elapsed time graph displays the elapsed time of the data of interest as an overlay with the individual elapsed times of all the elements to be evaluated, so that they can be compared.

The present invention is also characterized in that the elapsed time graph displays only the elapsed time of the data of interest.

The present invention is also characterized in that the distribution graph displays the positions of the average values of all the elements to be evaluated.

The present invention is also characterized in that the distribution graph displays the positions of the average values of all the elements to be evaluated.

The present invention is also characterized in that a distribution graph displays the distribution of only the data of interest as an overlay with the distribution of all the elements to be evaluated, at different scales.

The present invention is also characterized in that the elapsed time graph is displayed with a low-pass filter applied to time.

The present invention is also characterized by having a function of determining whether or not to use the acquired metric data in the production of evaluation data on the basis of the date and time when the data was acquired.

The present invention is also characterized in that the start time and end time are designated, and any metric data acquired during that period is used in the production of evaluation data.

The present invention is also characterized in that the end time is set as the evaluation data production date.

The present invention is also characterized in that when the evaluation target has been switched, the period is switched.

The present invention is also characterized in that, in a biological information measurement device, there is a means for the measurer to enter a comment at the time of measurement, and in a biological information measurement system that transmits these comments to a data processing device, acquired metric data is written to all or part of the comment area sent from the biological information measurement device to the data processing device.

The present invention is also characterized in that, in writing the acquired metric data to all or part of the comment area sent from the biological information measurement device to the data processing device, the metric data is written after being encoded.

The present invention is also characterized in that the encoding of the metric data is accomplished by individual encoding means in accordance with the metric.

The present invention is also characterized by having a function of converting evaluation data into a monetary amount.

The present invention is also characterized by having a function of converting to a monetary amount by using the product of multiplying the unit price by the difference between the average value of all the elements of the evaluation target and the metric in the data of interest.

The present invention is also characterized in that if the data of interest is related to the work efficiency of a specific user, there is a function of converting to a monetary amount by using the product of multiplying the labor unit cost by the difference between the average value of all the elements of the evaluation target and the metric related to that measurer.

The present invention is also characterized by having a function of converting to a monetary amount by using the product of multiplying the unit cost of the sensors by the number of discarded sensor strips.

The present invention is also characterized by having a function of producing notes related to the data of interest from evaluation data.

The present invention is also characterized by having a function of producing a note related to the data of interest according to the distance between the peak position in the to distribution of all the elements to be evaluated and the peak position in the distribution of only the data of interest in a distribution graph.

The present invention is also characterized by having a function of producing a note related to the data of interest according to the difference between the average value of all the elements to be evaluated and the average value of only the data of interest in a distribution graph.

The present invention is also characterized in that a first threshold value and a second threshold value are determined in advance, if the distance between the peak positions exceeds the first threshold, a note related to the data of interest urges caution, and if the second threshold is exceeded, the note related to the data of interest recommends measures.

The present invention is also characterized in that in the distribution graph, if the distribution of only the data of interest exhibits two or more peaks, a note related to the data of interest urges confirmation of the elapsed time.

The present invention is also characterized having a function of producing a note related to the data of interest, according to the difference between the standard deviation in the distribution of all the elements to be evaluated and the standard deviation in the distribution of only the data of interest in the distribution graph.

The present invention is also characterized in that in the distribution graph, when the peak of the distribution of all the elements to be evaluated is at one end, if the peak in the distribution of only the data of interest is not in the same position, a note related to the data of interest urges caution.

The present invention is also characterized in that in the distribution graph, when there is a tendency for the distribution of all the elements to be evaluated to be concentrated at one end, if the distribution of only the data of interest does not have the same tendency, a note related to the data of interest urges caution.

The present invention is also characterized by having a function of producing a note related to the data of interest according to the elapsed time of the data of interest in an elapsed time graph.

The present invention is also characterized in that when the average value of the data of interest near the end of the evaluation data tabulation period is greater than a predetermined value, a note related to the data of interest urges caution.

The present invention is also characterized in that when the difference between the value of the data of interest near the start of the evaluation data tabulation period and the average value of the data of interest near the end of the period is greater than a predetermined value, a note related to the data of interest indicates that the training situation is good.

The present invention is also characterized in that when the value of the data of interest near the end of the evaluation data tabulation period changes suddenly compared to its previous value, a note related to the data of interest urges caution.

The present invention is also characterized in that the note related to the data of interest shown in claim 99 is produced with priority over the note related to the data of interest shown in claims 97 and 98.

The present invention is also characterized in that when the distribution of the data of interest near the end of the evaluation data tabulation period changes suddenly compared to its previous distribution, a note related to the data of interest urges caution.

The present invention is also characterized by having a function of automatically producing evaluation data periodically in a data processing device, and producing notes on the basis of this data.

The present invention is also characterized by having a function of displaying the produced notes on the screen.

The present invention is also characterized by having a function of storing evaluation data produced periodically, having a means for comparing to past evaluation data when evaluation data is produced, and having a function of displaying on the screen a note urging caution when there is a change of at least a predetermined value.

The present invention is also characterized by having a function of excluding designated data of interest during the production of evaluation data.

The present invention is also characterized by having a function of designating the data to exclude during production of evaluation data.

The present invention is also characterized by having a function of returning all the excluded data to what it was before and disabling the exclusion.

The present invention is also characterized by having a function of, when the type of metric data to be analyzed has been changed, returning all the data excluded prior to this to what it was before and disabling the exclusion.

The present invention is also characterized by having a function of changing the metric data to be acquired.

The present invention is also characterized by having a function of selecting the metrics data to be acquired in a data processing device.

The present invention is also characterized by having a function of transmitting the type of metric data selected in a data processing device to a biological information measurement device, and a function of replying that the type of metric data to be acquired in the future by the biological information measurement device that received this transmission has been switched.

The present invention is also characterized in that a data processing device has a function of transmitting acquired metric data to an external server, and comprises a means for producing evaluation data from metric data at the external server.

The present invention is also characterized in that a data processing device has a function of transmitting acquired metric data to an external server, further has a function of reading global metric data, including what was sent from other medical facilities and stored on an external server, and comprises a means for producing evaluation data from the global metric data.

The present invention is also characterized by comprising a means for producing evaluation data by medical facility from global metric data.

The present invention is also characterized in that when transmitting acquired metric data to an external server, a data processing device erases the personal information included in the metric data or replaces it with fictitious information.

The present invention is also characterized in that the personal information contained in the metric data is a biological information for a patient.

The present invention is also characterized in that the personal information contained in the metric data is a name and an ID.

The present invention is also characterized in that only some of the metric data had by a data processing device sent to an external server.

The present invention is also characterized by a consulting business that performs analysis on an organization that has acquired metric data, on the basis of evaluation data.

The present invention is also characterized by having a means for identifying measurers with high skill and measurers with low skill from evaluation data, with a note related to the data of interest being a note pertaining to the skill of the measurer.

The present invention is also characterized by having a function of instructing a measurer with low skill to receive instruction from a measurer with high skill.

The present invention is also characterized by having a function of instructing a measurer with high skill to give instruction to a measurer with low skill.

The present invention is also characterized by having a means for identifying measurers with a means for identifying the measurer and then, if there are measurers whose skill is low, comparing to these, and having a function of displaying an instruction to receive guidance from a measurer with high skill if the skill of the current measurer is low.

The present invention is also characterized by having a means for identifying measurers with a means for identifying the measurer and then, if there are measurers whose skill is high, comparing to these, and having a function of displaying an instruction to give guidance to a measurer with low skill if the skill of the current measurer is high.

The present invention is also characterized by having information about both the working pattern and the organization to which a measurer belongs, and having a function of giving a display so that if the skill of the current measurer is low, guidance will be received from measurers whose skill is high among measurers with similar organization and working patterns.

The present invention is also characterized by having information about both the working pattern and the organization to which a measurer belongs, and having a function of giving a display so that if the skill of the current measurer is high, guidance will be given to measurers whose skill is low among measurers with similar organization and working patterns.

The present invention is also characterized in that the names of measurers whose skill is low and the names of instructors whose skill is high are displayed to each other.

The present invention is also characterized in that information about the working patterns and organization to which a measurer belongs is inputted ahead of time.

The present invention is also characterized in that information about the working patterns and organization to which a measurer belongs is automatically generated from the actual measurement conditions.

The present invention is also characterized by including the biological information measurement device itself that is included in a biological information measurement system.

The present invention is also characterized in that blood glucose is measured as biological information.

The present invention is also characterized in that, a biological information measurement device, the biological information measurement device further comprises a to means for measuring biological information of a patient, and a means for acquiring metric data, and the biological information measurement device comprises a means for producing evaluation data from the acquired metric data.

The present invention is also characterized by having a means with which a non-measurer inputs information in the course of measuring biological information with a biological information measurement device, and the inputted information is treated as metric data.

The present invention is also characterized in that after a non-measurer uses the biological information measurement device to input information, the input screen is cleared so that the inputted information cannot be seen.

The present invention is also characterized in that the information inputted by a non-measurer is the subjective opinion of the non-measurer about measurement.

The present invention is also characterized by also having a means for previously disabling the means with which a non-measurer inputs information.

The present invention is also characterized by having a means for classifying the display of the subjective opinions of non-measurers by the user who is the measurer.

The present invention is also characterized by having a means for classifying the display of the subjective opinions of non-measurers by non-measurer.

The present invention is also characterized in that the metric data includes report comments.

The present invention is also characterized in that the metric data includes a means for identifying the patient and whether or not there is a report comment.

The present invention is also characterized by comprising a means for selecting data from evaluation data when a report comment is displayed.

The present invention is also characterized by having a means for displaying a comparison of metrics when a report comment is and is not displayed.

The present invention is also characterized by having a means for displaying a comparison of metrics when a report comment is displayed versus all situations.

INDUSTRIAL APPLICABILITY

The biological information measurement device pertaining to the present invention is, for example, a measurement device for measuring blood or the like in a face-to-face setting with a patient in a hospital, wherein a comment left by a measurer during measurement of the patient the last time can be conveyed to the user measuring the patient this time, without mistaking the patient and without any comments being overlooked. Therefore, patient safety can be ensured and emotional support can be provided more reliably, so this invention is useful as a blood glucose measurement device intended for use in a hospital.

REFERENCE SIGNS LIST 101 blood glucose measurement device (biological information measurement device)
102 central controller (controller)
103 liquid crystal display component (display component)
104 touch sensor (report item input component)
105 communication controller
106 terminal in clinical laboratory
107 data storage component (storage component)
108 barcode reader (identification information reader)
109 barcode
110 sensor connector (sensor mounting portion)
111 sensor strip (sensor)
112 blood glucose level calculator (measurement component)
113 report storage area (storage component)
201 user name tag
202 user ID barcode
203 patient wrist tag
204 patient ID barcode
205 bottle stored with sensor strips
206 sensor ID barcode
207 QC solution bottle
208 barcode of QC solution ID
301 to 327 processing steps in measurement device
401 comment selection list
402 comment content column
403 comment selection column
404 report designation column
405 scroll bar
406 to 409 examples of comments
410 end button
501 to 508 processing steps for comment input
601 to 603 data in report areas
604 area (patient ID)
605 area (registration date and time)
606 area (user ID)
607 to 608 area (report comments)
701 patient confirmation screen
702 confirmation button
703 report comment confirmation screen
704 OK button
801 to 806 processing steps for report display
901 entire comment editing screen
902 comment list display component
903 comment editor
904 end button
905 comment list loading component
906 comment edit button
907 comment delete button
908 comment add button
909 comment replace button
910 comment content column
911 report designation column
912 scroll bar
1001 report designation confirmation processing
1101 report comment confirmation screen
1102 to 1103 report comment maintenance check box
1201 to 1204 processing steps for report display
1301 comment list
1302 report count designation column
1303 to 1305 report count input box
1306 report count change icon
1307 report count increase button
1308 report count decrease button
1401 communication means (communication component)
1402 and 1403 blood glucose measurement devices (biological information measurement devices)
1501 header information
1502 user ID
1503 sensor ID
1504 patient ID (identification information)
1505 blood glucose value
1506 transmission date and time
1507 comment A
1508 comment B
1509 comment C
1801 blood glucose measurement device (biological information measurement device)
1802 sensor strip connector (sensor mounting portion)
1803 barcode reader (identification information reader)
1804 touch panel (report item input component)
1805 power switch
1806 help button
1807 home button
1808 back button
1809 patient measurement button
1810 QC measurement button
1811 STAT measurement button
1901 central controller (controller)
1902 communication controller
1903 terminal in the clinical laboratory
1904 data storage component (storage component)
1905 barcode
1906 sensor strip (sensor)
1907 blood glucose level calculator (measurement component)
1908 metric measurement means
1909 metric storage area
2001 wireless communication means
2002 docking station
2003 wired communication means
2004 urine component measurement device
2005 blood component measurement device 2006 hospital server
2007 electronic medical record
2008 accounting terminal
2101 to 2107 medical data
2108 to 2113 metric data
2201 to 2222 steps performed in measurement device
2301 header information
2302 user ID
2303 consumables ID
2304 patient ID
2305 measured value
2306 measurement date and time
2307 comment A
2308 comment B
2309 comment C
2501 to 2520 steps in reception flow of clinical laboratory terminal
2601 to 2604 packets of laboratory terminal output file
2701 data reception processing
2702 laboratory terminal output file
2703 metric evaluation application
2704 evaluation data production processing
2705 evaluation data display
2800 display screen
2801 tab (scan time analysis)
2802 tab (patient confirmation time analysis)
2803 tab (total measurement time analysis)
2804 tab (touch count analysis)
2805 option button
2806 tabulation method
2807 usage data selection component
2808 tabulation period selection component
2809 ranking table
2810 descending/ascending order selection button
2811 selection mark
2812 distribution graph
2813 overall distribution
2814 distribution of only users of interest
2815 elapsed time display check box
2816 position of average value
2901 elapsed time graph
2902 user-by-user learning curve
2903 user of interest learning curve
2904 position of average value
3001 tabulation period selection component
3002 overall distribution
3003 distribution of only measurement devices of interest
3101 elapsed time graph
3201 used data selection component
3202 overall distribution
3203 distribution of only barcodes of interest
3301 elapsed time graph
3401 elapsed time graph
3501 information display component
3502 threshold designation component
3503 distribution of users of interest
3601 overall distribution
3602 distribution of users of interest
3701 overall distribution
3702 distribution of users of interest
3801 to 3811 steps in main flow of metric evaluation application
3901 to 3904 steps in scan time screen drawing processing flow
4001 to 4015 steps in the user-by-user tabulation drawing processing flow
4101 to 4111 steps in ranking table drawing process flow
4201 to 4217 steps in the distribution graph drawing process flow
4301 metric data (blood deposition time)
4302 metric data (time until sensor removal)
4303 metric data (the number of times of "Help")
4304 metric data (number of times of "back")
4305 metric data (number of warnings)
4306 metric data (comment input time)
4307 metric data (remaining battery charge)
4308 metric data (wireless link time)
4309 metric data (cleaning time)
4310 metric data (number of measurements discarded)
4401 metric data using medical data (QC result)
4402 metric data using medical data (STAT measurement)
4403 metric data using medical data (measurement device ID)
4404 metric data using medical data (sensor ID)
4405 metric data using medical data (comments)
4501 estimated loss display column
4502 note
4601 overall average value
4602 average value of data of interest
4603 first threshold value
4604 second threshold value
4605 first boundary
4606 second boundary
4701 distribution graph
4702 overall distribution
4703 distribution of data of interest
4704 first peak
4705 second peak
4801 distribution graph
4802 overall distribution
4803 distribution of data of interest
4901 distribution graph
4902 overall distribution
4903 distribution of data of interest
5001 distribution graph
5002 overall distribution
5003 distribution of data of interest
5101 average value of all data
5102 first period during tabulation period
5103 average value in first period
5104 last period during tabulation period
5105 average value in last period
5106 difference
5107 threshold for determining training to be necessary
5201 learning curve
5202 first period during tabulation period
5203 average value in first period
5204 last period during tabulation period
5205 average value in last period
5206 difference between 5205 and 5203
5301 average value in the first period
5302 average value in last period
5303 the difference between 5302 and 5301
5401 first period during tabulation period
5402 maximum value in first period
5403 last period in tabulation period
5404 maximum value in last period
5405 difference between 5402 and 5404
5501 mask button for data of interest
5502 mask cancel button
5601 metric selection screen
5602 type of metric data that can be used
5603 scroll bar
5604 metric selection check box 5605 selected number display column
5606 detailed description display button
5607 cancel button
5608 apply button
5701 to 5704 measurement device processing flow for ascertaining patient satisfaction
5801 question 1
5802 question 2
5803 question 3
5804 simulation diagram expressing degree of pain
5805 radio button for selecting degree of pain
5806 patient satisfaction index
5807 radio button for selecting patient satisfaction
5808 four options
5809 selection check button
5810 input end button
5900 entire metric display screen
5901 patient satisfaction display selection tab
5902 display data selection component
5903 tabulation method selection component
5904 ranking table
5905 descending/ascending order switching button
5906 distribution graph
5907 selection mark
5908 metric correlation display check box
6001 checklist
6002 "Yes" button
6003 "No" button
611 metric correlation diagram
6201 to 6212 steps in flow of report evaluation

The invention claimed is:

1. A biological information measurement device, comprising:
- a sensor mounting portion to which is mounted a sensor for measuring biological information about a subject;
- a measurement component configured to measure biological information of the subject by using the sensor mounted to the sensor mounting portion;
- an identification information reader configured to read identification information about the subject;
- a display component configured to display the identification information read by the identification information reader and measurement results measured by the measurement component;
- a storage component configured to store the identification information and the measurement results, which are associated with each other;
- a controller that is connected to the sensor mounting portion, the measurement component, the identification information reader, the display component, and the storage component; and
- a report item input component to which are inputted report items that are to be transmitted from a first measurer who conducted measurement of the biological information to a second measurer who will conduct the next measurement on the same subject, wherein the controller:
- activates an input screen for inputting the report items on the display component for each measurement at the measuring component,
- when the report items are inputted at the report item input component, stores the report items and the identification information associated each other in correspondence with each measurement at the measuring component in the storage component, and
- when the identification information about the subject is read by the identification information reader, confirms whether or not there are report items on the basis of the information stored in the storage component, and if there are report items, displays them on the display component, wherein the controller causes the display component to display a selection screen that allows the user to select a comment related to the subject or measurement from among a plurality of choices prepared beforehand, wherein the controller causes the display component to display a selection screen that allows the user to select whether or not a comment selected by the user on the selection screen shall be in the report items, and wherein, for a comment that has already been selected as a report comment during the previous measurement, the controller causes the display component to display the selection screen that allows the user to select whether or not that comment will be in the report items, regardless of whether or not any comments have been selected during the current measurement.

* * * * *